(12) United States Patent
Grether et al.

(10) Patent No.: US 8,410,107 B2
(45) Date of Patent: Apr. 2, 2013

(54) N-PYRIDIN-3-YL OR N-PYRAZIN-2-YL CARBOXAMIDES

(75) Inventors: Uwe Grether, Efringen-Kirchen (DE); Paul Hebeisen, Basel (CH); Torsten Hoffmann, Weil am Rhein (DE); Stephan Roever, Inzlingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/267,920

(22) Filed: Oct. 7, 2011

(65) Prior Publication Data

US 2012/0094993 A1 Apr. 19, 2012

(30) Foreign Application Priority Data

Oct. 15, 2010 (EP) .................................. 10187724

(51) Int. Cl.
*A61K 31/4965* (2006.01)
*A61K 31/44* (2006.01)

(52) U.S. Cl. ..................... 514/252.1; 514/345; 544/408; 546/290

(58) Field of Classification Search .................. 544/408; 546/290

See application file for complete search history.

(56) References Cited

U.S. PATENT DOCUMENTS

| | | | |
|---|---|---|---|
| 3,940,418 A | 2/1976 | Hamilton | |
| 4,293,552 A | 10/1981 | Miesel | |
| 5,462,960 A | 10/1995 | Barth et al. | |
| 5,596,106 A | 1/1997 | Cullinan et al. | |
| 5,624,941 A | 4/1997 | Barth et al. | |
| 5,756,524 A | 5/1998 | Riordan et al. | |
| 6,028,084 A | 2/2000 | Barth et al. | |
| 6,355,631 B1 | 3/2002 | Achard et al. | |
| 6,432,984 B1 | 8/2002 | Barth et al. | |
| 6,479,479 B2 | 11/2002 | Achard et al. | |
| 6,509,367 B1 | 1/2003 | Martin et al. | |
| 6,518,264 B2 | 2/2003 | Achard et al. | |
| 6,566,356 B2 | 5/2003 | Achard et al. | |
| 6,734,176 B2 | 5/2004 | Achard et al. | |
| 6,858,603 B2 | 2/2005 | Achard et al. | |
| 6,872,717 B2 | 3/2005 | Achard et al. | |
| 6,906,080 B1 | 6/2005 | Barth et al. | |
| 7,229,999 B2 | 6/2007 | Hebeisen et al. | |
| 7,345,059 B2 | 3/2008 | Barth et al. | |
| 7,812,028 B2 | 10/2010 | Andjelkovic et al. | |
| 7,897,621 B2 | 3/2011 | Hebeisen et al. | |
| 8,088,920 B2 | 1/2012 | Hebeisen et al. | |
| 8,188,093 B2 | 5/2012 | Andjelkovic et al. | |
| 2001/0027193 A1 | 10/2001 | Achard et al. | |
| 2002/0019383 A1 | 2/2002 | Achard et al. | |
| 2002/0035102 A1 | 3/2002 | Achard et al. | |
| 2003/0055033 A1 | 3/2003 | Achard et al. | |
| 2003/0119810 A1 | 6/2003 | Achard et al. | |
| 2003/0162808 A1 | 8/2003 | Achard et al. | |
| 2004/0157823 A1 | 8/2004 | Achard et al. | |
| 2004/0235816 A1 | 11/2004 | Achard et al. | |
| 2004/0259887 A1 | 12/2004 | Dow | |
| 2005/0130953 A1 | 6/2005 | Achard et al. | |
| 2006/0229326 A1 | 10/2006 | Hebeisen et al. | |
| 2007/0293509 A1 | 12/2007 | Hebeisen et al. | |
| 2008/0070931 A1 | 3/2008 | Hebeisen et al. | |
| 2008/0085905 A1 | 4/2008 | Dietz et al. | |
| 2008/0085906 A1 | 4/2008 | Andjelkovic et al. | |

FOREIGN PATENT DOCUMENTS

| | | |
|---|---|---|
| AU | 740486 | 10/1998 |
| AU | 2001/237526 | 9/2001 |
| AU | 2001/293936 | 4/2002 |
| EP | 576357 | 12/1993 |
| EP | 656354 | 6/1995 |
| IL | 151321 | 11/2008 |
| WO | 96/02248 | 2/1996 |
| WO | 97/19063 | 5/1997 |
| WO | 98/31227 | 7/1998 |
| WO | 98/41519 | 9/1998 |
| WO | 98/43635 | 10/1998 |
| WO | 01/64633 | 9/2001 |
| WO | 01/64634 | 9/2001 |
| WO | 01/70700 | 9/2001 |
| WO | 02/28346 | 4/2002 |
| WO | 03/051850 | 6/2003 |

(Continued)

OTHER PUBLICATIONS

Munro et al., "Nature" 365:61-65 (1993).
Pacheco et al., "J. Pharmacol. Exp. Ther." 257(1):170-183 (1991).
Shinkai, H., "Mini Reviews in Medicinal Chemistry" 2:271-273 (2002).
Williamson et al., "Drugs" 60(6):1303-1314 (2000).
Mechoulam, R., "Cannabinoids as Therapeutic Agents" (CRC Press),:1-20 (1986).

(Continued)

*Primary Examiner* — Brian McDowell
(74) *Attorney, Agent, or Firm* — George W. Johnston; Patricia S. Rocha-Tramaloni; Gene J. Yao

(57) ABSTRACT

The present invention relates to compounds of formula I,

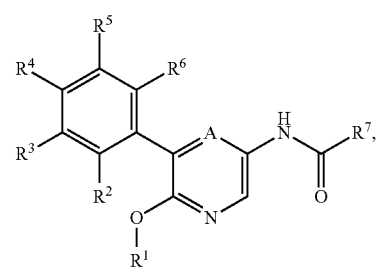

wherein A, $R^1$ to $R^7$ are defined in the description, and to pharmaceutically acceptable salts thereof. The present invention also relates to the manufacture of such compounds or their pharmaceutically acceptable salts, pharmaceutical compositions containing them and their use as medicaments for the treatment and/or prophylaxis of diseases which can be treated with HDL-cholesterol raising agents, such as dyslipidemia, atherosclerosis and cardiovascular diseases.

14 Claims, No Drawings

FOREIGN PATENT DOCUMENTS

| | | |
|---|---|---|
| WO | 03/051851 | 6/2003 |
| WO | 03/082191 | 10/2003 |
| WO | 03/084930 | 10/2003 |
| WO | 2004/110453 | 12/2004 |
| WO | 2004/111033 | 12/2004 |
| WO | 2004/111034 | 12/2004 |
| WO | 2004/111038 | 12/2004 |
| WO | 2004/111039 | 12/2004 |
| WO | 2008/040649 | 4/2005 |
| WO | 2005/073192 | 8/2005 |
| WO | 2006/106054 | 10/2006 |
| WO | 2007/011760 | 1/2007 |
| WO | 2007/147746 | 12/2007 |
| WO | 2008/031734 | 3/2008 |
| WO | 2008/040651 | 4/2008 |
| WO | 2009/121741 | 10/2009 |
| WO | 2010/051188 | 5/2010 |
| WO | 2011/029827 | 3/2011 |

OTHER PUBLICATIONS

"International Search Report PCTEP2011067753 mailed Jan. 11, 2012".
Hackman, D., "British Medical Journal" 334:163-164 ( 2007).
Gaoni et al., "J. Am. Chem. Soc." 86:1646 ( 1964).
Gomaraschi et al., "Expert Opinion Ther. Targets" 10(4):561-572 ( 2006).
Patani et al., "Chem. Review" 96:3147-3176 ( 1996).
Pertwee et al., "Life Sci." 56(23-24):1949-1955 ( 1995).
Devane et al., "Science" 258:1946-1949 ( 1992).
Porter et al., "Pharmacol. Ther." 90(1):45-60 ( 2001).
Hosohata et al., "Life Sci." 61:115-118 ( 1997).
Ryberg et al., "FEBS Lett." 579:259-264 ( 2005).
Felder et al., "Proc. Natl. Acad. Sci. USA" 90(16):7656-7660 ( 1993).
Pertwee, R. G., "Pharmaceut. Sci." 3(11):539-545 ( 1997).
Pertwee, R. G., "Curr. Med. Chem." 6(8):635-664 ( 1999).
Casiano et al., "Nida Res. Monogr." 105:295-296 ( 1991).
Barth et al., "Cannabinoid Antagonists: From Research Tools to Potential New Drugs." Abstracts of Papers, 222nd ASC National Meeting, Chicago, IL—USA (Aug. 26-30, 2001).
"International Search Report PCT/EP2011/065341 mailed Nov. 28, 2011".
Dimarzo et al., "Nature" 410(6830):822-825 ( 2001).
Felder et al., "J. Pharmacol. Exp. Ther." 284:291-297 ( 1998).
Dimarzo et al., "Trends in Neuroscience" 21(12):521-528 ( 1998).
Hackman, D., "JAMA" 296(14):1731-1732 ( 2006).
Andjelkovic et al., "HCAPLUS: 4410504" ( 2008).
Belsey et al., "Current Med. Res." 24:2703-2709 ( 2008).
Williams et al., "Psychopharmacology" 143(3):315-317 ( 1999).
Colombo et al., "Life Sci." 63(8):L113-L117 ( 1998).
Shire et al., "Journal of Biological Chemistry" 270:3726-3731 ( 1995).
Kanyonyo et al., "Bioorg. Med. Chem. Lett." 9(15):2233-2236 ( 1999).
Jordan et al., "Nature Reviews" 2:2005 ( 2003).
Ooms et al., "J. Med. Chem." 45(9):1748-1756 ( 2002).

N-PYRIDIN-3-YL OR N-PYRAZIN-2-YL CARBOXAMIDES

PRIORITY TO RELATED APPLICATION(S)

This application claims the benefit of European Patent Application No. 10187724.9, filed Oct. 15, 2010, which is hereby incorporated by reference in its entirety.

FIELD OF THE INVENTION

The present invention is concerned with N-pyridin-3-yl or N-pyrazin-2-yl carboxamide compounds being HDL-cholesterol raising agents, their manufacture, pharmaceutical compositions containing them and their use as therapeutically active substances.

BACKGROUND OF THE INVENTION

The compounds of the invention are HDL-cholesterol raising agents and can therefore be used in the therapeutic and/or prophylactic treatment of diseases and disorders such as dyslipidemia, atherosclerosis and cardiovascular diseases.

Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non-esterified cholesterol). There are 3 different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (~10-12%). As a result, there is a significant unmet medical need for a well tolerated agent which can significantly elevate plasma HDL levels.

Thus, HDL-cholesterol raising agents can be useful as medicaments for the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, HDL-cholesterol raising agents may be used in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesteryl ester transfer protein (CETP) inhibitor, a cholesterol absorption inhibitor, a cholesterol synthesis inhibitor, a fibrate, niacin, preparations containing niacin or other HM74a agonists, an ion-exchange resin, an antioxidant, an ACAT inhibitor or a bile acid sequestrant. Object of the present invention is therefore to provide compounds that are potent HDL-cholesterol raising agents. It has been found that the compounds of formula I of the present invention are very useful for the treatment and/or prophylaxis of diseases and disorders which can be treated with HDL-cholesterol raising agents, i.e. the compounds of formula I are especially useful for the treatment and/or prevention of dyslipidemia, atherosclerosis and cardiovascular diseases. Object of the present invention is also to provide compounds which are, at therapeutically active concentrations that increase HDL-concentrations, not interacting with the CB1 receptor. This is because CB1 receptor ligands may compromise the therapeutic utility of HDL-cholesterol raising agents, as both agonists and antagonists of the CB1 receptor have the potential to lead to side effects.

SUMMARY OF THE INVENTION

The present invention relates to compounds according to formula I,

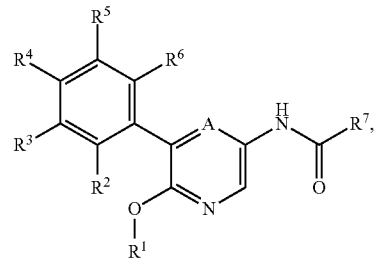

wherein
A is CH or N;
$R^1$ is selected from the group consisting of
  lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen;
$R^2$ and $R^6$ independently from each other are hydrogen or halogen;
$R^3$ and $R^5$ independently from each other are selected from the group consisting of hydrogen, lower alkyl, lower alkoxy, halogen, lower halogenalkyl, lower halogenalkoxy and cyano;
$R^4$ is selected from the group consisting of hydrogen, lower alkyl, lower alkoxy, halogen, lower halogenalkyl, lower halogenalkoxy, amino, azido and cyano; and
$R^7$ is selected from the group consisting of lower alkyl,
  lower hydroxyalkyl, lower alkoxyalkyl,
  lower hydroxyimino-alkyl, lower alkoxyimino-alkyl,
  lower cycloalkyl, said cycloalkyl being unsubstituted or substituted by hydroxy, lower heterocyclyl, phenyl, said phenyl being unsubstituted or substituted by one or two groups selected from the group consisting of lower alkyl, hydroxy, lower alkoxy, cyano, lower alkylaminocarbonyl and halogen, and heteroaryl, said heteroaryl being unsubstituted or substituted by one or two groups selected from the group consisting of lower alkyl, hydroxy, lower alkoxy, cyano, lower alkylaminocarbonyl and halogen.

The present invention also relates to pharmaceutically acceptable salts of the aforementioned compounds.

The present invention further relates to pharmaceutical compositions comprising a compound as described above, or a pharmaceutically acceptable salt thereof, and a pharmaceutically acceptable carrier and/or adjuvant

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven carbon atom(s). In an embodiment, the group consists of one to four carbon atoms.

The term "alkyl", alone or in combination with other groups, refers to a branched or straight-chain monovalent saturated aliphatic hydrocarbon radical of one to twenty carbon atoms, one to sixteen carbon atoms, or one to ten carbon atoms.

The term "lower alkyl" or "$C_{1-7}$-alkyl", alone or in combination, signifies a straight-chain or branched-chain alkyl group with 1 to 7 carbon atoms, for example a straight or branched-chain alkyl group with 1 to 6 carbon atoms or a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls. In an embodiment, the straight-chain and branched $C_{1-7}$ alkyl groups are ethyl, propyl, isopropyl and tert-butyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy. In an embodiment, the lower alkoxy may be methoxy.

The term "lower alkoxyalkyl" or "$C_{1-7}$-alkoxy-$C_{1-7}$-alkyl" refers to a lower alkyl group as defined above which is mono- or multiply substituted with a lower alkoxy group as defined above. Examples of lower alkoxyalkyl groups are e.g. —CH$_2$—O—CH$_3$, —CH$_2$—CH$_2$—O—CH$_3$, —CH$_2$—O—CH$_2$—CH$_3$ and the groups specifically exemplified herein. In an embodiment, the lower alkoxyalkyl is methoxyethyl.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. In an embodiment, the lower hydroxyalkyl is a $C_{3-7}$-hydroxyalkyl group. Examples of lower hydroxyalkyl groups are 2-hydroxybutyl, 3-hydroxy-2,2-dimethylpropyl and the groups specifically exemplified therein.

The term "lower hydroxyimino-alkyl" or "hydroxyimino-$C_{1-7}$-alkyl" refers to lower alkyl groups as defined above wherein at least one of the hydrogen atoms of the lower alkyl group is replaced by a hydroxyimino group (=N—OH). In an embodiment, the lower hydroxyimino-alkyl group is a 1-hydroxyiminoethyl group: —C(=N—OH)—CH$_3$.

The term "lower alkoxyimino-alkyl" or "$C_{1-7}$-alkoxyimino-$C_{1-7}$-alkyl" refers to a lower alkyl group as defined above wherein at least one of the hydrogen atoms of the lower alkyl group is replaced by a lower alkoxyimino group (=N—OR, R=lower alkyl). Examples of lower alkoxyimino-alkyl groups are 1-methoxyiminoethyl or 1-ethoxyiminoethyl. In an embodiment, the lower alkoxyimino-alkyl is 1-methoxyiminoethyl: (—C(=N—OCH$_3$)—CH$_3$).

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. In an embodiment, the cycloalkyl is cyclopropyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by a cycloalkyl group. In an embodiment, the lower cycloalkylalkyl group is cyclopropylmethyl.

The term "halogen" refers to fluoro, chloro, bromo and iodo. In an embodiment, the halogen is selected from the group consisting of fluoro, chloro and bromo. In another embodiment, the halogen is fluoro or chloro.

The term "lower halogenalkyl" or "halogen-$C_{1-7}$-alkyl" refers to lower alkyl groups which are mono- or multiply substituted with halogen, preferably with fluoro or chloro, most preferably with fluoro. Examples of lower halogenalkyl groups are e.g. —CF$_3$, —CHF$_2$, —CH$_2$Cl, —CH$_2$CF$_3$, —CH(CF$_3$)$_2$, —CF$_2$—CF$_3$, —CH$_2$—CH$_2$—CF$_3$, —CH(CH$_3$)—CF$_3$ and the groups specifically exemplified herein. In an embodiment, the lower halogenalkyl is selected from the group consisting of trifluoromethyl (—CF$_3$), 2,2,2-trifluoroethyl (—CH$_2$CF$_3$), and 1,1,1-trifluoro-propan-2-yl (—CH(CH$_3$)—CF$_3$).

The term "lower halogenalkoxy or "halogen-$C_{1-7}$-alkoxy" refers to lower alkoxy groups which are mono- or multiply substituted with halogen, preferably with fluoro or chloro, most preferably with fluoro. Examples of lower halogenalkyl groups are e.g. —OCF$_3$, —OCHF$_2$, —OCH$_2$Cl, —OCH$_2$CF$_3$, —OCH(CF$_3$)$_2$, —OCF$_2$—CF$_3$ and —OCH(CH$_3$)—CF$_3$ The term "cyano" means to group —CN.

The term "amino" refers to the group —NH$_2$.

The term "azido" means the group —N=N$^+$=N$^-$.

The term "carbamoyl" or "aminocarbonyl" refers to the group —CO—NH$_2$.

The term "lower carbamoylalkyl" or "carbamoyl-$C_{1-7}$-alkyl" refers to lower alkyl groups as defined above wherein one of the hydrogen atoms of the lower alkyl group is replaced by a carbamoyl group. Examples of lower carbamoylalkyl groups are 3-carbamoylpropyl, 4-carbamoylbutyl and 5-carbamoylpentyl. In an embodiment, the lower carbamoylalkyl is 4-carbamoylbutyl.

The term "lower alkylcarbonyl" refers to the group —CO—R", wherein R" is lower alkyl as defined herein before. "Lower alkylcarbonylamino" refers to the group —NH—CO—R", wherein R" is lower alkyl as defined herein before.

The term "lower alkylcarbonylaminoalkyl" or "$C_{1-7}$-alkylcarbonylamino-$C_{1-7}$-alkyl" refers to lower alkyl groups as defined above wherein one of the hydrogen atoms of the lower alkyl group is replaced by a lower alkylcarbonylamino group. An example for a lower alkylcarbonylaminoalkyl group is ethylcarbonylaminoethyl.

The term "lower alkylaminocarbonyl" or "$C_{1-7}$-alkylaminocarbonyl" refers to the group —CO—NH—R wherein R is a lower alkyl group as defined above. An example for a lower alkylaminocarbonyl group is methylaminocarbonyl.

The term "lower phenylalkyl" or "phenyl-$C_{1-7}$-alkyl" refers to lower alkyl groups as defined above wherein at least one of the hydrogen atoms of the lower alkyl group is replaced by a phenyl group. In an embodiment, the lower phenylalkyl is benzyl.

The term "heterocyclyl" refers to a saturated or partly unsaturated 3-, 4-, 5-, 6- or 7-membered ring which can comprise one, two or three heteroatoms selected from N, O and S. Examples of heterocyclyl rings include piperidinyl, piperazinyl, azetidinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, oxiranyl, thiadiazolylidinyl, oxetanyl, dioxolanyl, dihydrofuranyl, tetrahydrofuranyl, dihydropyranyl, tetrahydropyranyl, and thiomorpholinyl. In an embodiment of the present invention, the heterocyclyl may be a tetrahydrofuranyl group.

The term "lower heterocyclylalkyl" or "heterocyclyl-$C_{1-7}$-alkyl" refers to lower alkyl groups as defined above wherein at least one of the hydrogen atoms of the lower alkyl group is replaced by a heterocyclyl group as defined above.

The term "heteroaryl" refers to an aromatic 5- or 6-membered ring which can comprise one, two or three atoms selected from N, O and S. Examples of heteroaryl groups are e.g. furanyl, pyridyl, pyrazinyl, pyrimidinyl, pyridazinyl, thienyl, isoxazolyl, thiazolyl, isothiazolyl, thiadiazolyl, oxazolyl, imidazolyl, pyrazolyl, triazolyl, oxadiazolyl, oxatriazolyl, tetrazolyl, pentazolyl, or pyrrolyl. The term "heteroaryl" also includes bicyclic groups comprising two 5- or 6-membered rings, in which one or both rings are aromatic and can contain one, two or three atoms selected from nitrogen, oxygen or sulphur, such as quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl, indazolyl, and 3,4-dihydro-2H-pyrido[3,2-b][1,4]oxazinyl. The heteroaryl group can optionally be mono- or disubstituted by lower alkyl, hydroxy, cyano or halogen. Examples of heteroaryl groups include furanyl, oxazolyl, isoxazolyl, pyrazolyl, thiazolyl, isothiazolyl, [1,2,3]thiadiazolyl, pyridyl, pyrazinyl, pyridazinyl, pyrimidinyl and 3,4-dihydro-2H-pyrido[3,2-b][1,4]oxazinyl.

The term "lower heteroarylalkyl" or "heteroaryl-$C_{1-7}$-alkyl" refers to lower alkyl groups as defined above wherein at least one of the hydrogen atoms of the lower alkyl group is replaced by a heteroaryl group as defined above.

"Isomeric forms" are all forms of a compound characterized by having an identical molecular formula but that differ in the nature or the sequence of bonding of their atoms or in the arrangement of their atoms in space. Preferably, the isomeric forms differ in the arrangement of their atoms in space and can also be termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center".

The term "pharmaceutically acceptable salts" refers to those salts which retain the biological effectiveness and properties of the free bases or free acids, and which do not possess any own properties that are undesirable. The salts are formed with inorganic acids such as hydrochloric acid, hydrobromic acid, sulfuric acid, nitric acid, phosphoric acid and the like, preferably hydrochloric acid, and organic acids such as formic acid, acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. Thus, preferred "pharmaceutically acceptable salts" include the acetate, bromide, chloride, formate, fumarate, maleate, mesylate, nitrate, oxalate, phosphate, sulfate, tartrate and tosylate salt of compounds of formula I. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, diethylamine, lysine, arginine, N-ethylpiperidine, piperidine, piperazine and the like. The compound of formula I can also be present in the form of zwitterions or in the form of hydrates. In an embodiment of the present invention, the pharmaceutically acceptable salts of compounds of formula I are the hydrochloride salts.

The present invention relates to compounds of formula I,

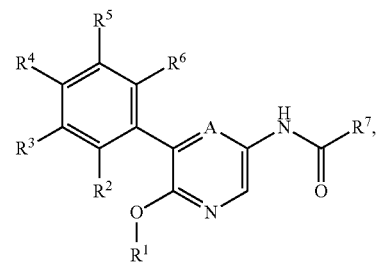

wherein

A is CH or N;

$R^1$ is selected from the group consisting of
  lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen;

$R^2$ and $R^6$ independently from each other are hydrogen or halogen;

$R^3$ and $R^5$ independently from each other are selected from the group consisting of hydrogen, lower alkyl, lower alkoxy, halogen, lower halogenalkyl, lower halogenalkoxy and cyano;

$R^4$ is selected from the group consisting of hydrogen, lower alkyl, lower alkoxy, halogen, lower halogenalkyl, lower halogenalkoxy, amino, azido and cyano; and $R^7$ is selected from the group consisting of lower alkyl, lower hydroxyalkyl, lower alkoxyalkyl, lower hydroxyimino-alkyl, lower alkoxyimino-alkyl, lower cycloalkyl, said cycloalkyl being unsubstituted or substituted by hydroxy, lower heterocyclyl, phenyl, said phenyl being unsubstituted or substituted by one or two groups selected from the group consisting of lower alkyl, hydroxy, lower alkoxy, cyano, lower alkylaminocarbonyl and halogen, heteroaryl, said heteroaryl being unsubstituted or substituted by one or two groups selected from the group consisting of lower alkyl, hydroxy, lower alkoxy, cyano, lower alkylaminocarbonyl and halogen;

and pharmaceutically acceptable salts thereof.

Compounds of formula I of the present invention are those, wherein $R^1$ is selected from the group consisting of lower alkyl, cycloalkyl, lower cycloalkylalkyl, lower hydroxyalkyl, lower alkoxyalkyl, lower halogenalkyl, lower carbamoylalkyl, lower alkylcarbonylaminoalkyl, lower phenylalkyl, lower heterocyclylalkyl wherein the heterocyclyl group is unsubstituted or substituted by oxo, and lower heteroarylalkyl wherein the heteroaryl group is unsubstituted or mono- or di-substituted by lower alkyl.

In an embodiment, the invention relates to compounds of formula I, wherein $R^1$ is selected from the group consisting of cycloalkyl, lower cycloalkylalkyl, lower alkoxyalkyl and lower halogenalkyl. In an embodiment, $R^1$ is selected from the group consisting of cyclobutyl, cyclopropylmethyl, 2-methoxyethyl and lower halogenalkyl. In an embodiment, $R^1$ is cyclopropylmethyl or lower halogenalkyl. In an embodiment, $R^1$ is lower halogenalkyl. In an embodiment, $R^1$ is 2,2,2-trifluoroethyl or 1,1,1-trifluoro-propan-2-yl. In an embodiment $R^1$ is 2,2,2-trifluoroethyl.

Compounds of formula I of the invention are those, wherein $R^2$ and $R^6$ are independently from each other hydrogen or halogen. In an embodiment, the compounds are those wherein $R^2$ and $R^6$ are hydrogen.

The invention further relates to compounds of formula I, wherein $R^3$ and $R^5$ are independently from each other selected from the group consisting of hydrogen, lower alkyl, lower alkoxy, halogen, lower halogenalkyl, lower halogenalkoxy and cyano. In an embodiment, the invention relates to compounds of formula I wherein $R^3$ and $R^5$ are independently selected from hydrogen, halogen and lower alkyl, for example hydrogen, fluoro, chloro and methyl. In an embodiment, the invention relates to compounds of formula I wherein $R^3$ and $R^5$ are each independently hydrogen or lower alkyl.

Furthermore, the invention is concerned with compounds of formula I, wherein $R^4$ is selected from the group consisting of hydrogen, lower alkyl, lower alkoxy, halogen, lower halogenalkyl, lower halogenalkoxy, amino, azido and cyano. In an embodiment, $R^4$ is lower alkyl or halogen. In an embodiment, $R^4$ is halogen, for example chloro.

Compounds of formula I of the invention are further those, wherein $R^7$ is selected from the group consisting of lower alkyl, lower hydroxyalkyl, lower alkoxyalkyl, lower hydroxyimino-alkyl, lower alkoxyimino-alkyl, lower cycloalkyl, said cycloalkyl being unsubstituted or substituted by hydroxy, lower heterocyclyl, phenyl, said phenyl being unsubstituted or substituted by one or two groups selected from the group consisting of lower alkyl, hydroxy, lower alkoxy, cyano, lower alkylaminocarbonyl and halogen, and heteroaryl, said heteroaryl being unsubstituted or substituted by one or two groups selected from the group consisting of lower alkyl, hydroxy, lower alkoxy, cyano, lower alkylaminocarbonyl and halogen.

One group of compounds of formula I of the invention are those wherein $R^7$ is lower alkyl, for example methyl, propyl or butyl.

Another group of compounds of formula I of the present invention are those wherein $R^7$ is phenyl, said phenyl being unsubstituted or substituted by one or two groups selected from the group of lower alkyl, hydroxy, lower alkoxy, cyano, lower alkylaminocarbonyl and halogen, or heteroaryl, said heteroaryl being unsubstituted or substituted by one or two groups selected from the group consisting of lower alkyl, hydroxy, lower alkoxy, cyano, lower alkylaminocarbonyl and halogen.

Another group of compounds of formula I of the present invention are those wherein $R^7$ is phenyl, said phenyl being unsubstituted or substituted by one or two groups selected from the group of lower alkyl, hydroxy, cyano, lower alkylaminocarbonyl and halogen, or heteroaryl, said heteroaryl being unsubstituted or substituted by one or two groups selected from the group consisting of lower alkyl, hydroxy, cyano, lower alkylaminocarbonyl and halogen.

In an embodiment, the compounds of the present invention are compounds of formula I according to the invention, wherein $R^7$ is heteroaryl, said heteroaryl being unsubstituted or substituted by one or two groups selected from the group consisting of lower alkyl, hydroxy, lower alkoxy, cyano, lower alkylaminocarbonyl and halogen. In an embodiment, the invention relates to compounds of formula I wherein $R^7$ is heteroaryl, said heteroaryl being unsubstituted or substituted by one or two groups selected from the group consisting of lower alkyl, hydroxy, cyano, lower alkylaminocarbonyl and halogen. In an embodiment, the invention relates to compounds of formula I wherein $R^7$ is heteroaryl selected from the group consisting of furanyl, oxazolyl, isoxazolyl, pyrazolyl, thiazolyl, isothiazolyl, [1,2,3]thiadiazolyl, pyridyl, pyrazinyl, pyridazinyl, pyrimidinyl and 3,4-dihydro-2H-pyrido[3,2-b][1,4]oxazinyl, said heteroaryl being unsubstituted or substituted by one or two groups selected from the group consisting of lower alkyl, hydroxy, lower alkoxy, cyano, lower alkylaminocarbonyl and halogen. In an embodiment, the invention relates to compounds of formula I wherein $R^7$ is heteroaryl selected from the group consisting of furanyl, oxazolyl, isoxazolyl, pyrazolyl, thiazolyl, isothiazolyl, [1,2,3]thiadiazolyl, pyridyl, pyrazinyl, pyridazinyl, pyrimidinyl and 3,4-dihydro-2H-pyrido[3,2-b][1,4]oxazinyl, said heteroaryl being unsubstituted or substituted by one or two groups selected from the group consisting of lower alkyl, hydroxy, cyano, lower alkylaminocarbonyl and halogen. In an embodiment, $R^7$ is heteroaryl selected from the group consisting of oxazolyl, isoxazolyl, pyrazolyl, pyridyl, pyridazinyl and pyrimidinyl, said heteroaryl being unsubstituted or substituted by one or two groups selected from the group consisting of lower alkyl, hydroxy, lower alkoxy, cyano, lower alkylaminocarbonyl and halogen. In an embodiment, $R^7$ is pyridyl, said pyridyl being unsubstituted or substituted by one or two groups selected from the group consisting of lower alkyl, hydroxy, lower alkoxy, cyano, lower alkylaminocarbonyl and halogen.

In an embodiment, the invention relates to compounds of formula I, wherein $R^7$ is selected from the group consisting of furan-2-yl, 5-methyl-furan-2-yl, furan-3-yl, 5-methyl-oxazol-4-yl, 2,4-dimethyl-oxazol-5-yl, isoxazol-5-yl, 3-methyl-isoxazol-4-yl, 3,5-dimethyl-isoxazol-4-yl, 5-methyl-isoxazol-3-yl, 1H-pyrazol-3-yl, 1-methyl-1H-pyrazol-3-yl, 1,3-dimethyl-1H-pyrazol-4-yl, 2-methyl-2H-pyrazol-3-yl, 5-methyl-2H-pyrazol-3-yl, 2,5-dimethyl-2H-pyrazol-3-yl, thiazol-2-yl, 5-methyl-thiazol-2-yl, isothiazol-5-yl, 4-methyl-[1,2,3]thiadiazol-5-yl, pyridin-2-yl, 3-methylpyridin-2-yl, pyridin-3-yl, 2,4-difluoro-pyridin-3-yl, 2-methyl-pyridin-3-yl, 5-methyl-pyridin-3-yl, 6-methyl-pyridin-3-yl, 5-cyano-pyridin-3-yl, 5-bromo-pyridin-3-yl, 5-iodo-pyridin-3-yl, 5-methoxy-pyridin-3-yl, pyridin-4-yl, 2-methyl-pyridin-4-yl, 3-methyl-pyridin-4-yl, 2-hydroxy-pyridin-4-yl, 5-hydroxy-pyridin-2-yl, pyrazin-2-yl, pyridazin-3-yl, pyrimidin-4-yl, pyrimidin-5-yl and 4-methyl-3,4-dihydro-2H-pyrido[3,2-b][1,4]oxazin-7-yl. In an embodiment, $R^7$ is selected from the group consisting of pyridin-3-yl, 3-methyl-isoxazol-4-yl, pyridazin-3-yl, 1,3-dimethyl-1H-pyrazol-4-yl and 5-methyl-oxazol-4-yl. In an embodiment, $R^7$ is pyridin-3-yl.

In an embodiment, the invention relates to compounds of formula I, wherein A is CH. These are the pyridine derivatives of formula I-A,

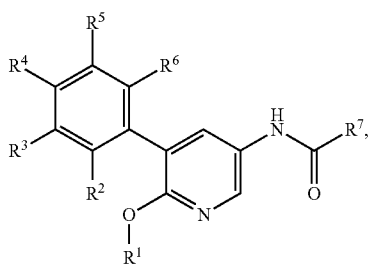

I-A wherein
$R^1$ is selected from the group consisting of
  lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen;
$R^2$ and $R^6$ independently from each other are hydrogen or halogen;
$R^3$ and $R^5$ independently from each other are selected from the group consisting of hydrogen, lower alkyl, lower alkoxy, halogen, lower halogenalkyl, lower halogenalkoxy and cyano;
$R^4$ is selected from the group consisting of hydrogen, lower alkyl, lower alkoxy, halogen, lower halogenalkyl, lower halogenalkoxy, amino, azido and cyano; and
$R^7$ is selected from the group consisting of
  lower alkyl,
  lower hydroxyalkyl, lower alkoxyalkyl,
  lower hydroxyimino-alkyl, lower alkoxyimino-alkyl,
  lower cycloalkyl, said cycloalkyl being unsubstituted or substituted by hydroxy,
  lower heterocyclyl,
  phenyl, said phenyl being unsubstituted or substituted by one or two groups selected from the group consisting of lower alkyl, hydroxy, lower alkoxy, cyano, lower alkylaminocarbonyl and halogen,
  heteroaryl, said heteroaryl being unsubstituted or substituted by one or two groups selected from the group consisting of lower alkyl, hydroxy, lower alkoxy, cyano, lower alkylaminocarbonyl and halogen;
or a pharmaceutically acceptable salt thereof.

In an embodiment, the present invention relates to compounds of formula I-AA,

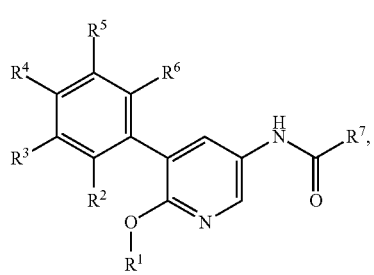

I-AA wherein
$R^1$ is selected from the group consisting of
  lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen;
$R^2$ and $R^6$ independently from each other are hydrogen or halogen;
$R^3$ and $R^5$ independently from each other are selected from the group consisting of hydrogen, lower alkyl, lower alkoxy, halogen, lower halogenalkyl, lower halogenalkoxy and cyano;
$R^4$ is selected from the group consisting of hydrogen, lower alkoxy, halogen, lower halogenalkyl, lower halogenalkoxy, amino, azido and cyano; and
$R^7$ is selected from the group consisting of
  lower alkyl,
  lower hydroxyalkyl,
  lower cycloalkyl, said cycloalkyl being unsubstituted or substituted by hydroxy, lower heterocyclyl,
  phenyl, said phenyl being unsubstituted or substituted by one or two groups selected from the group consisting of lower alkyl, hydroxy and halogen,
  heteroaryl, said heteroaryl being unsubstituted or substituted by one or two groups selected from the group consisting of lower alkyl, hydroxy, cyano and halogen;
or a pharmaceutically acceptable salt thereof.

The invention also relates to compounds of formula I, wherein A is N. These are the pyrazine derivatives of formula I-B,

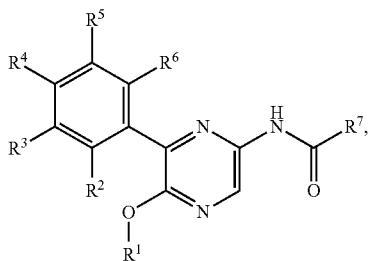

wherein
R¹ is selected from the group consisting of
  lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen;
R² and R⁶ independently from each other are hydrogen or halogen;
R³ and R⁵ independently from each other are selected from the group consisting of hydrogen, lower alkyl, lower alkoxy, halogen, lower halogenalkyl, lower halogenalkoxy and cyano;
R⁴ is selected from the group consisting of hydrogen, lower alkyl, lower alkoxy, halogen, lower halogenalkyl, lower halogenalkoxy, amino, azido and cyano; and
R⁷ is selected from the group consisting of
  lower alkyl,
  lower hydroxyalkyl, lower alkoxyalkyl,
  lower hydroxyimino-alkyl, lower alkoxyimino-alkyl,
  lower cycloalkyl, said cycloalkyl being unsubstituted or substituted by hydroxy,
  lower heterocyclyl,
  phenyl, said phenyl being unsubstituted or substituted by one or two groups selected from the group consisting of lower alkyl, hydroxy, lower alkoxy, cyano, lower alkylaminocarbonyl and halogen,
  heteroaryl, said heteroaryl being unsubstituted or substituted by one or two groups selected from the group consisting of lower alkyl, hydroxy, lower alkoxy, cyano, lower alkylaminocarbonyl and halogen;
or a pharmaceutically acceptable salt thereof.

Examples of compounds of formula I of the present invention are the following:
pentanoic acid[5-(4-chloro-phenyl)-6-(2,2,2-trifluoro-ethoxy)-pyridin-3-yl]-amide,
N-[5-(4-chloro-phenyl)-6-(2,2,2-trifluoro-ethoxy)-pyridin-3-yl]-benzamide,
N-[5-(4-chloro-phenyl)-6-(2,2,2-trifluoro-ethoxy)-pyridin-3-yl]-nicotinamide,
N-[5-(4-chloro-phenyl)-6-(2,2,2-trifluoro-ethoxy)-pyridin-3-yl]-isonicotinamide,
N-[5-(4-chloro-phenyl)-6-(2,2,2-trifluoro-ethoxy)-pyridin-3-yl]-acetamide,
N-[5-(4-chloro-phenyl)-6-(2,2,2-trifluoro-ethoxy)-pyridin-3-yl]-butyramide,
pyridine-2-carboxylic acid[5-(4-chloro-phenyl)-6-(2,2,2-trifluoro-ethoxy)-pyridin-3-yl]-amide,
N-[5-(4-chloro-phenyl)-6-cyclopropylmethoxy-pyridin-3-yl]-benzamide,
N-[5-(4-chloro-phenyl)-6-cyclopropylmethoxy-pyridin-3-yl]-acetamide,
N-[5-(4-chloro-phenyl)-6-cyclopropylmethoxy-pyridin-3-yl]-nicotinamide,
N-[5-(4-chloro-phenyl)-6-cyclopropylmethoxy-pyridin-3-yl]-isonicotinamide,
pyrazine-2-carboxylic acid[5-(4-chloro-phenyl)-6-(2,2,2-trifluoro-ethoxy)-pyridin-3-yl]-amide,
2,5-dimethyl-2H-pyrazole-3-carboxylic acid[5-(4-chloro-phenyl)-6-(2,2,2-trifluoro-ethoxy)-pyridin-3-yl]-amide,
3-methyl-isoxazole-4-carboxylic acid[5-(4-chloro-phenyl)-6-(2,2,2-trifluoro-ethoxy)-pyridin-3-yl]-amide,
1-methyl-1H-pyrazole-3-carboxylic acid[5-(4-chloro-phenyl)-6-(2,2,2-trifluoro-ethoxy)-pyridin-3-yl]-amide,
5-methyl-isoxazole-3-carboxylic acid[5-(4-chloro-phenyl)-6-(2,2,2-trifluoro-ethoxy)-pyridin-3-yl]-amide,
pyridazine-3-carboxylic acid[5-(4-chloro-phenyl)-6-(2,2,2-trifluoro-ethoxy)-pyridin-3-yl]-amide,
N-[5-(4-chloro-phenyl)-6-(2,2,2-trifluoro-ethoxy)-pyridin-3-yl]-3-methyl-isonicotinamide,
pyrimidine-5-carboxylic acid[5-(4-chloro-phenyl)-6-(2,2,2-trifluoro-ethoxy)-pyridin-3-yl]-amide,
2-methyl-2H-pyrazole-3-carboxylic acid[5-(4-chloro-phenyl)-6-(2,2,2-trifluoro-ethoxy)-pyridin-3-yl]-amide,
2,4-dimethyl-oxazole-5-carboxylic acid[5-(4-chloro-phenyl)-6-(2,2,2-trifluoro-ethoxy)-pyridin-3-yl]-amide,
isothiazole-5-carboxylic acid[5-(4-chloro-phenyl)-6-(2,2,2-trifluoro-ethoxy)-pyridin-3-yl]-amide,
5-methyl-2H-pyrazole-3-carboxylic acid[5-(4-chloro-phenyl)-6-(2,2,2-trifluoro-ethoxy)-pyridin-3-yl]-amide,
1H-pyrazole-3-carboxylic acid[5-(4-chloro-phenyl)-6-(2,2,2-trifluoro-ethoxy)-pyridin-3-yl]-amide,
N-[5-(4-chloro-phenyl)-6-(2,2,2-trifluoro-ethoxy)-pyridin-3-yl]-2-methyl-isonicotinamide,
5-methyl-thiazole-2-carboxylic acid[5-(4-chloro-phenyl)-6-(2,2,2-trifluoro-ethoxy)-pyridin-3-yl]-amide,
4-methyl-[1,2,3]thiadiazole-5-carboxylic acid[5-(4-chloro-phenyl)-6-(2,2,2-trifluoro-ethoxy)-pyridin-3-yl]-amide,
N-[5-(4-chloro-phenyl)-6-(2,2,2-trifluoro-ethoxy)-pyridin-3-yl]-6-methyl-nicotinamide,
N-[5-(4-chloro-phenyl)-6-(2,2,2-trifluoro-ethoxy)-pyridin-3-yl]-2-methyl-nicotinamide,
isoxazole-5-carboxylic acid[5-(4-chloro-phenyl)-6-(2,2,2-trifluoro-ethoxy)-pyridin-3-yl]-amide,
3,5-dimethyl-isoxazole-4-carboxylic acid[5-(4-chloro-phenyl)-6-(2,2,2-trifluoro-ethoxy)-pyridin-3-yl]-amide,
N-[5-(4-chloro-phenyl)-6-(2,2,2-trifluoro-ethoxy)-pyridin-3-yl]-2-hydroxy-isonicotinamide,
1,3-dimethyl-1H-pyrazole-4-carboxylic acid[5-(4-chloro-phenyl)-6-(2,2,2-trifluoro-ethoxy)-pyridin-3-yl]-amide,
pyrimidine-4-carboxylic acid[5-(4-chloro-phenyl)-6-(2,2,2-trifluoro-ethoxy)-pyridin-3-yl]-amide,
thiazole-2-carboxylic acid[5-(4-chloro-phenyl)-6-(2,2,2-trifluoro-ethoxy)-pyridin-3-yl]-amide,
3-methyl-pyridine-2-carboxylic acid[5-(4-chloro-phenyl)-6-(2,2,2-trifluoro-ethoxy)-pyridin-3-yl]-amide,
5-methyl-oxazole-4-carboxylic acid[5-(4-chloro-phenyl)-6-(2,2,2-trifluoro-ethoxy)-pyridin-3-yl]-amide, N-(5-(3,4-dimethylphenyl)-6-(2,2,2-trifluoroethoxy)pyridin-3-yl)-nicotinamide,
N-(5-(4-chloro-3-methylphenyl)-6-(2,2,2-trifluoroethoxy)pyridin-3-yl)-nicotinamide,
and pharmaceutically acceptable salts thereof.
Further compounds of formula I of the present invention are the following:
5-hydroxy-pyridine-2-carboxylic acid[5-(4-chloro-phenyl)-6-(2,2,2-trifluoro-ethoxy)-pyridin-3-yl]-amide,
N-(5-(4-chlorophenyl)-6-(2,2,2-trifluoroethoxy)pyridin-3-yl)-5-methylnicotinamide,
(S)-N-(5-(4-chlorophenyl)-6-(1,1,1-trifluoropropan-2-yloxy)pyridin-3-yl)pyridazine-3-carboxamide,
(S)-N-(5-(4-chlorophenyl)-6-(1,1,1-trifluoropropan-2-yloxy)pyridin-3-yl)nicotinamide,
N-(5-(4-chloro-3-fluorophenyl)-6-(2,2,2-trifluoroethoxy)pyridin-3-yl)nicotinamide,
N-(5-(3-chloro-4-fluorophenyl)-6-(2,2,2-trifluoroethoxy)pyridin-3-yl)nicotinamide,
N-(5-(4-chloro-2-fluorophenyl)-6-(2,2,2-trifluoroethoxy)pyridin-3-yl)nicotinamide,
N-(5-(4-ethylphenyl)-6-(2,2,2-trifluoroethoxy)pyridin-3-yl)nicotinamide,
(S)-N-(6-(4-chlorophenyl)-5-(1,1,1-trifluoropropan-2-yloxy)pyrazin-2-yl)nicotinamide,
N-(6-(4-chlorophenyl)-5-(2,2,2-trifluoroethoxy)pyrazin-2-yl)nicotinamide,
N-(6-(4-chlorophenyl)-5-cyclobutoxypyrazin-2-yl)nicotinamide,
N-(6-(4-chlorophenyl)-5-cyclobutoxypyrazin-2-yl)pyrimidine-5-carboxamide,
N-(5-(4-chloro-3-methylphenyl)-6-(2,2,2-trifluoroethoxy)pyridin-3-yl)pyrimidine-5-carboxamide,
N-(5-(4-chloro-3-fluorophenyl)-6-(2,2,2-trifluoroethoxy)pyridin-3-yl)pyrimidine-5-carboxamide,
N-(5-(3-chloro-4-fluorophenyl)-6-(2,2,2-trifluoroethoxy)pyridin-3-yl)pyrimidine-5-carboxamide,
N-(5-(4-chloro-2-fluorophenyl)-6-(2,2,2-trifluoroethoxy)pyridin-3-yl)pyrimidine-5-carboxamide,
N-(5-(4-ethylphenyl)-6-(2,2,2-trifluoroethoxy)pyridin-3-yl)pyrimidine-5-carboxamide,
N-(5-(4-chloro-3-methylphenyl)-6-(2,2,2-trifluoroethoxy)pyridin-3-yl)-2-hydroxyisonicotinamide,
N-(5-(4-chloro-3-methylphenyl)-6-(2,2,2-trifluoroethoxy)pyridin-3-yl)-1,3-dimethyl-1H-pyrazole-4-carboxamide,
N-(5-(4-chloro-3-methylphenyl)-6-(2,2,2-trifluoroethoxy)pyridin-3-yl)-2,4-difluoronicotinamide,
N-(5-(4-chlorophenyl)-6-(2,2,2-trifluoroethoxy)pyridin-3-yl)-2-hydroxybenzamide,
N-(5-(4-chloro-3-methylphenyl)-6-(2,2,2-trifluoroethoxy)pyridin-3-yl)-5-cyanonicotinamide,
N-(5-(4-chloro-3-methylphenyl)-6-(2,2,2-trifluoroethoxy)pyridin-3-yl)pyridazine-3-carboxamide,
N-(5-(4-chloro-3-fluorophenyl)-6-(2,2,2-trifluoroethoxy)pyridin-3-yl)pyridazine-3-carboxamide,
N-(5-(4-chloro-2-fluorophenyl)-6-(2,2,2-trifluoroethoxy)pyridin-3-yl)pyridazine-3-carboxamide,
N-(5-(4-ethylphenyl)-6-(2,2,2-trifluoroethoxy)pyridin-3-yl)pyridazine-3-carboxamide,
N-(5-(4-chlorophenyl)-6-(2,2,2-trifluoroethoxy)pyridin-3-yl)furan-2-carboxamide,
N-(5-(4-chlorophenyl)-6-(2,2,2-trifluoroethoxy)pyridin-3-yl)furan-3-carboxamide,
N-(5-(4-chlorophenyl)-6-(2,2,2-trifluoroethoxy)pyridin-3-yl)-5-methylfuran-2-carboxamide,
N-(5-(4-chloro-3-methylphenyl)-6-(2-methoxyethoxy)pyridin-3-yl)benzamide,
(R)-N-(5-(4-chlorophenyl)-6-(2,2,2-trifluoroethoxy)pyridin-3-yl)tetrahydrofuran-2-carboxamide,
(S)-N-(5-(4-chlorophenyl)-6-(2,2,2-trifluoroethoxy)pyridin-3-yl)tetrahydrofuran-3-carboxamide,
N-(5-(4-chlorophenyl)-6-(2,2,2-trifluoroethoxy)pyridin-3-yl)-4-methyl-3,4-dihydro-2H-pyrido[3,2-b][1,4]oxazine-7-carboxamide,
N-(5-(4-amino-3-chlorophenyl)-6-(2,2,2-trifluoroethoxy)pyridin-3-yl)-5-iodonicotinamide,
N-(5-phenyl-6-(2,2,2-trifluoroethoxy)pyridin-3-yl)nicotinamide,
N-(5-(4-fluorophenyl)-6-(2,2,2-trifluoroethoxy)pyridin-3-yl)nicotinamide,
N-(5-(3-chlorophenyl)-6-(2,2,2-trifluoroethoxy)pyridin-3-yl)nicotinamide,
N-(5-(4-chlorophenyl)-6-(2,2,2-trifluoroethoxy)pyridin-3-yl)-5-methoxynicotinamide,
N-(5-(4-chlorophenyl)-6-cyclobutoxypyridin-3-yl)pyrazine-2-carboxamide,
N-(5-(4-chlorophenyl)-6-cyclobutoxypyridin-3-yl)nicotinamide,
N-(5-(4-chloro-3-methylphenyl)-6-(2,2,2-trifluoroethoxy)pyridin-3-yl)-4-methyl-3,4-dihydro-2H-pyrido[3,2-b][1,4]oxazine-7-carboxamide,
N-(5-(4-chloro-3-fluorophenyl)-6-(2,2,2-trifluoroethoxy)pyridin-3-yl)-4-methyl-3,4-dihydro-2H-pyrido[3,2-b][1,4]oxazine-7-carboxamide,
5-methyl-oxazole-4-carboxylic acid[5-(4-chloro-phenyl)-6-cyclobutoxy-pyridin-3-yl]-amide
N-[5-(4-Chloro-phenyl)-6-cyclobutoxy-pyridin-3-yl]-5-methyl-nicotinamide,
N5-(5-(4-chlorophenyl)-6-(2,2,2-trifluoroethoxy)pyridin-3-yl)-N2-methylpyridine-2,5-dicarboxamide,
5-bromo-N-(5-(4-chlorophenyl)-6-(2,2,2-trifluoroethoxy)pyridin-3-yl)nicotinamide,
N-(5-(4-chlorophenyl)-6-(2,2,2-trifluoroethoxy)pyridin-3-yl)-2-methoxypropanamide,
N3-(5-(4-chlorophenyl)-6-(2,2,2-trifluoroethoxy)pyridin-3-yl)-N5-methylpyridine-3,5-dicarboxamide,
(+)-N-(5-(4-chlorophenyl)-6-(2,2,2-trifluoroethoxy)pyridin-3-yl)-2-methoxypropanamide,
(E)-N-(5-(4-chlorophenyl)-6-(2,2,2-trifluoroethoxy)pyridin-3-yl)-2-(methoxyimino)propanamide,
and pharmaceutically acceptable salts thereof.
In an embodiment, the present invention relates to compounds selected from the group consisting of
N-[5-(4-chloro-phenyl)-6-(2,2,2-trifluoro-ethoxy)-pyridin-3-yl]-nicotinamide,
N-[5-(4-chloro-phenyl)-6-cyclopropylmethoxy-pyridin-3-yl]-nicotinamide,
3-methyl-isoxazole-4-carboxylic acid[5-(4-chloro-phenyl)-6-(2,2,2-trifluoro-ethoxy)-pyridin-3-yl]-amide,
pyridazine-3-carboxylic acid[5-(4-chloro-phenyl)-6-(2,2,2-trifluoro-ethoxy)-pyridin-3-yl]-amide,
1,3-dimethyl-1H-pyrazole-4-carboxylic acid[5-(4-chloro-phenyl)-6-(2,2,2-trifluoro-ethoxy)-pyridin-3-yl]-amide,
5-methyl-oxazole-4-carboxylic acid[5-(4-chloro-phenyl)-6-(2,2,2-trifluoro-ethoxy)-pyridin-3-yl]-amide,
N-(5-(4-chloro-3-methylphenyl)-6-(2,2,2-trifluoroethoxy)pyridin-3-yl)-nicotinamide,
N-(5-(4-chloro-3-fluorophenyl)-6-(2,2,2-trifluoroethoxy)pyridin-3-yl)nicotinamide,
(S)-N-(6-(4-chlorophenyl)-5-(1,1,1-trifluoropropan-2-yloxy)pyrazin-2-yl)nicotinamide,
N-(6-(4-chlorophenyl)-5-cyclobutoxypyrazin-2-yl)pyrimidine-5-carboxamide, N-(5-(4-chloro-2-fluorophenyl)-6-(2,2,2-trifluoroethoxy)pyridin-3-yl)pyrimidine-5-carboxamide,
N-(5-(4-chlorophenyl)-6-(2,2,2-trifluoroethoxy)pyridin-3-yl)-2-hydroxybenzamide,
N-(5-(4-chloro-3-methylphenyl)-6-(2,2,2-trifluoroethoxy)pyridin-3-yl)-5-cyanonicotinamide,
N-(5-(4-chloro-2-fluorophenyl)-6-(2,2,2-trifluoroethoxy)pyridin-3-yl)pyridazine-3-carboxamide,
N-(5-(4-chlorophenyl)-6-(2,2,2-trifluoroethoxy)pyridin-3-yl)-5-methylfuran-2-carboxamide,
N-(5-(4-chlorophenyl)-6-(2,2,2-trifluoroethoxy)pyridin-3-yl)-4-methyl-3,4-dihydro-2H-pyrido[3,2-b][1,4]oxazine-7-carboxamide,
N-(5-(4-chlorophenyl)-6-(2,2,2-trifluoroethoxy)pyridin-3-yl)-5-methoxynicotinamide,
N-(5-(4-chlorophenyl)-6-(2,2,2-trifluoroethoxy)pyridin-3-yl)-2-methoxypropanamide,
and pharmaceutically acceptable salts thereof.

In an embodiment, the invention relates to a compound of formula I, which is N-[5-(4-chloro-phenyl)-6-(2,2,2-trifluoro-ethoxy)-pyridin-3-yl]-nicotinamide, and pharmaceutically acceptable salts thereof.

In an embodiment, the invention relates to a compound of formula I, which is N-[5-(4-chloro-phenyl)-6-cyclopropylmethoxy-pyridin-3-yl]-nicotinamide, and pharmaceutically acceptable salts thereof.

In an embodiment, the invention relates to a compound of formula I, which is N-(5-(4-chlorophenyl)-6-(2,2,2-trifluoroethoxy)pyridin-3-yl)-5-methoxynicotinamide, and pharmaceutically acceptable salts thereof.

The compounds of formula I can be prepared by a process, which process comprises coupling a compound of formula II,

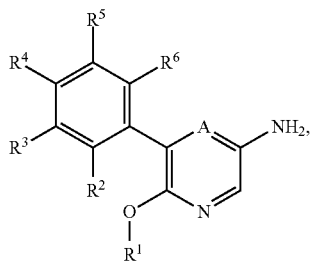

II wherein A and $R^1$ to $R^6$ are as defined herein before, with an acid of formula III,

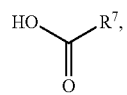

III wherein $R^7$ is as defined herein before, with the help of a coupling agent under basic conditions, and, if desired, converting the resulting compound of formula I into a pharmaceutically acceptable salt thereof.

Coupling agents for the reaction of compounds of formula II with acids of formula III are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), or O-benzotriazole-N,N,N',N'-tetramethyl-uronium-hexafluoro-phosphate (HBTU). More particularly, the coupling agent is HBTU. Suitable bases include triethylamine, diisopropylethylamine and, particularly, N-methylmorpholine.

The synthesis of the compounds with the general structure I-A can be accomplished according to scheme 1.

Following the procedure according to scheme 1, compound AA (3-bromo-2-chloro-5-nitro-pyridine, CAS RN 5470-17-7) can be used as starting material. AA is commercially available.

Compound AB can be prepared from AA by reaction with a suitably substituted primary or secondary alcohol $R^1$—OH in the presence of a base, for example sodium hydride, with or without an inert solvent, for example dimethylformamide, at temperatures from room temperature to reflux temperature of the solvent, preferably at room temperature.

Compound AC can be prepared from AB by reduction using the vast array of possibilities known in the art for reducing the aromatic nitro group. A convenient reduction method is the use of stannous chloride in a suitable solvent mixture, preferably in ethanol with added hydrochloric acid, at temperatures from room temperature to elevated temperatures, preferably at 25° C.

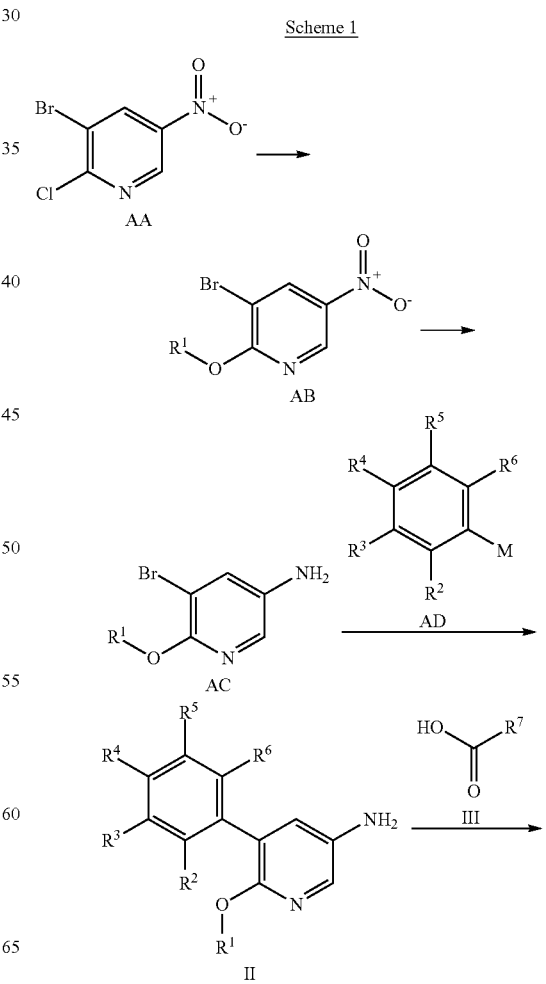

Scheme 1

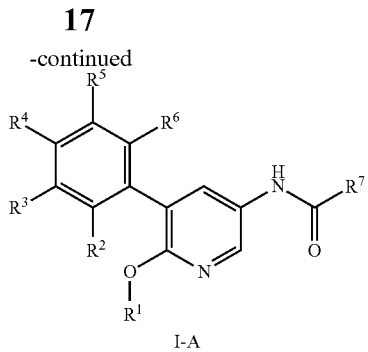

I-A

Compound II can be prepared from AC by coupling a suitably substituted aryl metal species of formula AD, particularly an arylboronic acid or arylboronic acid ester in the presence of a suitable catalyst, in particular a palladium catalyst and more particularly palladium(II) acetate/triphenylphosphine mixtures or palladium(II)chloride-dppf (1,1'-bis(diphenyl-phosphino)ferrocene) complexes and a base such as triethylamine, sodium carbonate or potassium phosphate in an inert solvent such as dimethylformamide, toluene, tetrahydrofuran, acetonitrile and dimethoxyethane.

Compounds of formula AD containing functional groups detrimental to palladium catalyzed Suzuki reactions can for the purpose of carrying out this reaction be protected with a suitable protecting group (P). Suitable amine protecting groups are for example benzyloxy-carbonyl (Z), t-butyloxycarbonyl (BOC), while suitable acid protecting groups are for example benzyl (Bn), benzyloxymethyl (BOM), methoxyethoxymethyl (MEM) or allyl groups and silyl groups such as trimethylsilyl, triethylsilyl and tert-butyldimethylsilyl esters (for more details see T. W. Greene et al., Protective Groups in Organic Chemistry, John Wiley and Sons Inc. New York 1999, 3$^{rd}$ edition). Protecting group removal can be carried out by suitable methods known in the art.

Compound I-A can be prepared from II and the corresponding acid of formula III by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature.

Following the alternative procedure according to scheme 2, compound AC can be used as starting material.

Compound BD can be prepared from AC and the corresponding acid of formula III by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N,N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature.

Compound I-A can be prepared from BD by coupling a suitably substituted aryl metal species of formula AD, particularly an arylboronic acid or arylboronic acid ester in the presence of a suitable catalyst, in particular a palladium catalyst and more particularly palladium(II) acetate/triphenylphosphine mixtures or palladium(II)chloride-dppf (1,1'-bis(diphenyl-phosphino)ferrocene) complexes and a base such as triethylamine, sodium carbonate or potassium phosphate in an inert solvent such as dimethylformamide, toluene, tetrahydrofuran, acetonitrile and dimethoxyethane.

Scheme 2

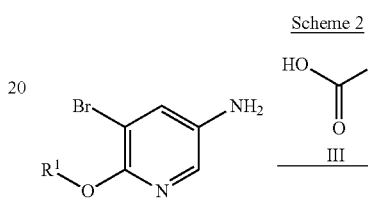

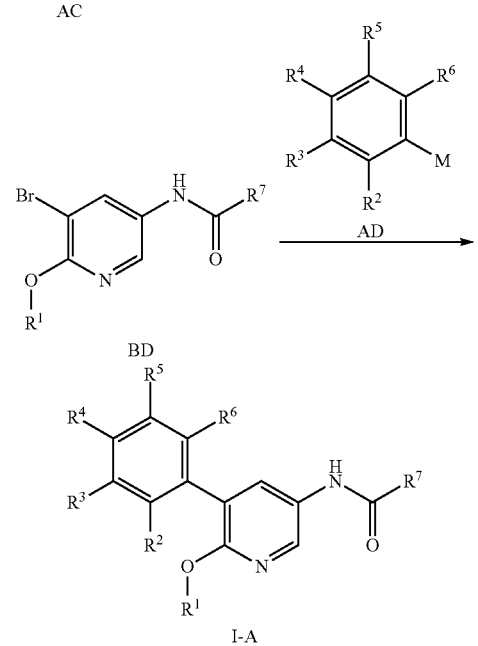

Compounds of formula AD containing functional groups detrimental to palladium catalyzed Suzuki reactions can for the purpose of carrying out this reaction be protected with a suitable protecting group (P). Suitable amine protecting groups are for example benzyloxy-carbonyl (Z), t-butyloxycarbonyl (BOC), while suitable acid protecting groups are for example benzyl (Bn), benzyloxymethyl (BOM), methoxyethoxymethyl (MEM) or allyl groups and silyl groups such as trimethylsilyl, triethylsilyl and tert-butyldimethylsilyl esters (for more details see T. W. Greene et al., Protective Groups in Organic Chemistry, John Wiley and Sons Inc. New York 1999, 3$^{rd}$ edition). Protecting group removal can be carried out by suitable methods known in the art.

Following the procedure according to scheme 3, compound CA (3-bromo-5-chloro-2-fluoro-pyridine, CAN 884484-87-5) can be used as starting material. CA is commercially available.

Compound CB can be prepared from CA by coupling a suitably substituted aryl metal species of formula AD, particularly an arylboronic acid or arylboronic acid ester in the presence of a suitable catalyst, in particular a palladium catalyst and more particularly palladium(II) acetate/triphenylphosphine mixtures or palladium(II)chloride-dppf (1,1'-bis(diphenyl-phosphino)ferrocene) complexes and a base such as triethylamine, sodium carbonate or potassium phosphate in an inert solvent such as dimethylformamide, toluene, tetrahydrofuran, acetonitrile and dimethoxyethane.

Compounds of formula AD containing functional groups detrimental to palladium catalyzed Suzuki reactions can for the purpose of carrying out this reaction be protected with a suitable protecting group (P). Suitable amine protecting groups are for example benzyloxy-carbonyl (Z), t-butyloxycarbonyl (BOC), while suitable acid protecting groups are for example benzyl (Bn), benzyloxymethyl (BOM), methoxyethoxymethyl (MEM) or allyl groups and silyl groups such as trimethylsilyl, triethylsilyl and tert-butyldimethylsilyl esters (for more details see T. W. Greene et al., Protective Groups in Organic Chemistry, John Wiley and Sons Inc. New York 1999, 3$^{rd}$ edition). Protecting group removal can be carried out by suitable methods known in the art.

Compound CC can be prepared from CB by reaction with a suitably substituted primary or secondary alcohol $R^1$—OH in the presence of a base, for example sodium hydride, with or without an inert solvent, for example dimethylformamide, at temperatures from room temperature to reflux temperature of the solvent, preferably at room temperature.

Compounds of the general formula CD can be obtained from compounds of the general formula CC by transition metal catalyzed, more specifically palladium catalyzed, preferentially palladium(II)chloride-dppf catalyzed reaction with carbon monoxide in a suitable solvent such as a primary alcohol, particularly methanol, at pressures of carbon monoxide of 1 to 200 bar, in particular 1 to 70 bar and temperatures of 0 to 150° C., particularly 1 to 100° C.

The saponification of the resulting ester CD by methods well known to the ones skilled in the art leads to acids of the general formula CE.

Compounds of general formula CF can be obtained from compounds of general formula CE by means of a Curtius rearrangement, preferentially by treatment with diphenylphosphoryl azide and a base, particularly triethylamine, in boiling t-butanol. The carbamates of the general formula CF can be deprotected by methods well known in the art to yield the amines of the general formula II. Alternatively the amines of general formula II can be prepared from the acids of general formula CE by synthesizing the corresponding primary amide followed by a Hoffmann rearrangement.

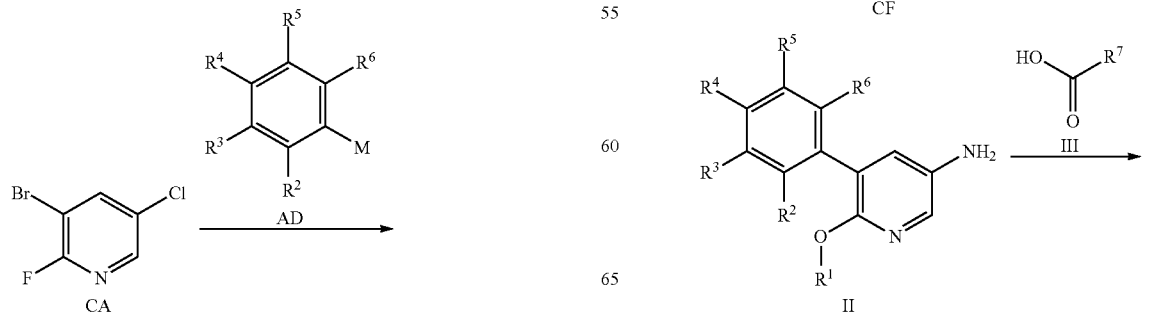

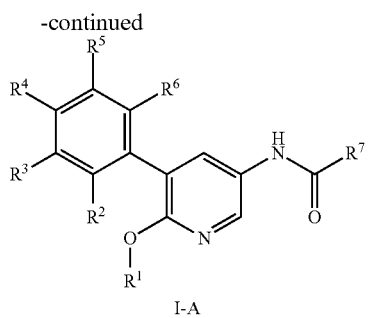

I-A

Compound I-A can be prepared from II and the corresponding acid of formula III by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature.

Following the procedure according to scheme 4, compounds of general formula DA (the synthesis of which has been described for example in WO2008040651 and WO2008040649) can be used as starting materials to provide compounds of general formula I-B.

In particular compounds of general formula DB can be prepared from compounds of general formula DA by reaction with a suitably substituted primary or secondary alcohol R¹—OH in the presence of a base, for example cesium carbonate, with or without an inert solvent, for example dimethylsulfoxide, at temperatures from room temperature to reflux temperature of the solvent, particularly at room temperature.

The saponification of the resulting ester of general formula DB by methods well known to the ones skilled in the art leads to acids of the general formula DC.

Compounds of general formula DD can be obtained from compounds of general formula DC by means of a Curtius rearrangement, preferentially by treatment with diphenylphosphoryl azide and a base, particularly triethylamine, in boiling t-butanol. The carbamates of the general formula DD can be deprotected by methods well known in the art to yield the amines of the general formula IV. Alternatively the amines of general formula IV can be prepared from the acids of general formula DC by synthesizing the corresponding primary amide followed by a Hoffmann rearrangement.

Compounds of general formula I-B can be prepared from IV and the corresponding acids of formula III by suitable amide bond forming reactions. These reactions are known in the art. For example coupling reagents like N,N'-carbonyl-diimidazole (CDI), N,N'-dicyclohexylcarbo-diimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature.

Scheme 4

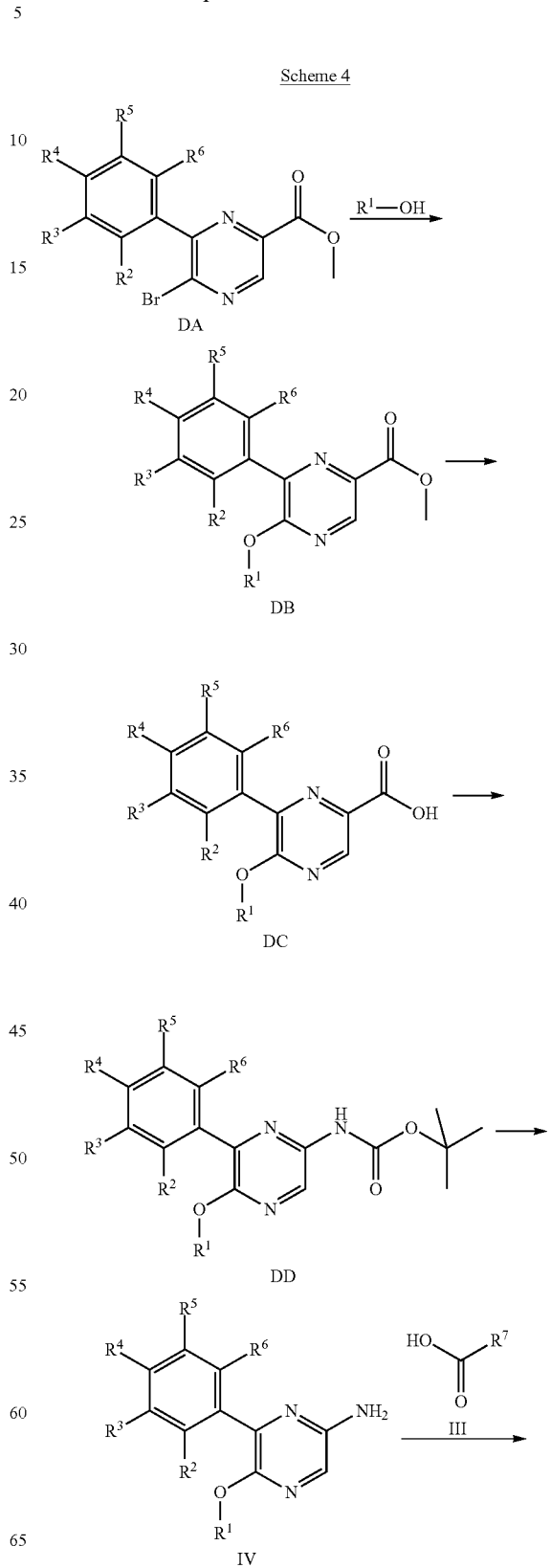

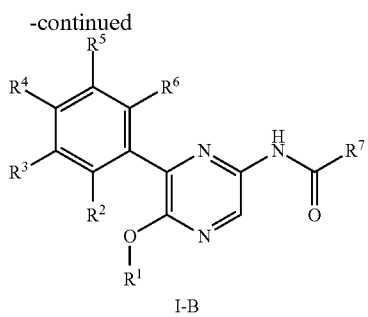

I-B

Compounds of general formula I-A or I-B can, if necessary, by methods known in the art, be processed further to other compounds of the same general formula. This could for example entail protective group removal by methods known in the art (for more details see T. W. Greene et al., Protective Groups in Organic Chemistry, John Wiley and Sons Inc. New York 1999, $3^{rd}$ edition); or simple functional group transformations, for example the transformation of a keto group to a hydroxyimino or methoxyimino group.

As described above, the compounds of formula I of the present invention or pharmaceutically acceptable salts thereof can be used as medicaments for the treatment and/or prophylaxis of diseases which can be treated with HDL-cholesterol raising agents. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia. In an embodiment, the medicament may be used for the treatment and/or prevention of dyslipidemia, atherosclerosis and cardiovascular diseases.

The invention therefore also relates to pharmaceutical compositions comprising a compound of formula I as defined above or a pharmaceutically acceptable salt thereof and a pharmaceutically acceptable carrier and/or adjuvant. The pharmaceutical compositions are useful in the treatment and/or prophylaxis of diseases which can be treated with HDL-cholesterol raising agents.

Thus, the invention relates to a pharmaceutical composition as defined above for use in the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or prophylaxis of diseases which can be treated with HDL-cholesterol raising agents, which method comprises administering a therapeutically effective amount of a compound of formula I or a pharmaceutically acceptable salt thereof to a patient in need thereof. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia. In an embodiment, the method is for the treatment and/or prophylaxis of dyslipidemia, atherosclerosis and cardiovascular diseases.

The invention also relates to the compounds of formula I or pharmaceutically acceptable salts thereof for use as medicaments. In an embodiment, the invention relates to compounds of formula I or pharmaceutically acceptable salts thereof for use as HDL-cholesterol raising agents. Thus, the invention is concerned with compounds of formula I or pharmaceutically acceptable salts thereof for use in the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia. In an embodiment, compounds of the present invention, or pharmaceutically acceptable salts thereof are for use in the treatment and/or prophylaxis of dyslipidemia, atherosclerosis and cardiovascular diseases.

In addition, the invention relates to the use of compounds of formula I as defined above or pharmaceutically acceptable salts thereof for the preparation of a medicament for the treatment and/or prophylaxis of diseases can be treated with HDL raising agents. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia. An embodiment of the present invention relates to the use of compounds of formula I as defined above or pharmaceutically acceptable salts thereof for the preparation of medicaments for the treatment and/or prophylaxis of dyslipidemia, atherosclerosis and cardiovascular diseases.

In addition, HDL raising agents of formula I are useful in combination or association with another compound, said compound being selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor and a bile acid sequestrant.

The invention therefore also relates to pharmaceutical compositions comprising a compound of formula I as defined above or a pharmaceutically acceptable salt thereof in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor and a bile acid sequestrant, as well as a pharmaceutically acceptable carrier and/or adjuvant.

The invention further relates to compounds of formula I as defined above or pharmaceutically acceptable salts thereof in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor and a bile acid sequestrant for use in the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

The invention also relates to a method for the treatment and/or prophylaxis of diseases which can be treated with HDL-cholesterol raising agents, which method comprises administration of a therapeutically effective amount of a compound according to formula I or a pharmaceutically acceptable salt thereof in combination or association with a therapeutically effective amount of a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor and a bile acid sequestrant.

Pharmaceutical Compositions

The compounds of formula I and/or their pharmaceutically acceptable salts can be used in the form of pharmaceutical compositions for enteral, parenteral or topical administration. They can be administered, for example, perorally, e.g. in the form of tablets, coated tablets, dragées, hard and soft gelatine capsules, solutions, emulsions or suspensions, orally, e.g. in the form of buccal cavities, rectally, e.g. in the form of suppositories, parenterally, e.g. in the form of injection solutions or infusion solutions for intramuscular, intravenous or subcutaneous injection, or topically, e.g. in the form of ointments, creams or oils. In an embodiment, the compound or a pharmaceutically acceptable salt thereof is administered orally.

The production of the pharmaceutical compositions can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The therapeutically effective amount or dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 100 mg, especially about 1 to 50 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 1-100 mg, preferably 5-50 mg, of a compound of formula I.

The following examples C1 to C3 illustrate typical compositions of the present invention, but serve merely as representative thereof.

EXAMPLE C1

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

EXAMPLE C2

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

EXAMPLE C3

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Pharmacological Tests

The following tests were carried out in order to determine the activity of the compounds of formula I and their valuable pharmacological properties.

Detection of Upregulation of ABCA1 Protein in Cells

The ability of compounds of the invention to increase the level of ABCA1 protein is determined in replicate cultures of THP-1 macrophage cells in 96-well microplates. Cells are plated at an initial density of 100,000 cells/well in 100 μl medium and differentiated to adherent macrophages with the addition of PMA (100 nM) for 68 hrs in 10% fetal bovine serum, 3 μl/L of b-mercaptoethanol, RPMI-1640 medium. Then, cells are incubated with RPMI-1640 medium containing 1% FCS, 25 μg/ml acetylated LDL, for 24 hours at 37°. Following incubation with acetylated LDL, cells are washed twice with 50 μl PBS and incubated with 100 μl of RPMI-1640 medium containing the compound of interest solubilized in DMSO for an additional 24 hrs. The final DMSO concentration in presence of cells is maintained at 0.5%. ApoA-I binding assay using High Content Image Analysis is initiated by replacing with fresh medium, RPMI without Phenol Red, 0.2% BSA containing AlexaFluor®647 labeled ApoA-I for 2 h/37° C./5% CO2. Then, cells are fixed with 4% Formaldehyde inPBS (15 min, RT). Following Nuclei are stained with Hoechst solution (3 μM PBS) and Cytoplasm with Cell Mask Blue (2 μg/ml PBS), 15 min, RT. Finally the stained cells are fixed with a second round of formaldehyde treatment. Fixed stained cells are washed and kept in PBS at 4° C. and can be read immediately until one month after preparation. That the binding of ApoA-I indeed reflected the level of ABCA1 in the cell, was demonstrated by loss of signal when ABCA1 expression was artificially reduced by transfection with small interfering RNA's.

The Alexa Fluor 647-labeled Apolipoprotein A-I (20 nM) was prepared as follows: Human recombinant Apolipoprotein A-I (ApoA-I) was exchanged to a buffer of 0.02 M $NaHCO_3$ at pH 8.2 on an NAP desalting column (GE Healthcare) and brought to a concentration to 40 μM (1.13 mg/ml) by adjustment with the same buffer. The ApoA-I was fluorescently labeled by incubation with Alexa Fluor carboxylic acid succimidyl ester. (Alexa Fluor 647, Invitrogen A-20006) at a 2:1 molar ratio (Alexa to ApoA-I) for 1 h under shaking at RT. The remaining unconjugated label was removed by buffer exchange to 0.02M $NaHCO_3$ at pH 8.2.

Imaging and data collection were performed on an OPERA confocal microplate imaging reader using a 20× water immersion objective and UV360 or 405 laser to identify the cell nuclei and a 635 laser to identify the fluorescent ApoA-I. Eight fields of view are captured per well. Image capture and analysis was performed with the Acapella software. Background fluorescence detected in control wells without ApoA-I was subtracted.

Using XLfit3 program (ID Business Solutions Ltd. UK), the model 205 for Dose Response One Site is used to calculate the $EC_{50}$ values. The compounds of the present invention increase the level of ABCA1 protein by more than 45% at a concentration of 3 μM. Preferably the compounds exhibit $EC_{50}$ values in a range of 0.1 μl to 10 μM in the ABCA1 protein detection assay. Even more preferably, the compounds of the present invention have $EC_{50}$ values in a range of 0.1 μM to 3 μM.

TABLE 1

ABCA1 protein increasing efficacy

| Example | % increase of ABCA1 at 3 μM | $EC_{50}$ [μM] |
|---|---|---|
| 1 | >45% @ 3 μM | |
| 2 | | 2.69 |
| 3 | | 2.28 |
| 4 | >45% @ 3 μM | |
| 5 | >45% @ 3 μM | |
| 6 | >45% @ 3 μM | |
| 7 | >45% @ 3 μM | |
| 8 | | 2.77 |
| 9 | >45% @ 3 μM | |
| 10 | | 6.51 |
| 11 | >45% @ 3 μM | |
| 12 | >45% @ 3 μM | |
| 13 | >45% @ 3 μM | |
| 14 | >45% @ 3 μM | |
| 15 | >45% @ 3 μM | |
| 16 | | 6.05 |
| 17 | | 2.31 |
| 18 | >45% @ 3 μM | |
| 19 | | 1.39 |
| 20 | | 6.4 |
| 21 | | 1.37 |
| 22 | >45% @ 3 μM | |
| 23 | | 0.72 |
| 24 | | 2.31 |
| 25 | | 2.65 |
| 26 | >45% @ 3 μM | |
| 27 | >45% @ 3 μM | |
| 28 | >45% @ 3 μM | |
| 29 | >45% @ 3 μM | |
| 30 | | 3.86 |
| 31 | >45% @ 3 μM | |
| 32 | | 1 |
| 33 | >45% @ 3 μM | |
| 34 | | 2.4 |
| 35 | | 0.51 |
| 36 | | |
| 37 | >45% @ 3 μM | |
| 38 | | 2.91 |
| 39 | | 2.23 |

TABLE 1-continued

ABCA1 protein increasing efficacy

| Example | % increase of ABCA1 at 3 μM | EC$_{50}$ [μM] |
|---|---|---|
| 40 | | 3.31 |
| 41 | >45% @ 3 μM | |
| 42 | | 8.54 |
| 43 | | 5.95 |
| 44 | | 1.26 |
| 45 | | 1.03 |
| 46 | >45% @ 3 μM | |
| 47 | | 1.36 |
| 48 | >45% @ 3 μM | |
| 49 | | 0.3 |
| 50 | | 1.5 |
| 51 | >45% @ 3 μM | |
| 52 | >45% @ 3 μM | |
| 53 | >45% @ 3 μM | |
| 54 | >45% @ 3 μM | |
| 55 | >45% @ 3 μM | |
| 56 | >45% @ 3 μM | |
| 57 | >45% @ 3 μM | |
| 58 | | 2.2 |
| 59 | | 3.9 |
| 60 | >45% @ 3 μM | |
| 61 | >45% @ 3 μM | |
| 62 | | 2.39 |
| 63 | | 0.68 |
| 64 | | 1.08 |
| 65 | | 0.27 |
| 66 | >45% @ 3 μM | |
| 67 | >45% @ 3 μM | |
| 68 | >45% @ 3 μM | |
| 69 | >45% @ 3 μM | |
| 70 | >45% @ 3 μM | |
| 71 | >45% @ 3 μM | |
| 72 | | 0.78 |
| 73 | >45% @ 3 μM | |
| 74 | >45% @ 3 μM | |
| 75 | >45% @ 3 μM | |
| 76 | >45% @ 3 μM | |
| 77 | | 0.72 |
| 78 | >45% @ 3 μM | |
| 79 | >45% @ 3 μM | |
| 80 | >45% @ 3 μM | |
| 81 | | 2.56 |
| 82 | >45% @ 3 μM | |
| 83 | >45% @ 3 μM | |
| 84 | >45% @ 3 μM | |
| 85 | >45% @ 3 μM | |
| 86 | >45% @ 3 μM | |
| 87 | >45% @ 3 μM | |
| 88 | >45% @ 3 μM | |
| 89 | | 3.31 |

Cholesterol Efflux Assay

The ability of compounds of the invention to stimulate cholesterol efflux is determined in replicate cultures of THP-1 cells in 96-well microplates. Cells are plated at an initial density of 150,000 cells/well and differentiated to macrophages with the addition of PMA (100 ng/ml) for 72 hrs in 10% fetal bovine serum, 3 μl/L of beta-mercaptoethanol, RPMI-1640 medium. Cells are washed once with RPMI-1640 and loaded with RPMI-1640 medium containing 2% FCS, 50 μg/ml acetylated LDL, and 10 μCi/ml [$^3$H]cholesterol for 48 hours at 37° C. After loading the cells are washed once with RPMI-1640 and incubated with the compound of interest from DMSO solutions for an additional 24 hrs in RPMI-1640 medium containing 1 mg/ml fatty acid free-bovine serum albumin (BSA). Upon incubation cells are washed once, and cholesterol efflux is induced by the addition of 10 μg/ml Apolipoprotein AI in RPMI-1640 containing 1 mg/ml BSA and in the presence of the compound for an additional 6 hrs. Following incubation radioactivity is determined in the supernatants and cholesterol efflux is expressed as the percent stimulation over replicate cultures treated only with DMSO. Sigmoidal curves were fitted using the XLfit3 program (ID Business Solutions Ltd. UK) and EC$_{50}$ values were determined. The compounds of the present invention exhibit EC$_{50}$ values in a range of 0.1 μM to 3.0 μM in the cholesterol efflux assay. Preferably, the compounds of the present invention have EC$_{50}$ values in a range of 0.1 μM to 1.5 μM.

CB1 and CB2 Receptor Affinity

The affinity of the compounds of the invention for cannabinoid receptors was determined using membrane preparations of human embryonic kidney (HEK) cells in which the human CB1 receptor is transiently transfected using a Semliki Forest Virus system in conjunction with [$^3$H]-CP-55,940 as radioligand. After incubation of freshly prepared cell membrane preparation with the [$^3$H]-ligand, with or without addition of compounds of the invention, separation of bound and free ligand was performed by filtration over glass fiber filters. Radioactivity on the filter was measured by scintillation counting.

The affinity of the compounds of the invention for cannabinoid CB2 receptors was determined using membrane preparations of human embryonic kidney (HEK) cells in which the human CB2 receptor is transiently transfected using a Semliki Forest Virus system in conjunction with [$^3$H]-CP-55,940 as radioligand. After incubation of freshly prepared cell membrane preparation with the [$^3$H]-ligand, with or without addition of compounds of the invention, separation of bound and free ligand was performed by filtration over glass fiber filters. Radioactivity on the filter was measured by scintillation counting.

The ability of the compounds to displace the radioligand [$^3$H]-CP-55,940 was measured at a concentration of 10 μM and values provided as [% inhibition @ 10 μM] both for the CB1 and CB2 receptor assay. The lower % inhibition is, the lower the likelihood of side effects based on CB1 or CB2 receptor inhibition is.

The compounds of the present invention exhibit values below 50% inhibition in both the CB1 and CB2 receptor assay at a concentration of 10 μM. Preferably, the compounds of the present invention exhibit values below 35% inhibition in both the CB1 and CB2 receptor assays and even more preferably below 20% in both assays.

TABLE 2

CB1 and CB2-receptor affinity

| Example | CB1 receptor affinity [% inhibition @ 10 μM] | CB2 receptor affinity [% inhibition @ 10 μM] |
|---|---|---|
| 1 | 45 | 9.2 |
| 2 | 33 | 4.9 |
| 3 | 29 | 8.0 |
| 4 | 36 | 1.9 |
| 5 | 19 | −5.4 |
| 6 | 47 | 11 |
| 7 | 13 | 1.2 |
| 8 | 52 | 15 |
| 9 | 24 | 9.6 |
| 10 | 36 | 28 |
| 11 | 25 | −1.2 |
| 12 | 22 | 4 |
| 13 | 16 | 3 |
| 14 | 38 | 10 |
| 15 | 27 | 2 |
| 16 | 34 | −1 |
| 17 | 16 | −3 |
| 18 | 37 | 3 |
| 19 | 25 | −10 |
| 20 | 34 | 9 |

TABLE 2-continued

CB1 and CB2-receptor affinity

| Example | CB1 receptor affinity [% inhibition @ 10 μM] | CB2 receptor affinity [% inhibition @ 10 μM] |
|---|---|---|
| 21 | 29 | 1 |
| 22 | 45 | 8 |
| 23 | 12 | −8 |
| 24 | 25 | −1 |
| 25 | 25 | −1 |
| 26 | 37 | 11 |
| 27 | 47 | 10 |
| 28 | 36 | −6 |
| 29 | 41 | 19 |
| 30 | 27 | −4 |
| 31 | 44 | 7 |
| 32 | 21 | 0.9 |
| 33 | 22 | −2 |
| 34 | 31 | 10 |
| 35 | 18 | −3 |
| 36 | 18 | 2 |
| 37 | 27 | 8 |
| 38 | 12 | 15 |
| 39 | 19 | 16 |
| 40 | 19 | −5 |
| 41 | 31 | 8 |
| 42 | 23 | 6 |
| 43 | 31 | 6 |
| 44 | 15 | 14 |
| 45 | 11 | 13 |
| 46 | 40 | −1 |
| 47 | 34 | 5 |
| 48 | 40 | −2 |
| 49 | 39 | −3 |
| 50 | 39 | −1 |
| 51 | 48 | 6 |
| 52 | 34 | 6 |
| 53 | 21 | 0 |
| 54 | 21 | 10 |
| 55 | 35 | 4 |
| 56 | 35 | 0 |
| 57 | 0 | −18 |
| 58 | 3 | −13 |
| 59 | 22 | 18 |
| 60 | 38 | −2 |
| 61 | 17 | 12 |
| 62 | −4 | 4 |
| 63 | 5 | −1 |
| 64 | 9 | 2 |
| 65 | 19 | 5 |
| 66 | 30 | 5 |
| 67 | 33 | 9 |
| 68 | 26 | 4 |
| 69 | 35 | 18 |
| 70 | 49 | 15 |
| 71 | 41 | 4 |
| 72 | 25 | −7 |
| 73 | 13 | 22 |
| 74 | 17 | −7 |
| 75 | 31 | 5 |
| 76 | 1 | 5 |
| 77 | 33 | 16 |
| 78 | 25 | 26 |
| 79 | 29 | 13 |
| 80 | 16 | 14 |
| 81 | 21 | 5 |
| 82 | 29 | 37 |
| 83 | 27 | −5 |
| 84 | 23 | 3 |
| 85 | 38 | 5 |
| 86 | 48 | 5 |
| 87 | 19 | −15 |
| 88 | 41 | 16 |
| 89 | 35 | 5 |

Further demonstration of biological activities of the compounds of the present invention may be accomplished through the following in vivo assays that are well known in the art.

Effects on Plasma Lipid Levels in Lean, Chow Fed Rats

The effects of compounds of compounds of formula I on plasma lipid levels were determined in lean, chow-fed Sprague-Dawley rats with compounds administered by p.o. gavage. After one week of acclimatisation, blood samples were collected from 4 hour-fasted animals for plasma lipid determination. Animals were then assigned to treatment groups based on HDL-cholesterol levels. Compounds of formula I were administered by gavage, once daily for five days. Control animals received vehicle alone. Blood was collected on day five from 4 hour-fasted rats, 2 hours after a final treatment, for plasma lipid analysis. Total cholesterol, HDL-cholesterol, and triglycerides were determined by measuring total cholesterol, HDL-cholesterol, and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Obese, High Fat Diet Fed Rats

Efficacy of compounds in modulating plasma lipid levels was determined also in obese male Sprague Dawley rats after 28-29 days administration of compounds. Male Sprague-Dawley rats of 10 weeks of age were fed a high fat diet during 3 weeks. Obese rats were distributed in groups according to homogeneous BW and FI evaluated a week before the start of the treatment. Treatment was administered as food-Admix. On day 29, blood was taken in the morning under slight anesthesia (retro-orbital method) in post-prandial conditions i.e. 4h after food was removed. Plasma was separated from blood by low speed centrifugation and selected organs were taken (e.g liver, fat). Total cholesterol, HDL-cholesterol, and triglycerides were determined by measuring total cholesterol, HDL-cholesterol, LDL-cholesterol and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Hamsters

Efficacy of compounds in modulating plasma lipid levels was determined in hamsters after 5 days of daily administration of compounds. Male hamsters of 6-8 weeks of age were used in the studies. After one week of acclimation, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using colorimetric enzymatic assays (Roche Diagnostic GmbH, Mannheim, Germany). HDL-cholesterol, LDL-cholesterol, and VLDL-cholesterol levels were also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Cholesterol/Fat Fed Hamsters

Efficacy of compounds in modulating plasma lipid levels was determined in hamsters after 5 days of daily administration of compounds. Male hamsters of 6-8 weeks of age were used in the studies. After one week of acclimatisation, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using colorimetric enzymatic assays (Roche Diagnostic GmbH, Mannheim, Germany). HDL-cholesterol was also determined after selective precipitation of HDL from plasma by standard procedures.

EXAMPLES

MS=mass spectrometry; EI=electron ionization; ESI=electrospray; NMR data are reported in parts per million (δ) relative to internal tetramethylsilane and are referenced to the deuterium lock signal from the sample solvent ($d_6$-DMSO unless otherwise stated); coupling constants (J) are in Hertz, mp=melting point; bp=boiling point; HPLC=LC=high performance liquid chromatography, Rt=retention time, TLC=thin layer chromatography, RT=room temperature, DIPEA=diisopropylethylamine, DPPA=phosphoric acid diphenyl ester azide, TBTU=O-(benzotriazol-1-yl)-N,N',N'-tetramethyl-uronium-tetrafluoroborate; TEMPO=2,2,6,6-tetra-methylpiperidine 1-oxyl radical, DMF=dimethylformamide, DMSO=dimethyl-sulfoxide, THF=tetrahydrofuran, CAN=CAS Registry Number.

Preparation of Intermediates

Example A

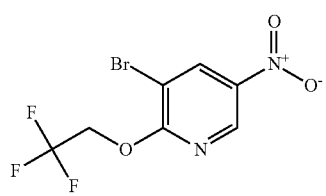 [SMILES: O=[N+]([O-])c1cnc(OCC(F)(F)F)c(Br)c1]

Preparation of 3-bromo-5-nitro-2-(2,2,2-trifluoro-ethoxy)-pyridine

Sodium hydride (3.2 g, 80.02 mmol) was added carefully in small portions to 2,2,2-trifluroethanol (CAS Registry No. 75-89-8) (60 ml) at 0° C. under nitrogen atmosphere and stirred at 25° C. for 30 minutes. Then 3-bromo-2-chloro-5-nitropyridine (CAS Registry No. 5470-17-7) (2 g, 8.42 mmol) in trifluoroethanol was added, and the reaction mixture was refluxed for 16h. The solvent was evaporated in vacuo, and the residue was taken up in water and extracted with ethyl acetate (3×120 ml). The combined organic layers were washed with water and brine, dried over $Na_2SO_4$ and concentrated to get the crude residue (3 g). The crude was purified by column chromatography (3% ethyl acetate/hexane) to give the desired product (2.4 g, 95%) as yellow liquid. MS (LC/MS): not responding, NMR is in agreement with the structure: $^1$H-NMR (400 MHz, $CDCl_3$): δ 4.90 (m, 2H), 8.68 (d, 1H), 8.98 (d, 1H).

Example B

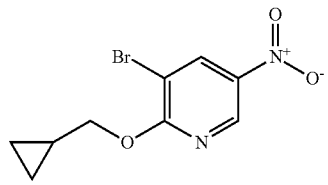 [SMILES: O=[N+]([O-])c1cnc(OCC2CC2)c(Br)c1]

Preparation of 3-bromo-2-cyclopropylmethoxy-5-nitro-pyridine

To a solution of sodium hydride (2.21 g, 55.34 mmol) in anhydrous DMF (20 ml) was added cyclopropylmethanol (CAS Registry No. 2516-33-8) (12.45 ml, 153.2 mmol) under nitrogen at 0° C. and the reaction mixture was stirred at 25° C. for 30 minutes. Then 3-bromo-2-chloro-5-nitropyridine (CAS Registry No. 5470-17-7) (7.3 g, 30.74 mmol) was added drop wise at 0° C. and stirred for two hours at 25° C. Water (60ml) was added to the reaction mixture and extracted with ethyl acetate (3×100 ml). The combined organic layers were washed with water and brine, dried over $Na_2SO_4$ and evaporated under reduced pressure to get the crude residue (12 g). The crude was purified by column chromatography (2% ethyl acetate/hexane) to get the desired product (2.06 g, 32%) as light yellow solid and 1.7 g of unreacted 3-bromo-2-chloro-5-nitropyridine was recovered. MS (LC/MS): not responding, NMR is in agreement with the structure: $^1$H-NMR (400 MHz, $CDCl_3$): δ 0.41 (m, 2H), 0.65 (m, 2H), 1.32 (m, 1H), 4.34 (d, 2H), 8.60 (d, 1H), 8.96 (d, 1H).

Example C

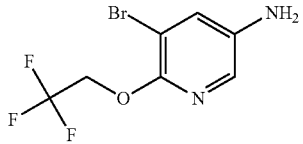 [SMILES: Nc1cnc(OCC(F)(F)F)c(Br)c1]

Preparation of 5-bromo-6-(2,2,2-trifluoro-ethoxy)-pyridin-3-ylamine

To a solution of 3-bromo-5-nitro-2-(2, 2, 2-trifluoro-ethoxy)-pyridine (2.4 g, 7.97 mmol) in ethanol (100 ml) were added HCl (0.3 ml) and stannous chloride (10.5 g, 55.81 mmol) at 25° C. and the reaction mixture was stirred for 4 h at 25° C. After total consumption of starting material (monitored by TLC), ethanol was evaporated under reduced pressure, diluted with ethyl acetate, neutralized with aqueous $Na_2CO_3$ solution, and filtered through a bed of celite. The organic layer was separated and the aqueous layer was further extracted with ethyl acetate (2×120 ml). The combined organic layer was washed with brine, dried over $Na_2SO_4$ and evaporated in vacuo to get the desired compound (2.1 g, 97%) as brown liquid. This was used as such for the next step without further purification. MS (LC/MS): not responding, NMR is in agreement with the structure: $^1$H-NMR (400 MHz, CDCl$_3$): δ 4.70 (m, 2H), 7.30 (d, 1H), 7.54 (d, 1H).

Example D

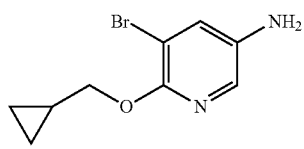 [SMILES: Nc1cnc(OCC2CC2)c(Br)c1]

Preparation of 5-bromo-6-cyclopropylmethoxy-pyridin-3-ylamine

To a solution of 3-bromo-2-cyclopropylmethoxy-5-nitropyridine (600 mg, 2.19 mmol) in methanol (30 ml) were added water (15 ml), zinc dust (1 g, 15.37 mmol) and ammonium chloride (1.28 g, 24.09 mmol) at 25° C., and the reaction mixture was stirred for 45 min at 25° C. After total consumption of starting material (monitored by TLC), the reaction mixture was filtered through a bed of celite, and the filtrate was evaporated under reduced pressure to get the crude residue. The residue was dissolved in dichloromethane and washed with water and brine. The organic part was dried over Na$_2$SO$_4$ and evaporated to get the compound (507 mg, 95%). This compound was used in next step without further purification. MS (LC/MS): 244.0 (M+H).

Example E

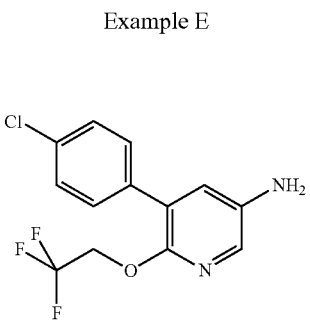

Preparation of 5-(4-chloro-phenyl)-6-(2, 2, 2-trifluoro-ethoxy)-pyridin-3-ylamine To a solution of 5-bromo-6-(2, 2, 2-trifluoro-ethoxy)-pyridin-3-ylamine (2.1 g, 7.74 mmol) in DME, ethanol, water (3:1:1) (50 ml) in a sealed tube were added 4-chlorophenylboronic acid (CAS Registry No. 1679-18-1) (1.8 g, 11.62 mmol) and potassium phosphate (4.9 g, 23.22 mmol), and then the reaction mixture was purged with nitrogen for 15 min. Then Pd(dppf)$_2$Cl$_2$ (651 mg, 0.93 mmol) was added to the reaction mixture and heated at 100° C. for 4 h. The reaction mixture was filtered off and the filter cake was washed with ethyl acetate (3×20 ml). The organic layer was washed with water, brine, dried over Na$_2$SO$_4$ and evaporated in vacuo to get the crude (1.9 g). The crude was purified by column chromatography (20-25% ethyl acetate/hexane) to get the desired product (1.3 g, 56%) as brown liquid. MS (LC/MS): 303.0 (M+H).

Example F

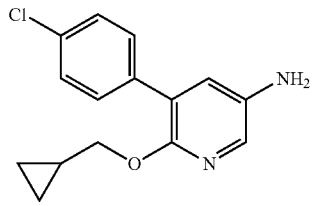 [SMILES: Nc1cnc(OCC2CC2)c(-c2ccc(Cl)cc2)c1]

Preparation of 5-(4-chloro-phenyl)-6-cyclopropyl-methoxy-pyridin-3-ylamine

The title compound was synthesized in analogy to Example E, using 5-bromo-6-cyclopropylmethoxy-pyridin-3-ylamine and 4-chlorophenylboronic acid (44%). MS (LC/MS): 275.2 (M+H).

Example G

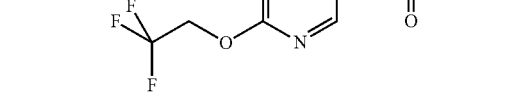

Preparation of N-[5-Bromo-6-(2,2,2-trifluoro-ethoxy)-pyridin-3-yl]-nicotinamide

To a solution of nicotinic acid (454 mg, 3.69 mmol) in DMF (33 mL) were added successively TBTU (1.18 g, 3.69 mmol), N,N-diisopropylethylamine (3.16 mL, 18.4 mmol) and 5-bromo-6-(2,2,2-trifluoroethoxy)pyridin-3-amine (1 g, 3.69 mmol). The brown mixture was stirred under argon for 3 h at room temperature. After evaporation of DMF, the brown oil was partitioned between ethyl acetate (50 mL) and 1M NaOH (30 mL). The aqueous layers were back-extracted with ethyl acetate (1×50 mL). The organic parts were washed with water (2×25 mL) and brine (25 mL), then dried over MgSO$_4$ and concentrated in vacuo. The crude material was purified by flash chromatography (silica gel, 40 g, 10% to 100% ethyl acetate in heptane) to deliver the desired product as a white solid (580 mg; 42%); MS (EI): 376.1; 378.0 (M+H).

Example 1

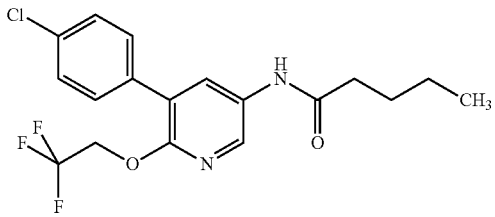 [SMILES: CCCCC(=O)Nc1cnc(OCC(F)(F)F)c(-c2ccc(Cl)cc2)c1]

Preparation of pentanoic acid[5-(4-chloro-phenyl)-6-(2,2,2-trifluoro-ethoxy)-pyridin-3-yl]-amide To a solution of 5-(4-chloro-phenyl)-6-(2,2,2-trifluoro-ethoxy)-pyridin-3-ylamine (50 mg, 0.165 mmol) and valeric acid (36 mg, 0.247 mmol) in DMF (5 ml) were added N-methyl morpholine (51 mg, 0.5 mmol) and HBTU (94 mg, 0.247 mmol), and the reaction mixture was stirred for 16 h at 25° C. The reaction mixture was poured into water and extracted with ethyl acetate (3×20 ml). The combined ethyl acetate part was dried over $Na_2SO_4$ and evaporated to furnish the crude material (60 mg). The crude was purified by prep. HPLC and the desired product (30 mg, 47%) was obtained as sticky white solid. MS (LC/MS): 387.2 (M+H).

Example 2

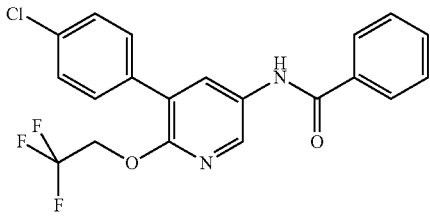 [SMILES: O=C(Nc1cnc(OCC(F)(F)F)c(-c2ccc(Cl)cc2)c1)c1ccccc1]

Preparation of N-[5-(4-chloro-phenyl)-6-(2,2,2-trifluoro-ethoxy)-pyridin-3-yl]-benzamide The title compound was synthesized in analogy to Example 1, using 5-(4-chloro-phenyl)-6-(2,2, 2-trifluoro-ethoxy)-pyridin-3-ylamine and benzoic acid as starting materials, MS (LC/MS): 407.2 (M+H).

Example 3

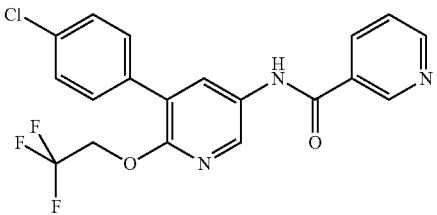 [SMILES: O=C(Nc1cnc(OCC(F)(F)F)c(-c2ccc(Cl)cc2)c1)c1cccnc1]

Preparation of N-[5-(4-chloro-phenyl)-6-(2,2,2-trifluoro-ethoxy)-pyridin-3-yl]-nicotinamide The title compound was synthesized in analogy to Example 1, using 5-(4-chloro-phenyl)-6-(2,2,2-trifluoro-ethoxy)-pyridin-3-ylamine and nicotinic acid as starting materials, MS (LC/MS): 408.0 (M+H).

Example 4

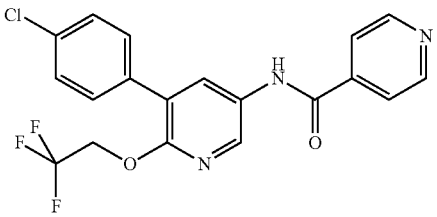 [SMILES: O=C(Nc1cnc(OCC(F)(F)F)c(-c2ccc(Cl)cc2)c1)c1ccncc1]

Preparation of N-[5-(4-chloro-phenyl)-6-(2,2,2-trifluoro-ethoxy)-pyridin-3-yl]-isonicotinamide The title compound was synthesized in analogy to Example 1, using 5-(4-chloro-phenyl)-6-(2,2, 2-trifluoro-ethoxy)-pyridin-3-ylamine and isonicotinic acid as starting materials, MS (LC/MS): 408.0 (M+H).

Example 5

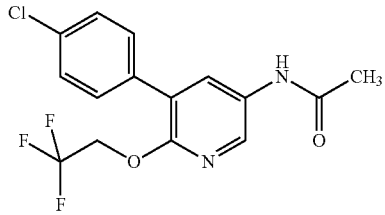 [SMILES: CC(=O)Nc1cnc(OCC(F)(F)F)c(-c2ccc(Cl)cc2)c1]

Preparation of N-[5-(4-chloro-phenyl)-6-(2,2,2-trifluoro-ethoxy)-pyridin-3-yl]-acetamide The title compound was synthesized in analogy to Example 1, using 5-(4-chloro-phenyl)-6-(2,2, 2-trifluoroethoxy)-pyridin-3-ylamine and acetic acid as starting materials, MS (LC/MS): 345.0 (M+H).

Example 6

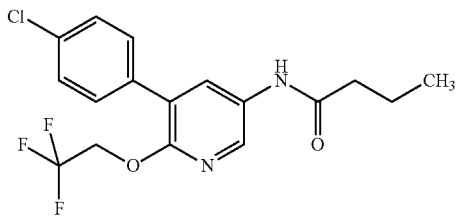 [SMILES: CCCC(=O)Nc1cnc(OCC(F)(F)F)c(-c2ccc(Cl)cc2)c1]

Preparation of N-[5-(4-Chloro-phenyl)-6-(2,2,2-trifluoro-ethoxy)-pyridin-3-yl]-butyramide The title compound was synthesized in analogy to Example 1, using 5-(4-chloro-phenyl)-6-(2,2, 2-trifluoro-ethoxy)-pyridin-3-ylamine and n-butyric acid as starting materials, MS (LC/MS): 373.2 (M+H).

Example 7

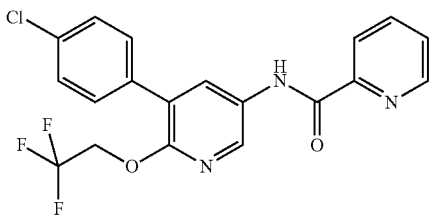 [SMILES: O=C(Nc1cnc(OCC(F)(F)F)c(-c2ccc(Cl)cc2)c1)c1ccccn1]

Preparation of pyridine-2-carboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2,2-trifluoro-ethoxy)-pyridin-3-ylamine and pyridine-2-carboxylic acid as starting materials, MS (LC/MS): 408.0 (M+H).

Example 8

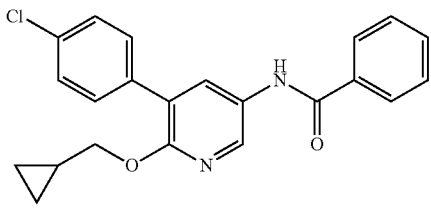 [SMILES: O=C(Nc1cnc(OCC2CC2)c(-c2ccc(Cl)cc2)c1)c1ccccc1]

Preparation of N-[5-(4-chloro-phenyl)-6-cyclopropylmethoxy-pyridin-3-yl]-benzamide The title compound was synthesized in analogy to Example 1, using 5-(4-chloro-phenyl)-6-cyclopropylmethoxy-pyridin-3-ylamine and benzoic acid as starting materials, MS (LC/MS): 379.2 (M+H).

Example 9

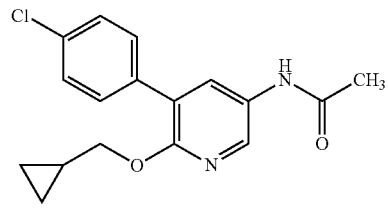 [SMILES: CC(=O)Nc1cnc(OCC2CC2)c(-c2ccc(Cl)cc2)c1]

Preparation of N-[5-(4-chloro-phenyl)-6-cyclopropylmethoxy-pyridin-3-yl]-acetamide The title compound was synthesized in analogy to Example 1, using 5-(4-chloro-phenyl)-6-cyclopropylmethoxy-pyridin-3-ylamine and acetic acid as starting materials, MS (LC/MS): 317.2 (M+H).

Example 10

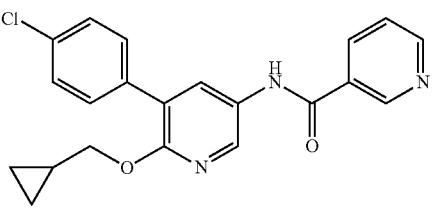 [SMILES: O=C(Nc1cnc(OCC2CC2)c(-c2ccc(Cl)cc2)c1)c1cccnc1]

Preparation of N-[5-(4-chloro-phenyl)-6-cyclopropylmethoxy-pyridin-3-yl]-nicotinamide The title compound was synthesized in analogy to Example 1, using 5-(4-chloro-phenyl)-6-cyclopropylmethoxy-pyridin-3-ylamine and nicotinic acid as starting materials, MS (LC/MS): 380.2 (M+H).

Example 11

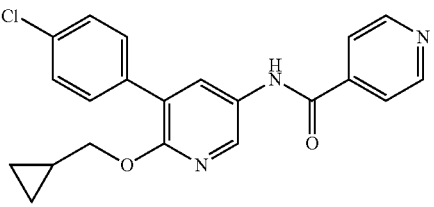 [SMILES: O=C(Nc1cnc(OCC2CC2)c(-c2ccc(Cl)cc2)c1)c1ccncc1]

Preparation of N-[5-(4-chloro-phenyl)-6-cyclopropylmethoxy-pyridin-3-yl]-isonicotinamide The title compound was synthesized in analogy to Example 1, using 5-(4-chloro-phenyl)-6-cyclopropylmethoxy-pyridin-3-ylamine and isonicotinic acid as starting materials, MS (LC/MS): 380.2 (M+H).

Example 12

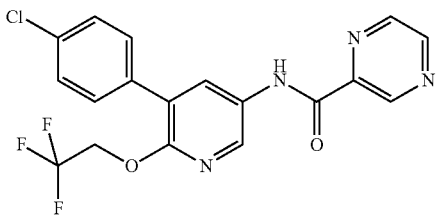 [SMILES: O=C(Nc1cnc(OCC(F)(F)F)c(-c2ccc(Cl)cc2)c1)c1cnccn1]

Preparation of pyrazine-2-carboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 2-pyrazinecarboxylic acid as starting materials, MS (LC/MS): 409.6 (M+H).

Example 13

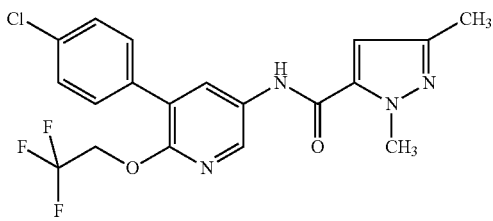 [SMILES: Cc1cc(C(=O)Nc2cnc(OCC(F)(F)F)c(-c3ccc(Cl)cc3)c2)n(C)n1]

Preparation of 2,5-dimethyl-2H-pyrazole-3-carboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 1,3-dimethyl-1H-pyrazole-5-carboxylic acid as starting materials, MS (LC/MS): 425.6 (M+H).

Example 14

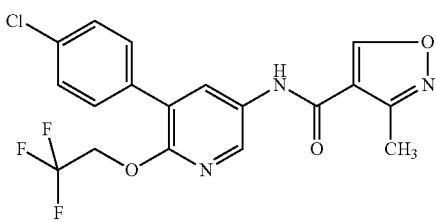 [SMILES: Cc1nocc1C(=O)Nc1cnc(OCC(F)(F)F)c(-c2ccc(Cl)cc2)c1]

Preparation of 3-methyl-isoxazole-4-carboxylic acid [5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 3-methyl-4-isoxazolecarboxylic acid as starting materials, MS (LC/MS): 412.2 (M+H).

Example 15

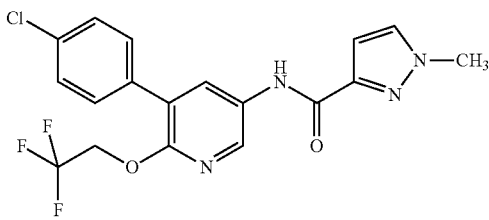 [SMILES: Cn1ccc(C(=O)Nc2cnc(OCC(F)(F)F)c(-c3ccc(Cl)cc3)c2)n1]

Preparation of 1-methyl-1H-pyrazole-3-carboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 1-methyl-1H-Pyrazole-3-carboxylic acid as starting materials, MS (LC/MS): 411.0 (M+H).

Example 16

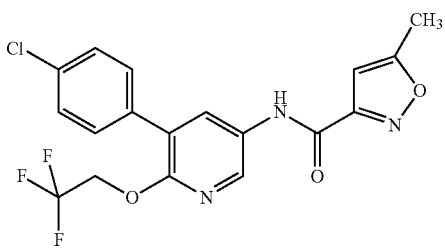 [SMILES: Cc1cc(C(=O)Nc2cnc(OCC(F)(F)F)c(-c3ccc(Cl)cc3)c2)no1]

Preparation of 5-methyl-3-isoxazolecarboxylic acid [5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoroethoxy)-pyridin-3-ylamine and 5-methyl-3-isoxazolecarboxylic acid as starting materials, MS (LC/MS): 412.2 (M+H).

Example 17

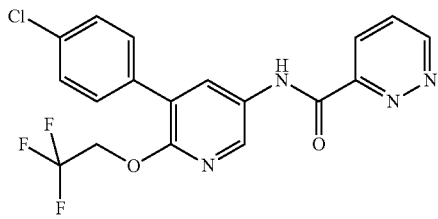 [SMILES: O=C(Nc1cnc(OCC(F)(F)F)c(-c2ccc(Cl)cc2)c1)c1cccnn1]

Preparation of 3-pyridazinecarboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 3-pyridazinecarboxylic acid as starting materials, MS (LC/MS): 409.0 (M+H).

Example 18

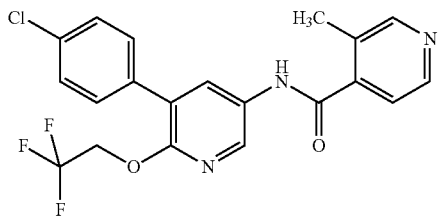 [SMILES: Cc1cnccc1C(=O)Nc1cnc(OCC(F)(F)F)c(-c2ccc(Cl)cc2)c1]

Preparation of N-[5-(4-chloro-phenyl)-6-(2,2,2-trifluoro-ethoxy)-pyridin-3-yl]-3-methyl-4-pyridinecarboxylic acid amide The title compound was synthesized in analogy to Example 1, using 5-(4-chloro-phenyl)-6-(2,2, 2-trifluoro-ethoxy)-pyridin-3-ylamine and 3-methyl-4-pyridinecarboxylic acid as starting materials, MS (LC/MS): 422.0 (M+H).

Example 19

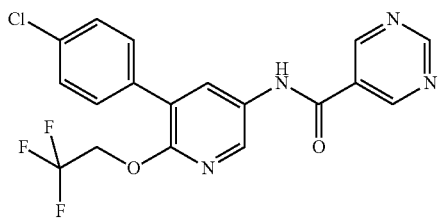 [SMILES: O=C(Nc1cnc(OCC(F)(F)F)c(-c2ccc(Cl)cc2)c1)c1cncnc1]

Preparation of 5-pyrimidinecarboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 5-pyrimidinecarboxylic acid as starting materials, MS (LC/MS): 409.0 (M+H).

Example 20

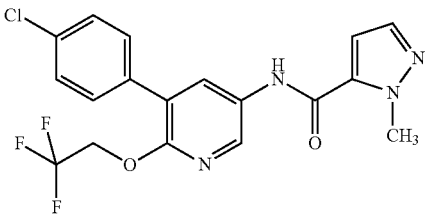 [SMILES: Cn1nccc1C(=O)Nc1cnc(OCC(F)(F)F)c(-c2ccc(Cl)cc2)c1]

Preparation of 1-methyl-1H-pyrazole-5-carboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 1-methyl-1H-pyrazole-5-carboxylic acid, as starting materials, MS (LC/MS): 409.2 (M−H).

Example 21

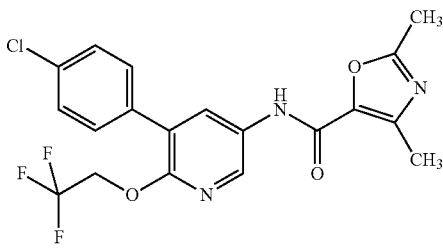 [SMILES: Cc1nc(C)c(C(=O)Nc2cnc(OCC(F)(F)F)c(-c3ccc(Cl)cc3)c2)o1]

Preparation of 2,4-dimethyl-5-oxazolecarboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoroethoxy)-pyridin-3-ylamine and 2,4-dimethyl-5-oxazolecarboxylic acid, as starting materials, MS (LC/MS): 426.2 (M+H).

Example 22

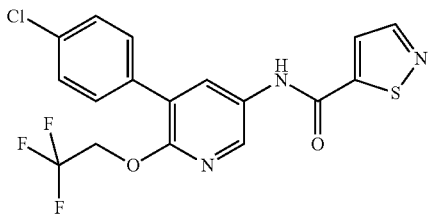 [SMILES: O=C(Nc1cnc(OCC(F)(F)F)c(-c2ccc(Cl)cc2)c1)c1ccns1]

Preparation of 5-isothiazolecarboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 5-isothiazolecarboxylic acid as starting materials, MS (LC/MS): 414.0 (M+H).

Example 23

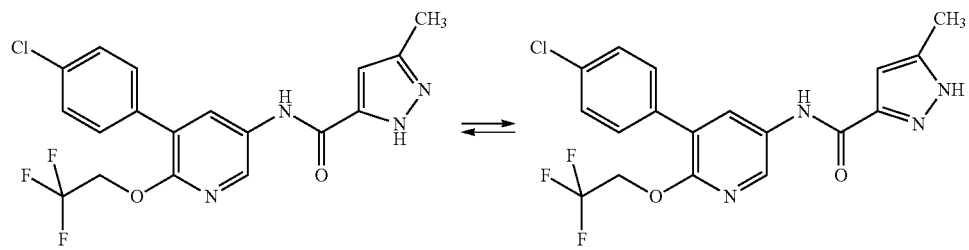 [SMILES: Cc1cc(C(=O)Nc2cnc(OCC(F)(F)F)c(-c3ccc(Cl)cc3)c2)[nH]n1 ; Cc1cc(C(=O)Nc2cnc(OCC(F)(F)F)c(-c3ccc(Cl)cc3)c2)n[nH]1]

Preparation of 5-methyl-1H-pyrazole-3-carboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 5-methyl-1H-pyrazole-3-carboxylic acid as starting materials, MS (LC/MS): 409.2 (M–H).

Example 24

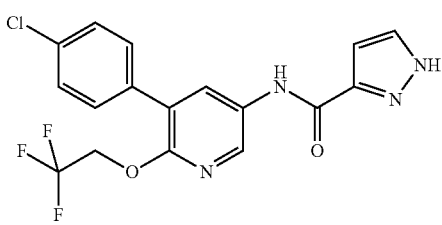 [SMILES: O=C(Nc1cnc(OCC(F)(F)F)c(-c2ccc(Cl)cc2)c1)c1cc[nH]n1]

Preparation of 1H-pyrazole-3-carboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 1H-pyrazole-3-carboxylic acid as starting materials, MS (LC/MS): 395.2 (M–H).

Example 25

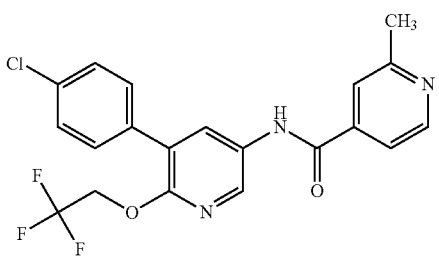 [SMILES: Cc1cc(C(=O)Nc2cnc(OCC(F)(F)F)c(-c3ccc(Cl)cc3)c2)ccn1]

Preparation of N-[5-(4-chloro-phenyl)-6-(2,2,2-trifluoro-ethoxy)-pyridin-3-yl]-2-methyl-4-pyridinecarboxylic acid amide The title compound was synthesized in analogy to Example 1, using 5-(4-chloro-phenyl)-6-(2,2, 2-trifluoro-ethoxy)-pyridin-3-ylamine and 2-methyl-4-pyridinecarboxylic acid, as starting materials, MS (LC/MS): 422.0 (M+H).

Example 26

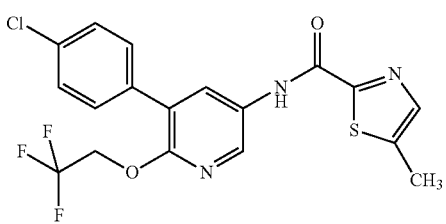 [SMILES: Cc1cnc(C(=O)Nc2cnc(OCC(F)(F)F)c(-c3ccc(Cl)cc3)c2)s1]

Preparation of 5-methyl-2-thiazole-carboxylic acid [5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoroethoxy)-pyridin-3-ylamine and 5-methyl-2-thiazolecarboxylic acid, as starting materials, MS (LC/MS): 428.2 (M+H).

Example 27

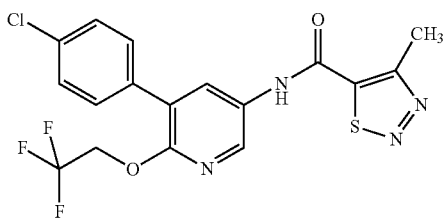 [SMILES: Cc1nnsc1C(=O)Nc1cnc(OCC(F)(F)F)c(-c2ccc(Cl)cc2)c1]

Preparation of 4-methyl-1,2,3-thiadiazole-5-carboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 4-methyl-1,2,3-thiadiazole-5-carboxylic acid, as starting materials, MS (LC/MS): 429.2 (M+H).

Example 28

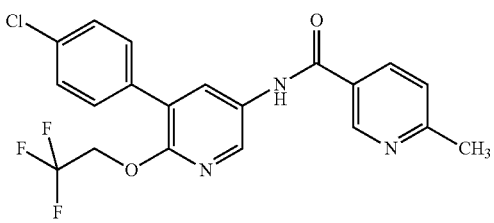 [SMILES: Cc1ccc(C(=O)Nc2cnc(OCC(F)(F)F)c(-c3ccc(Cl)cc3)c2)cn1]

Preparation of N-[5-(4-chloro-phenyl)-6-(2,2,2-trifluoro-ethoxy)-pyridin-3-yl]-6-methyl-3-pyridinecarboxylic acid amide The title compound was synthesized in analogy to Example 1, using 5-(4-chloro-phenyl)-6-(2,2, 2-trifluoro-ethoxy)-pyridin-3-ylamine and 6-methyl-3-pyridinecarboxylic acid as starting materials, MS (LC/MS): 420.4 (M−H).

Example 29

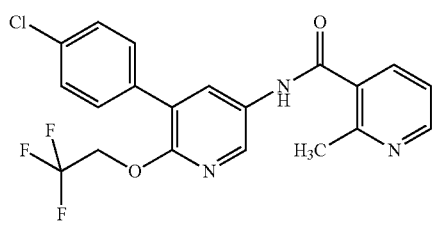 [SMILES: Cc1ncccc1C(=O)Nc1cnc(OCC(F)(F)F)c(-c2ccc(Cl)cc2)c1]

Preparation of N-[5-(4-chloro-phenyl)-6-(2,2,2-trifluoro-ethoxy)-pyridin-3-yl]-2-methyl-3-pyridinecarboxylic acid amide The title compound was synthesized in analogy to Example 1, using 5-(4-chloro-phenyl)-6-(2,2, 2-trifluoro-ethoxy)-pyridin-3-ylamine and 2-methyl-3-pyridinecarboxylic acid as starting materials, MS (LC/MS): 421.8 (M+H).

Example 30

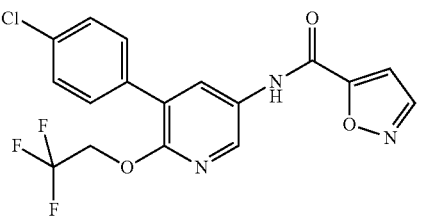 [SMILES: O=C(Nc1cnc(OCC(F)(F)F)c(-c2ccc(Cl)cc2)c1)c1ccno1]

Preparation of 5-isoxazolecarboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 5-isoxazolecarboxylic acid as starting materials, MS (LC/MS): 398.0 (M+H).

Example 31

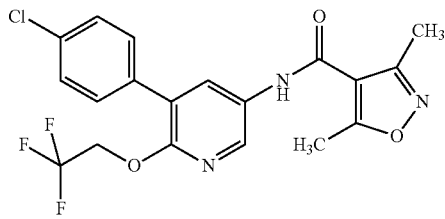 [SMILES: Cc1noc(C)c1C(=O)Nc1cnc(OCC(F)(F)F)c(-c2ccc(Cl)cc2)c1]

Preparation of 3,5-dimethyl-4-isoxazolecarboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoroethoxy)-pyridin-3-ylamine and 3,5-dimethyl-4-isoxazole-carboxylic acid, as starting materials, MS (LC/MS): 426.2 (M+H).

Example 32

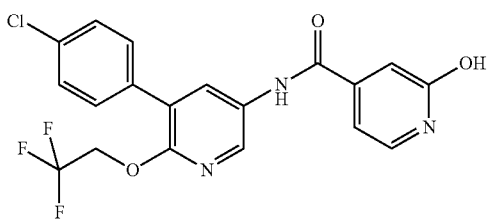 [SMILES: O=C(Nc1cnc(OCC(F)(F)F)c(-c2ccc(Cl)cc2)c1)c1ccnc(O)c1]

Preparation of N-[5-(4-chloro-phenyl)-6-(2,2,2-trifluoro-ethoxy)-pyridin-3-yl]-1,2-dihydro-2-oxo-4-pyridinecarboxylic acid amide The title compound was synthesized in analogy to Example 1, using 5-(4-chloro-phenyl)-6-(2,2, 2-trifluoro-ethoxy)-pyridin-3-ylamine and 1,2-dihydro-2-oxo-4-pyridinecarboxylic acid, as starting materials, MS (LC/MS): 424.0 (M+H).

Example 33

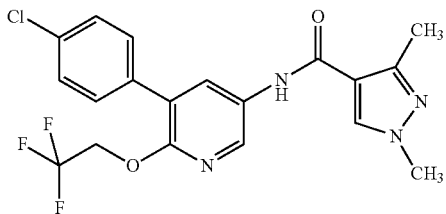 [SMILES: Cc1nn(C)cc1C(=O)Nc1cnc(OCC(F)(F)F)c(-c2ccc(Cl)cc2)c1]

Preparation of 1,3-dimethyl-1H-pyrazole-4-carboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 1,3-dimethyl-1H-pyrazole-4-carboxylic acid as starting materials, MS (LC/MS): 425.0 (M+H).

Example 34

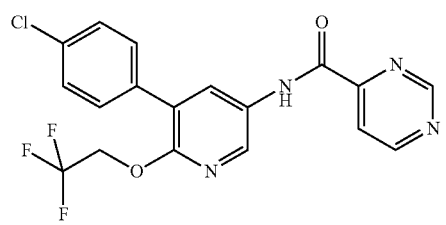 [SMILES: O=C(Nc1cnc(OCC(F)(F)F)c(-c2ccc(Cl)cc2)c1)c1ccncn1]

Preparation of 4-pyrimidinecarboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 4-pyrimidinecarboxylic acid as starting materials, MS (LC/MS): 409.0 (M+H).

Example 35

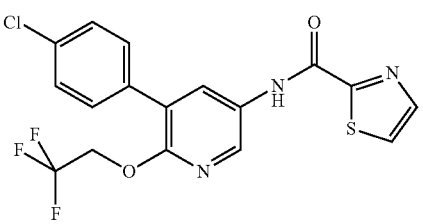 [SMILES: O=C(Nc1cnc(OCC(F)(F)F)c(-c2ccc(Cl)cc2)c1)c1nccs1]

Preparation of 2-thiazolecarboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 2-thiazolecarboxylic acid as starting materials, MS (LC/MS): 414.0 (M+H).

Example 36

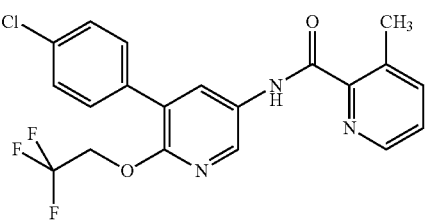 [SMILES: Cc1cccnc1C(=O)Nc1cnc(OCC(F)(F)F)c(-c2ccc(Cl)cc2)c1]

Preparation of 3-methyl-2-pyridinecarboxylic acid [5-(4-chloro-phenyl)-6-(2,2, 2-trifluoro-ethoxy)-pyridin-3-yl]-amide The title compound was synthesized in analogy to Example 1, using 5-(4-chloro-phenyl)-6-(2,2, 2-trifluoroethoxy)-pyridin-3-ylamine and 3-methyl-2-pyridinecarboxylic acid as starting materials, MS (LC/MS): 422.0 (M+H).

Example 37

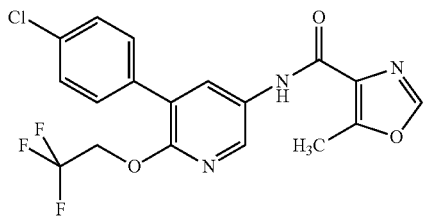 [SMILES: Cc1ocnc1C(=O)Nc1cnc(OCC(F)(F)F)c(-c2ccc(Cl)cc2)c1]

Preparation of 5-methyl-4-oxazolecarboxylic acid[5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 5-methyl-4-oxazolecarboxylic acid as starting materials, MS (LC/MS): 412.2 (M+H).

Example 38

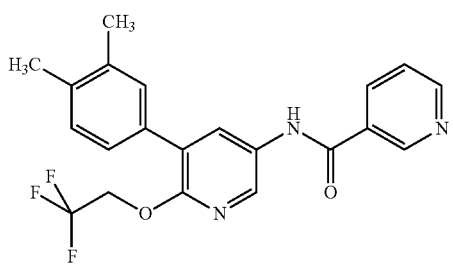 [SMILES: Cc1ccc(-c2cc(NC(=O)c3cccnc3)cnc2OCC(F)(F)F)cc1C]

Preparation of N-(5-(3,4-dimethylphenyl)-6-(2,2,2-trifluoroethoxy)pyridin-3-yl)nicotinamide In a 25 mL sealed tube N-(5-bromo-6-(2,2,2-trifluoroethoxy)pyridin-3-yl)nicotinamide (200 mg, 532 µmol) was combined with toluene (11 mL). Under argon atmosphere, were added 3.4-dimethylbenzeneboronic acid (160 mg, 1.06 mmol), an aqueous solution of sodium carbonate (2M, 0.53 mL) and Pd(dppf)$_2$Cl$_2$ (12 mg, 0.016 mmol). After two hours at 90° C., the dark red suspension was cooled to room temperature, diluted with ethyl acetate (10 mL), and washed with water (10 mL) and brine (10 mL). The aqueous layer was back-extracted with ethyl acetate (15 mL). The organic layers were dried over MgSO$_4$ and concentrated in vacuo. Crystallization from ethyl acetate/heptane (5 mL, 1/2) gave a white solid (96 mg), the filtrate was evaporated to dryness and purified by column chromatography (silica gel, 20 g, 10% to 100% ethyl acetate in heptane) to get a second part of the desired product as a white solid (139 mg). Overall yield was 65%; MS (EI): 402.3 (M+H).

Example 39

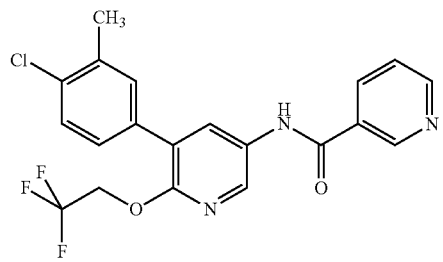 [SMILES: Cc1cc(-c2cc(NC(=O)c3cccnc3)cnc2OCC(F)(F)F)ccc1Cl]

Preparation of N-(5-(4-chloro-3-methylphenyl)-6-(2,2,2-trifluoroethoxy)pyridin-3-yl)nicotin-amide In a 25 ml sealed tube N-(5-bromo-6-(2,2,2-trifluoroethoxy)pyridin-3-yl)nicotinamide (520 mg, 1.38 mmol) was combined with toluene (20 mL). Under argon atmosphere, were added 4-chloro-3-methylphenylboronic acid (471 mg, 2.77 mmol), an aqueous solution of sodium carbonate (2M, 1.38 mL) and Pd(dppf)$_2$Cl$_2$ (30 mg, 0.041 mmol). After two hours at 90° C., the dark re suspension was cooled to room temperature, diluted with ethyl acetate (10 mL), and washed with water (10 mL) and brine (10 mL). The aqueous layer was back-extracted with ethyl acetate (15 mL). The organic layers were dried over MgSO$_4$ and concentrated in vacuo. The crude material (760 mg) was purified by flash chromatography (silica gel, 20 g, 20% to 100% ethyl acetate in heptane) to give the title compound as a light brown solid (575 mg, 98%); MS (EI): 422.8 (M+H).

Example 40

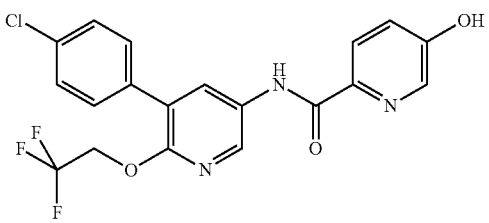 [SMILES: O=C(Nc1cnc(OCC(F)(F)F)c(-c2ccc(Cl)cc2)c1)c1ccc(O)cn1]

Preparation of 5-hydroxy-pyridine-2-carboxylic acid [5-(4-chloro-phenyl)-6-(2,2,2-trifluoro-ethoxy)-pyridin-3-yl]-amide The title compound was synthesized in analogy to Example 1, using 5-(4-chloro-phenyl)-6-(2,2, 2-trifluoro-ethoxy)-pyridin-3-ylamine and 5-hydroxy-2-pyridinecarboxylic acid (CAN 15069-92-8) as starting materials; LC-MS (UV peak area/ESI) 96.3%, 422.0523 (M−H)⁻.

Example 41

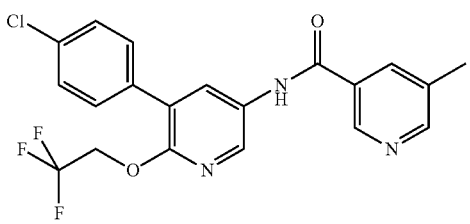 [SMILES: Cc1cncc(C(=O)Nc2cnc(OCC(F)(F)F)c(-c3ccc(Cl)cc3)c2)c1]

Preparation of N-(5-(4-chlorophenyl)-6-(2,2,2-trifluoroethoxy)pyridin-3-yl)-5-methylnicotin-amide The title compound was synthesized in analogy to Example 1, using 5-(4-chloro-phenyl)-6-(2,2, 2-trifluoroethoxy)-pyridin-3-ylamine and 5-methyl-3-pyridinecarboxylic acid (CAN 3222-49-9) as starting materials; MS (EI) 422.1 (M+H)⁺.

Example 42

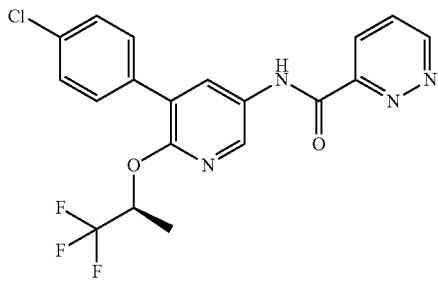 [SMILES: C[C@H](Oc1ncc(NC(=O)c2cccnn2)cc1-c1ccc(Cl)cc1)C(F)(F)F]

Preparation of (S)-N-(5-(4-chlorophenyl)-6-(1,1,1-trifluoropropan-2-yloxy)pyridin-3-yl)pyridazine-3-carboxamide a) 5-Chloro-3-(4-chloro-phenyl)-2-fluoro-pyridine

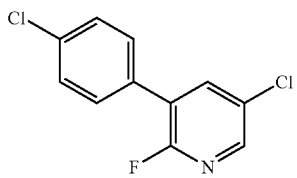 [SMILES: Fc1ncc(Cl)cc1-c1ccc(Cl)cc1]

A mixture of 3-bromo-5-chloro-2-fluoro-pyridine, (CAN 884494-87-5; 2.0 g, 9.50 mmol), 4-chlorophenylboronic acid (CAN 1679-18-1; 1.5 g, 9.50 mmol); tetrakis(triphenylphoshine)-palladium (0.55 g, 0.48 mmol) and potassium carbonate (2.6 g, 19 mmol) in water (50 mL) and THF (50 mL) was heated at reflux temperature for 18 h. The reaction mixture was cooled, diluted with ethyl acetate, phases were separated and the water phase was extracted with ethyl acetate. The organic phases were pooled, dried with MgSO4 and the solvent was removed in vacuo. The residue was purified by column chromatography (on silica gel with a gradient of heptane to heptane:ethyl acetate=9:1 to yield the title product (2.2 g, 95%) as white solid; MS (ESI): 241.0 (M)⁺.

b) 5-Chloro-3-(4-chloro-phenyl)-2-((S)-2,2,2-trifluoro-1-methyl-ethoxy)-pyridine

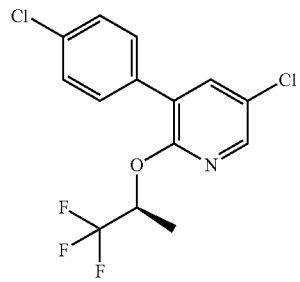 [SMILES: C[C@H](Oc1ncc(Cl)cc1-c1ccc(Cl)cc1)C(F)(F)F]

To a mixture of 1.133 g (S)-1,1,1-trifluoro-2-propanol in 10 ml dry DMF 397 mg sodium hydride (60%) was added and the mixture was stirred at room temperature for 30 minutes. The resulting solution was added dropwise at RT to a solution of 2.185 g 5-chloro-3-(4-chloro-phenyl)-2-fluoro-pyridine in 20ml dry DMF. The reaction mixture was then stirred at room temperature for 2 h. The resulting light yellow mixture was partitioned between water and ethyl acetate, the phases were separated. The organic phase was dried over MgSO₄ and purified by chromatography on silica gel with a gradient of heptane to heptane : ethyl acetate=9 : 1 to yield 2.330 g (76.80%) of the title compound as colourless liquid; MS (ESI) 336.1(M+H)⁺.

c) (S)-Methyl 5-(4-chlorophenyl)-6-(1,1,1-trifluoropropan-2-yloxy)nicotinate

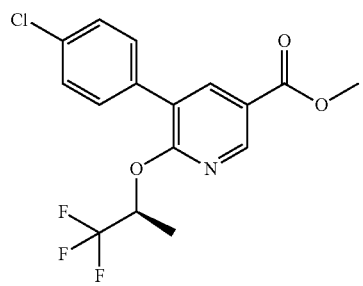 [SMILES: COC(=O)c1cnc(O[C@@H](C)C(F)(F)F)c(-c2ccc(Cl)cc2)c1]

To a solution of 2.42 g 5-chloro-3-(4-chloro-phenyl)-2-((S)-2,2,2-trifluoro-1-methyl-ethoxy)-pyridine in 50 mL methanol was added 1.09 g triethylamine and 0.484 g PdCl₂.dppf.CH₂Cl₂. The mixture was heated to 150° C. under an atmosphere of 70 bar carbon monoxide for 20 h. The reaction mixture was cooled to room temperature. The solids were removed by filtration and the mother liquor was evaporated and purified by chromatography on silica gel using a gradient of heptane to heptane:ethyl acetate 85:15 to yield 0.862g (33%) of the title compound as a light yellow oil; MS (ESI) 359 (M⁺).

d) (S)-5-(4-Chlorophenyl)-6-(1,1,1-trifluoropropan-2-yloxy)nicotinic acid

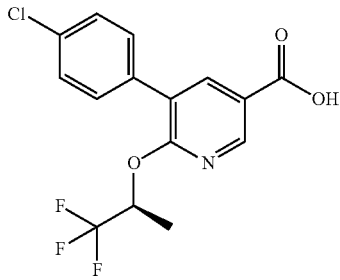 [SMILES: C[C@H](Oc1ncc(C(=O)O)cc1-c1ccc(Cl)cc1)C(F)(F)F]

To a solution of 0.860 g (S)-methyl 5-(4-chlorophenyl)-6-(1,1,1-trifluoropropan-2-yloxy)nicotinate in 9 mL tetrahydrofuran was added 3 mL of a 1M solution of lithium hydroxide in water and the mixture was stirred at room temperature overnight. The solvent was evaporated and the residue was acidified by addition of 1M hydrochloric acid till pH=2. Ethyl acetate was added and the phases were separated. The organic phase was dried over MgSO₄ and the solvent was removed to yield 830 mg (100%) of the title compound as light yellow solid; MS (ESI) 344.1 (M−H)⁻.

e) [5-(4-Chloro-phenyl)-6-((S)-2,2,2-trifluoro-1-methyl-ethoxy)-pyridin-3-yl]-carbamic acid tert-butyl ester

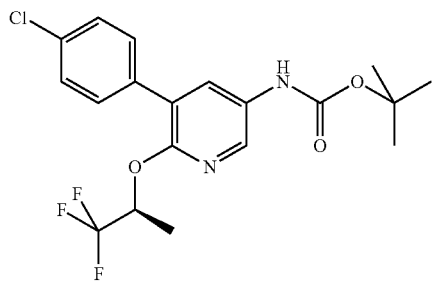 [SMILES: C[C@H](Oc1ncc(NC(=O)OC(C)(C)C)cc1-c1ccc(Cl)cc1)C(F)(F)F]

(S)-5-(4-Chlorophenyl)-6-(1,1,1-trifluoropropan-2-yloxy)nicotinic acid (0.300 g, 868 µmol) was suspended in t-butanol (3.0 mL). DPPA (358 mg, 282 µl), and triethylamine (87.8 mg, 120 µl, 868 µmol) were added and the reaction mixture was stirred at 100° C. overnight. The mixture was cooled to room temperature, extracted with ethyl acetate and sodium carbonate solution, the organic phase was dried with MgSO₄ and concentrated in vacuo. The crude material was purified by flash chromatography (silica gel, 20 g, 5% to 25% ethyl acetate in heptane) to give 0.36 g (99%) of the title compound as white solid; MS (EI) 417.3 (M+H)⁺.

f) 5-(4-Chloro-phenyl)-6-((S)-2,2,2-trifluoro-1-methyl-ethoxy)-pyridin-3-ylamine

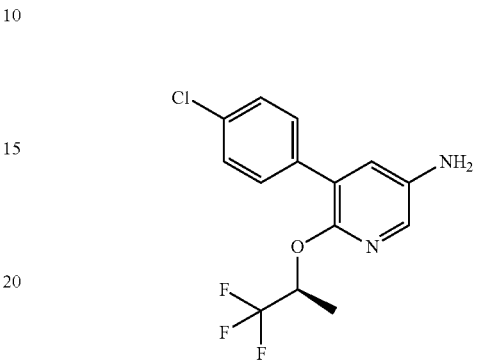

Trifluoroacetic acid (2.74 g, 1.85 ml, 24.0 mmol) was added to (S)-tert-butyl 5-(4-chlorophenyl)-6-(1,1,1-trifluoropropan-2-yloxy)pyridin-3-ylcarbamate (0.350 g, 840 µmol). The resulting yellow solution was stirred at RT for 1 h. The solvent was evaporated. The residue was partitioned between ethyl acetate and 1M Na₂CO₃ solution, the organic phase was dried with MgSO₄ and concentrated in vacuo. The crude material was purified by flash chromatography (silica gel, 20 g, 5 to 50% EtOAc in heptane) to give 0.22 g (82%) of the title compound as light brown oil; MS (EI) 317.1 (M+H)⁺.

g) (S)-N-(5-(4-chlorophenyl)-6-(1,1,1-trifluoropropan-2-yloxy)pyridin-3-yl)pyridazine-3-carboxamide

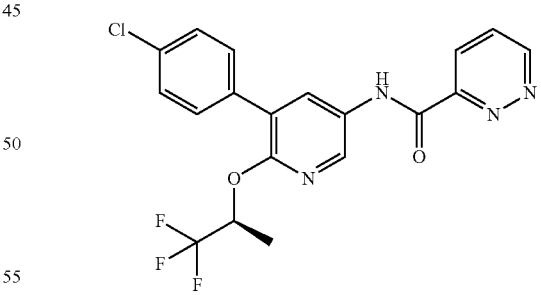

Pyridazine-3-carboxylic acid (CAN 2164-61-6; 43.1 mg, 347 µmol) was suspended in DMF (1.0 mL). TBTU (112 mg, 347 µmol), ethyldiisopropylamine (102 mg, 131 µl, 789 µmol,) and 5-(4-chloro-phenyl)-6-((S)-2,2,2-trifluoro-1-methyl-ethoxy)-pyridin-3-ylamine (0.100 g, 316 µmol) were added and the reaction mixture was stirred at room temperature for 1 h. The rection mixture was extracted with ethyl acetate and 1M citric acid solution; the organic phase was dried with MgSO₄ and concentrated in vacuo. The crude material was purified by flash chromatography (silica gel, 10 g, 10% to 50% ethyl acetate in heptane) to give 0.11 g (83%) of the title compound as white solid; MS (EI) 423.1 (M+H)⁺.

Example 43

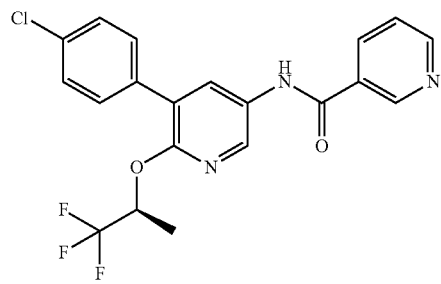 [SMILES: C[C@H](Oc1ncc(NC(=O)c2cccnc2)cc1-c1ccc(Cl)cc1)C(F)(F)F]

Preparation of (S)-N-(5-(4-chlorophenyl)-6-(1,1,1-trifluoropropan-2-yloxy)pyridin-3-yl)nicotinamide The title compound was synthesized in analogy to Example 42g, using 5-(4-chloro-phenyl)-6-((S)-2,2,2-trifluoro-1-methyl-ethoxy)-pyridin-3-ylamine (example 42c) and 3-pyridine carboxylic acid (CAN 59-67-6) as starting materials; MS (EI) 422.0 (M+H)⁺.

Example 44

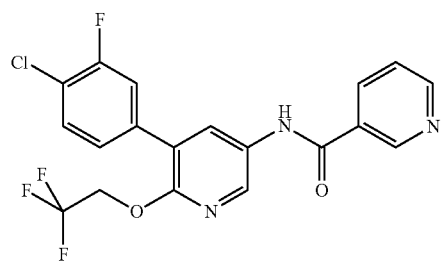 [SMILES: O=C(Nc1cnc(OCC(F)(F)F)c(-c2ccc(Cl)c(F)c2)c1)c1cccnc1]

Preparation of N-(5-(4-chloro-3-fluorophenyl)-6-(2,2,2-trifluoroethoxy)pyridin-3-yl)nicotin-amide The title compound was synthesized in analogy to Example 39, using N45-bromo-6-(2,2,2-trifluoro-ethoxy)-pyridin-3-yl]-nicotinamide (example G) and B-(4-chloro-3-fluorophenyl)-boronic acid (CAN 137504-86-0) as starting materials; LC-MS (UV peak area/ESI) 96.4%, 424.0482 (M–H)⁻.

Example 45

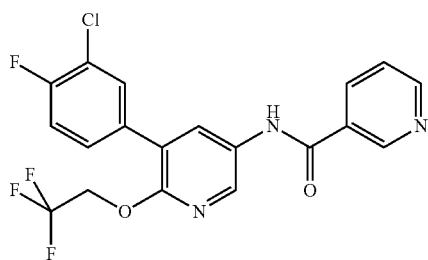 [SMILES: O=C(Nc1cnc(OCC(F)(F)F)c(-c2ccc(F)c(Cl)c2)c1)c1cccnc1]

Preparation of N-(5-(3-chloro-4-fluorophenyl)-6-(2,2,2-trifluoroethoxy)pyridin-3-yl)nicotin-amide The title compound was synthesized in analogy to Example 39, using N45-bromo-6-(2,2,2-trifluoro-ethoxy)-pyridin-3-yl]-nicotinamide (example G) and B-(3-chloro-4-fluorophenyl)-boronic acid (CAN 144432-85-9) as starting materials; LC-MS (UV peak area/ESI) 98.0%, 424.0483 (M-H)⁻

Example 46

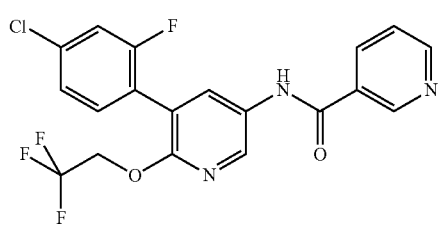 [SMILES: O=C(Nc1cnc(OCC(F)(F)F)c(-c2ccc(Cl)cc2F)c1)c1cccnc1]

Preparation of N-(5-(4-chloro-2-fluorophenyl)-6-(2,2,2-trifluoroethoxy)pyridin-3-yl)nicotin-amide The title compound was synthesized in analogy to Example 39, using N45-bromo-6-(2,2,2-trifluoro-ethoxy)-pyridin-3-yl]-nicotinamide (example G) and B-(4-chloro-2- fluorophenyl)-boronic acid (CAN 160591-91-3) as starting materials; LC-MS (UV peak area/ESI) 97.2%, 424.0483 (M−H)⁻.

Example 47

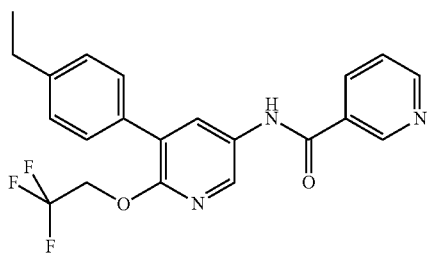 [SMILES: CCc1ccc(-c2cc(NC(=O)c3cccnc3)cnc2OCC(F)(F)F)cc1]

Preparation of N-(5-(4-ethylphenyl)-6-(2,2,2-trifluoroethoxy)pyridin-3-yl)nicotinamide The title compound was synthesized in analogy to Example 39, using N45-bromo-6-(2,2,2-trifluoro-ethoxy)-pyridin-3-yl]-nicotinamide (example G) and B-(4-ethylphenyl)-boronic acid (CAN 63139-21-9) as starting materials; LC-MS (UV peak area/ESI) 100%, 402.1409 (M+H)⁺.

Example 48

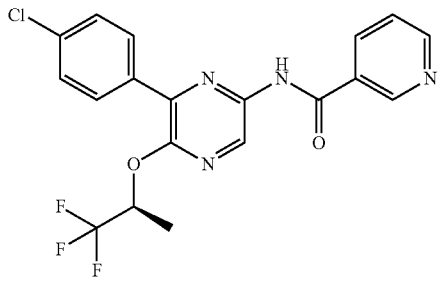

Preparation of (S)-N-(6-(4-chlorophenyl)-5-(1,1,1-trifluoropropan-2-yloxy)pyrazin-2-yl)nicotinamide a) 6-(4-Chloro-phenyl)-5-((S)-2,2,2-trifluoro-1-methyl-ethoxy)-pyrazine-2-carboxylic acid methyl ester

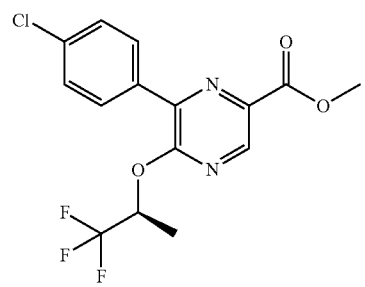 [SMILES: COC(=O)c1cnc(O[C@@H](C)C(F)(F)F)c(-c2ccc(Cl)cc2)n1]

5-Bromo-6-(4-chlorophenyl)-2-pyrazinecarboxylic acid methyl ester (CAN 960247-79-4, 2.420 g, 7.39 mmol) was dissolved in dry DMSO (25 mL). Cesium carbonate (4.41 g, 8.13 mmol) and (S)-1,1,1-trifluoropropan-2-ol (927 mg, 8.13 mmol) were added and the reaction mixture was stirred at room temperature for 2 h. The mixture was partitioned between water and ethyl acetate; the organic phase was dried with MgSO₄ and concentrated in vacuo. The crude residue was purified by flash chromatography (silica gel, 100 g, 10% to 50% ethyl acetate in heptane) to yield 2.53 g (95%) of the title compound as yellow oil; MS (EI) 361.1 (M+H)⁺.

b) 6-(4-Chloro-phenyl)-5-((S)-2,2,2-trifluoro-1-methyl-ethoxy)-pyrazine-2-carboxylic acid

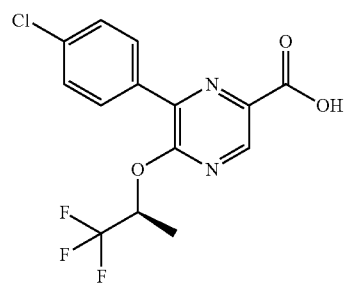

The title compound was synthesized in analogy to Example 42d, using 6-(4-chloro-phenyl)-5-((S)-2,2,2-trifluoro-1-methyl-ethoxy)-pyrazine-2-carboxylic acid methyl ester as starting material; MS (ESI) 345.0 (M−H)⁻.

c) [6-(4-Chloro-phenyl)-5-((S)-2,2,2-trifluoro-1-methyl-ethoxy)-pyrazin-2-yl]-carbamic acid tert-butyl ester

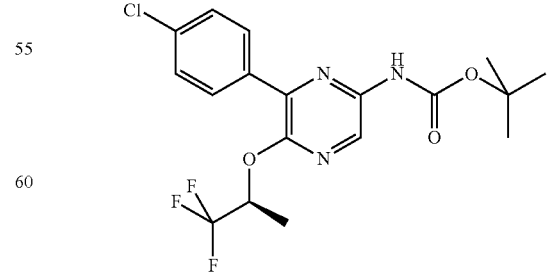

The title compound was synthesized in analogy to Example 42e, using 6-(4-chloro-phenyl)-5-((S)-2,2,2-trifluoro-1-methyl-ethoxy)-pyrazine-2-carboxylic acid as starting material; MS (EI) 418.2 (M+H)⁺.

d) 6-(4-Chloro-phenyl)-5-((S)-2,2,2-trifluoro-1-methyl-ethoxy)-pyrazin-2-ylamine

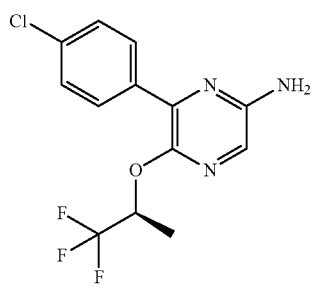 [SMILES: C[C@H](Oc1ncc(N)nc1-c1ccc(Cl)cc1)C(F)(F)F]

The title compound was synthesized in analogy to Example 42f, using [6-(4-chloro-phenyl)-5-((S)-2,2,2-trifluoro-1-methyl-ethoxy)-pyrazin-2-yl]-carbamic acid tert-butyl ester as starting material; MS (EI) 318.0 (M+H)⁺.

e) (S)-N-(6-(4-chlorophenyl)-5-(1,1,1-trifluoropropan-2-yloxy)pyrazin-2-yl)nicotinamide

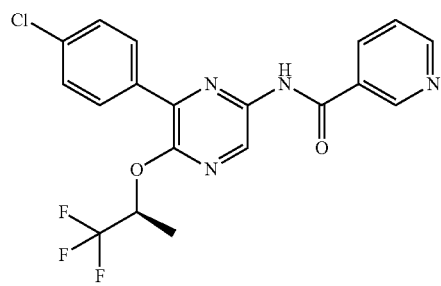 [SMILES: C[C@H](Oc1ncc(NC(=O)c2cccnc2)nc1-c1ccc(Cl)cc1)C(F)(F)F]

6-(4-Chloro-phenyl)-5-((S)-2,2,2-trifluoro-1-methyl-ethoxy)-pyrazin-2-ylamine (0.100 g, 315 µmol) was dissolved in dried pyridine (1.0 mL), nicotinoyl chloride hydrochloride (61.6 mg, 346 µmol) was added and the suspension was stirred at 140° C. for 10 minutes in the microwave. The solvent was evaporated and the crude material was purified by flash chromatography (silica gel, 10 g, 0% to 50% CH₂Cl₂/ MeOH/NH₃ 9/1/0.1) to give 0.121 g (91%) of the title compound as white solid; LC-MS (UV peak area/ESI) 100%, 423.0821 (M+H)⁺.

Example 49

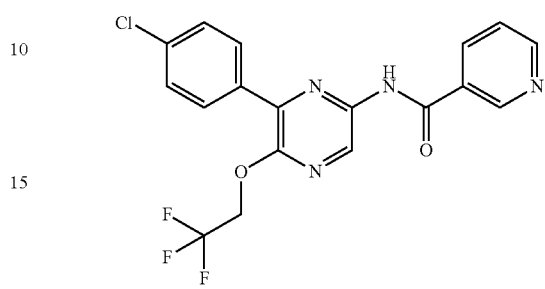

Preparation of N-(6-(4-chlorophenyl)-5-(2,2,2-trifluoroethoxy)pyrazin-2-yl)nicotinamide a) 6-(4-Chloro-phenyl)-5-(2,2,2-trifluoro-ethoxy)-pyrazine-2-carboxylic acid methyl ester

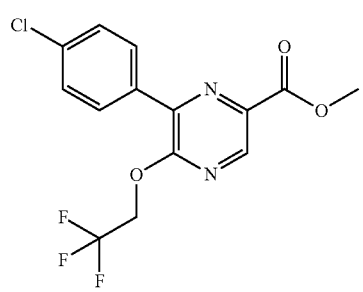 [SMILES: COC(=O)c1cnc(OCC(F)(F)F)c(-c2ccc(Cl)cc2)n1]

The title compound was synthesized in analogy to Example 48a, using 5-bromo-6-(4-chlorophenyl)-2-pyrazinecarboxylic acid methyl ester (CAN 960247-79-4) and 2,2,2-trifluoroethanol as starting materials; MS (EI) 347.1 (M+H)⁺.

b) 6-(4-Chloro-phenyl)-5-(2,2,2-trifluoro-ethoxy)-pyrazine-2-carboxylic acid

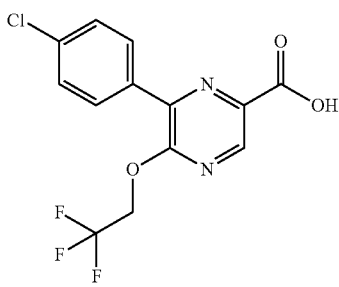 [SMILES: O=C(O)c1cnc(OCC(F)(F)F)c(-c2ccc(Cl)cc2)n1]

The title compound was synthesized in analogy to Example 42d, using 6-(4-chloro-phenyl)-5-(2,2,2-trifluoroethoxy)-pyrazine-2-carboxylic acid methyl ester as starting material; MS (ESI) 331.1 (M–H)⁻.

c) [6-(4-Chloro-phenyl)-5-(2,2,2-trifluoro-ethoxy)-pyrazin-2-yl]-carbamic acid tert-butyl ester

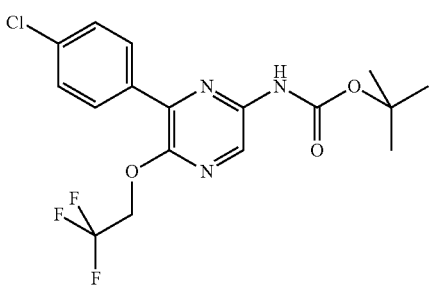 [SMILES: CC(C)(C)OC(=O)Nc1cnc(OCC(F)(F)F)c(-c2ccc(Cl)cc2)n1]

The title compound was synthesized in analogy to Example 42e, using 6-(4-chloro-phenyl)-5-(2,2,2-trifluoro-ethoxy)-pyrazine-2-carboxylic acid as starting material; MS (EI) 404.3 (M+H)⁺.

d) 6-(4-Chloro-phenyl)-5-(2,2,2-trifluoro-ethoxy)-pyrazin-2-ylamine

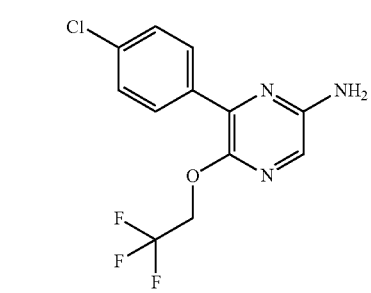 [SMILES: Nc1cnc(OCC(F)(F)F)c(-c2ccc(Cl)cc2)n1]

The title compound was synthesized in analogy to Example 42f, using [6-(4-chloro-phenyl)-5-(2,2,2-trifluoro-ethoxy)-pyrazin-2-yl]-carbamic acid tert-butyl ester as starting material; MS (EI) 304.0 (M+H)⁺.

e) N-(6-(4-Chlorophenyl)-5-(2,2,2-trifluoroethoxy)pyrazin-2-yl)nicotinamide

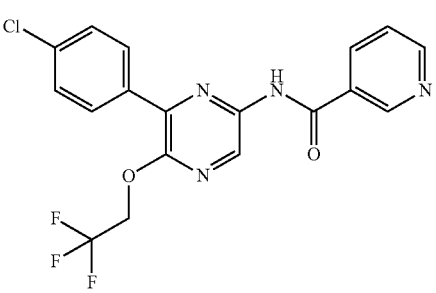 [SMILES: O=C(Nc1cnc(OCC(F)(F)F)c(-c2ccc(Cl)cc2)n1)c1cccnc1]

The title compound was synthesized in analogy to Example 48e, using 6-(4-chloro-phenyl)-5-(2,2,2-trifluoro-ethoxy)-pyrazin-2-ylamine (example 49d) and nicotinoyl chloride hydrochloride as starting materials; LC-MS (UV peak area/ESI) 95.7%, 407.0532 (M–H)⁻.

Example 50

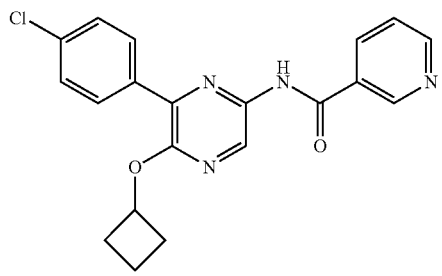 [SMILES: O=C(Nc1cnc(OC2CCC2)c(-c2ccc(Cl)cc2)n1)c1cccnc1]

Preparation of N-(6-(4-chlorophenyl)-5-cyclobutoxy-pyrazin-2-yl)nicotinamide a) 6-(4-Chloro-phenyl)-5-cyclopropylmethoxy-pyrazine-2-carboxylic acid

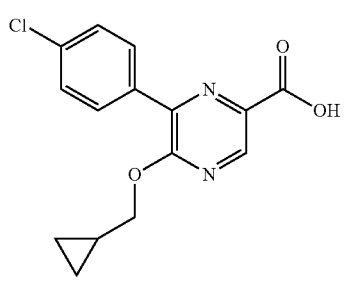 [SMILES: O=C(O)c1cnc(OCC2CC2)c(-c2ccc(Cl)cc2)n1]

Cyclopropylmethanol (1.54 g, 1.73 ml, 21.3 mmol) was diluted in dried DMF (15 mL); sodium hydride (512 mg, 21.3 mmol) was added in portions and the reaction mixture was stirred at room temperature for 15 minutes. The resulting solution was added slowly at <5° C. to a solution of 5-bromo-6-(4-chlorophenyl)pyrazine-2-carboxylic acid (CAN 960247-80-7; 3.040 g, 9.7 mmol) in dried DMF (15 mL). The reaction mixture was stirred at room temperature for 30 minutes; water was added and the mixture was acidified with 1M HCl solution to pH=2. The mixture was extracted with ethyl acetate; organic phases were combined, dried with MgSO₄ and concentrated in vacuo. The crude did still contain starting material and was dissolved again in 15 mL DMF; a solution of cyclopropylmethanol (1.05 g, 1.18 ml, 14.5 mmol) and sodium hydride (582 mg, 14.5 mmol) in 15 mL DMF was added and the mixture was stirred at room temperature for 3 hours. Water was added and the reaction mixture was acidified with 1M HCl solution to pH 2; the product precipitated to give 2.55 g (86%) of the title compound as light yellow solid; MS (ESI) 303.2 (M−H)⁻.

b) [6-(4-Chloro-phenyl)-5-cyclopropylmethoxy-pyrazin-2-yl]-carbamic acid tert-butyl ester

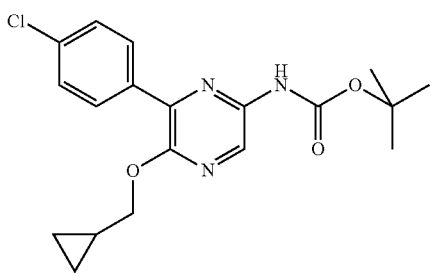 [SMILES: CC(C)(C)OC(=O)Nc1cnc(OCC2CC2)c(-c2ccc(Cl)cc2)n1]

The title compound was synthesized in analogy to Example 42e, using 6-(4-Chloro-phenyl)-5-cyclopropyl-methoxy-pyrazine-2-carboxylic acid (example 50a) as starting material; MS (EI) 376.3 (M+H)⁺.

c) 6-(4-Chloro-phenyl)-5-cyclobutoxy-pyrazin-2-ylamine

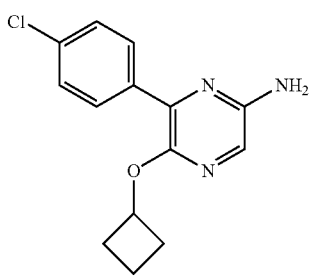 [SMILES: Nc1cnc(OC2CCC2)c(-c2ccc(Cl)cc2)n1]

TFA (14.8 g, 10 mL, 130 mmol) was added to [6-(4-chloro-phenyl)-5-cyclopropylmethoxy-pyrazin-2-yl]-carbamic acid tert-butyl ester (example 50b, 1.365 g, 3.63 mmol). The resulting yellow solution was stirred at room temperature for 1 h. The solvent was evaporated and the residue was partitioned between ethyl acetate and 1M Na₂CO₃ solution; the organic phases were combined, dried with MgSO₄ and concentrated in vacuo. The crude material was purified by flash chromatography (silica gel, 100g, 10% to 50% ethyl acetate in heptane; then ethyl acetate/methanol 9/1 to give 0.133 g (13%) of the title compound (by rearrangement) as yellow oil; MS (EI) 276.1 (M+H)⁺.

d) N-(6-(4-Chlorophenyl)-5-cyclobutoxypyrazin-2-yl)nicotinamide

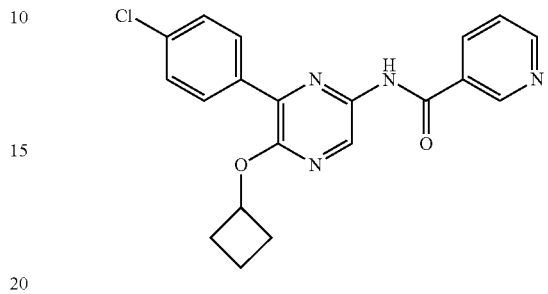

The title compound was synthesized in analogy to Example 48 e, using 6-(4-chloro-phenyl)-5-cyclobutoxy-pyrazin-2-ylamine (example 50c) and nicotinoyl chloride hydrochloride as starting materials; LC-MS (UV peak area/ ESI) 97.4%, 381.1096 (M+H)⁺.

Example 51

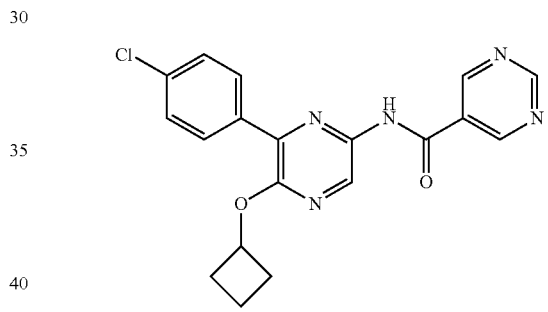

Preparation of N-(6-(4-chlorophenyl)-5-cyclobutoxy-pyrazin-2-yl)pyrimidine-5-carboxamide The title compound was synthesized in analogy to Example 42g, using 6-(4-chloro-phenyl)-5-cyclobutoxy-pyrazin-2-ylamine (example 50c) and 5-pyrimidinecarboxylic acid (CAN 4595-61-3) as starting materials; LC-MS (UV peak area/ESI) 96.3%, 482.1073 (M+H)⁺.

Example 52

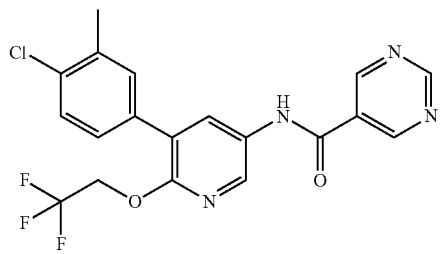 [SMILES: Cc1cc(-c2cc(NC(=O)c3cncnc3)cnc2OCC(F)(F)F)ccc1Cl]

Preparation of N-(5-(4-chloro-3-methylphenyl)-6-(2,2,2-trifluoroethoxy)pyridin-3-yl)pyrimidine-5-carboxamide a) Pyrimidine-5-carboxylic acid[5-bromo-6-(2,2,2-trifluoro-ethoxy)-pyridin-3-yl]-amide

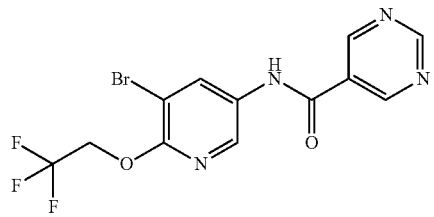 [SMILES: O=C(Nc1cnc(OCC(F)(F)F)c(Br)c1)c1cncnc1]

The title compound was synthesized in analogy to Example 42 g, using 5-bromo-6-(2,2,2-trifluoro-ethoxy)-pyridin-3-ylamine (example D) and 5-pyrimidinecarboxylic acid (CAN 4595-61-3) as starting materials; MS (ESI) 375.2 (M−H)⁻.

b) N-(5-(4-Chloro-3-methylphenyl)-6-(2,2,2-trifluoroethoxy)pyridin-3-yl)pyrimidine-5-carboxamide

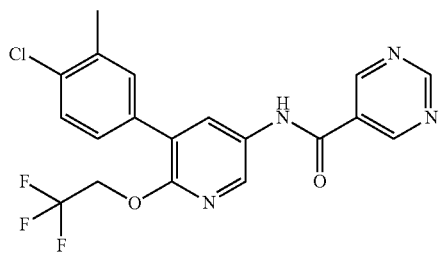 [SMILES: Cc1cc(-c2cc(NC(=O)c3cncnc3)cnc2OCC(F)(F)F)ccc1Cl]

The title compound was synthesized in analogy to Example 39, using pyrimidine-5-carboxylic acid[5-bromo-6-(2,2,2-trifluoro-ethoxy)-pyridin-3-yl]-amide (example 52 a) and B-(4-chloro-3-methylphenyl)-boronic acid (CAN 161950-10-3) as starting materials; LC-MS (UV peak area/ESI) 100%, 421.0698 (M−H)⁻.

Example 53

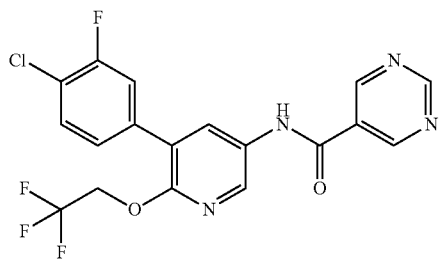 [SMILES: O=C(Nc1cnc(OCC(F)(F)F)c(-c2ccc(Cl)c(F)c2)c1)c1cncnc1]

Preparation of N-(5-(4-chloro-3-fluorophenyl)-6-(2,2,2-trifluoroethoxy)pyridin-3-yl)pyrimidine-5-carboxamide The title compound was synthesized in analogy to Example 39, using pyrimidine-5-carboxylic acid[5-bromo-6-(2,2,2-trifluoro-ethoxy)-pyridin-3-yl]-amide (example 52 a) and B-(4-chloro-3-fluorophenyl)-boronic acid (CAN 137504-86-0) as starting materials; LC-MS (UV peak area/ESI) 97.7%, 425.0448 (M−H)⁻.

Example 54

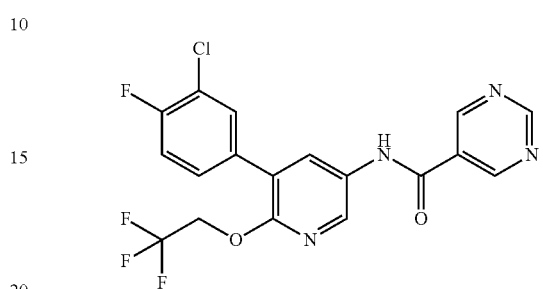

Preparation of N-(5-(3-chloro-4-fluorophenyl)-6-(2,2,2-trifluoroethoxy)pyridin-3-yl)pyrimidine-5-carboxamide The title compound was synthesized in analogy to Example 39, using pyrimidine-5-carboxylic acid[5-bromo-6-(2,2,2-trifluoro-ethoxy)-pyridin-3-yl]-amide (example 52 a) and B-(3-chloro-4-fluorophenyl)-boronic acid (CAN 144432-85-9) as starting materials; LC-MS (UV peak area/ESI) 93.5%, 425.0449 (M−H)⁻.

Example 55

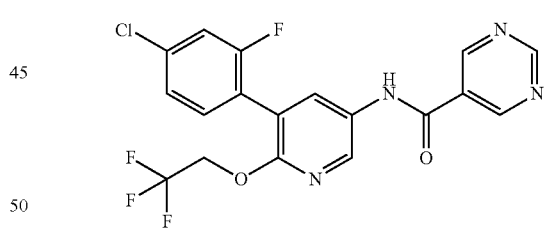

Preparation of N-(5-(4-chloro-2-fluorophenyl)-6-(2,2,2-trifluoroethoxy)pyridin-3-yl)pyrimidine-5-carboxamide The title compound was synthesized in analogy to Example 39, using pyrimidine-5-carboxylic acid[5-bromo-6-(2,2,2-trifluoro-ethoxy)-pyridin-3-yl]-amide (example 52 a) and B-(4-chloro-2-fluorophenyl)-boronic acid (CAN 160591-91-3) as starting materials; LC-MS (UV peak area/ ESI) 92.2%, 425.0446 (M–H)⁻.

Example 56

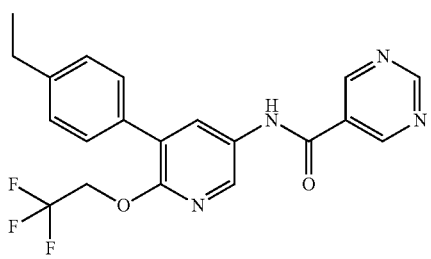 [SMILES: CCc1ccc(-c2cc(NC(=O)c3cncnc3)cnc2OCC(F)(F)F)cc1]

Preparation of N-(5-(4-ethylphenyl)-6-(2,2,2-trifluoroethoxy)pyridin-3-yl)pyrimidine-5-carboxamide The title compound was synthesized in analogy to Example 39, using pyrimidine-5-carboxylic acid[5-bromo-6-(2,2,2-trifluoro-ethoxy)-pyridin-3-yl]-amide (example 52 a) and B-(4-ethylphenyl)-boronic acid (CAN 63139-21-9) as starting materials; LC-MS (UV peak area/ESI) 100%, 403.1384 (M+H)⁺.

Example 57

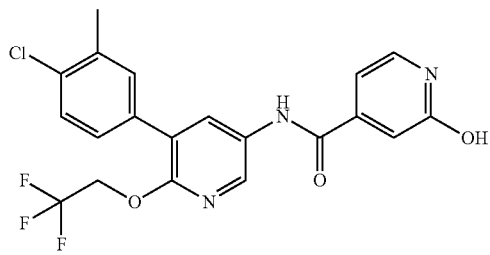 [SMILES: Cc1cc(-c2cc(NC(=O)c3ccnc(O)c3)cnc2OCC(F)(F)F)ccc1Cl]

Preparation of N-(5-(4-chloro-3-methylphenyl)-6-(2,2,2-trifluoroethoxy)pyridin-3-yl)-2-hydroxyisonicotinamide a) 5-(4-Chloro-3-methyl-phenyl)-6-(2,2,2-trifluoroethoxy)-pyridin-3-ylamine

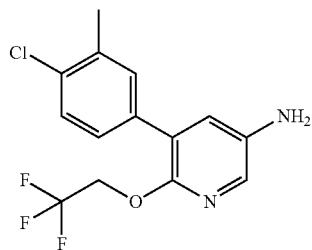 [SMILES: Cc1cc(-c2cc(N)cnc2OCC(F)(F)F)ccc1Cl]

The title compound was synthesized in analogy to Example 39, using 5-bromo-6-(2,2,2-trifluoro-ethoxy)-pyridin-3-ylamine (example D) and B-(4-chloro-3-methylphenyl)-boronic acid (CAN 161950-10-3) as starting materials; MS (EI) 317.0 (M+H)⁺.

b) N-(5-(4-Chloro-3-methylphenyl)-6-(2,2,2-trifluoroethoxy)pyridin-3-yl)-2-hydroxyisonicotinamide

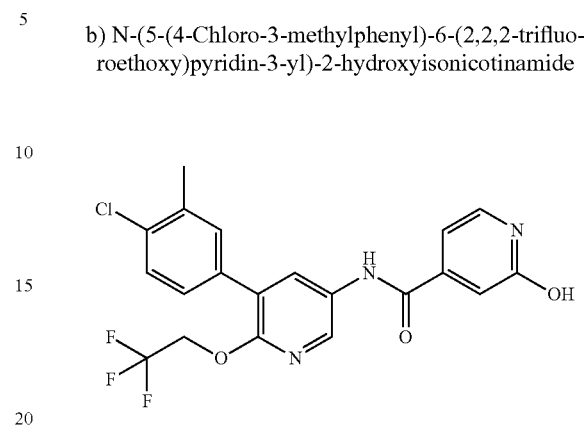

The title compound was synthesized in analogy to Example 42 g, using 5-(4-Chloro-3-methyl-phenyl)-6-(2,2,2-trifluoro-ethoxy)-pyridin-3-ylamine (example 57 a) and 1,2-dihydro-2-oxo-4-pyridinecarboxylic acid (CAN 22282-72-0) as starting materials; LC-MS (UV peak area/ESI) 100%, 436.0689 (M–H)⁻.

Example 58

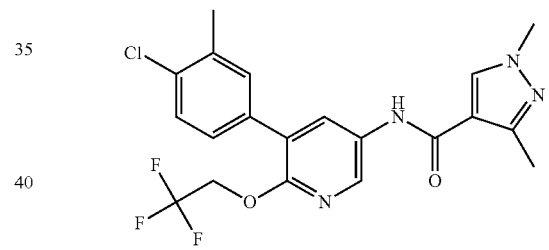

Preparation of N-(5-(4-chloro-3-methylphenyl)-6-(2,2,2-trifluoroethoxy)pyridin-3-yl)-1,3-dimethyl-1H-pyrazole-4-carboxamide a) 1,3-Dimethyl-1H-pyrazole-4-carboxylic acid[5-bromo-6-(2,2,2-trifluoro-ethoxy)-pyridin-3-yl]-amid

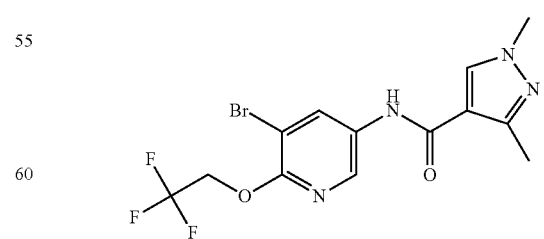

The title compound was synthesized in analogy to Example 42 g, using 5-bromo-6-(2,2,2-trifluoro-ethoxy)-pyridin-3-ylamine (example D) and 1,3-dimethyl-1H-pyrazole- 4-carboxylic acid (CAN 78703-53-4) as starting materials; LC-MS (UV peak area/ESI) 100%, 393.0063 (M−H)⁻.

b) N-(5-(4-chloro-3-methylphenyl)-6-(2,2,2-trifluoroethoxy)pyridin-3-yl)-1,3-dimethyl-1H-pyrazole-4-carboxamide

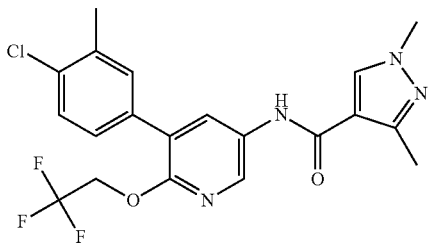 [SMILES: Cc1cc(-c2cc(NC(=O)c3cn(C)nc3C)cnc2OCC(F)(F)F)ccc1Cl]

The title compound was synthesized in analogy to Example 39, using 1,3-dimethyl-1H-pyrazole-4-carboxylic acid[5-bromo-6-(2,2,2-trifluoro-ethoxy)-pyridin-3-yl]-amide (example 58 a) and B-(4-chloro-3-methylphenyl)-boronic acid (CAN 161950-10-3) as starting materials; LC-MS (UV peak area/ESI) 96.1%, 439.1154 (M+H)⁺.

Example 59

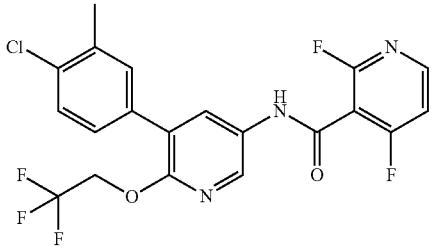 [SMILES: Cc1cc(-c2cc(NC(=O)c3c(F)ccnc3F)cnc2OCC(F)(F)F)ccc1Cl]

Preparation of N-(5-(4-chloro-3-methylphenyl)-6-(2,2,2-trifluoroethoxy)pyridin-3-yl)-2,4-difluoronicotinamide The title compound was synthesized in analogy to Example 42 g, using 5-(4-chloro-3-methyl-phenyl)-6-(2,2,2-trifluoro-ethoxy)-pyridin-3-ylamine (example 57 a) and 2,4-difluoro-3-pyridinecarboxylic acid (CAN 849937-90-2) as starting materials; MS (EI) 458.2 (M+H)⁺.

Example 60

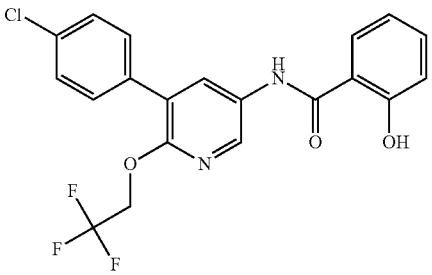 [SMILES: O=C(Nc1cnc(OCC(F)(F)F)c(-c2ccc(Cl)cc2)c1)c1ccccc1O]

Preparation of N-(5-(4-chlorophenyl)-6-(2,2,2-trifluoroethoxy)pyridin-3-yl)-2-hydroxy-benzamide The title compound was synthesized in analogy to Example 42 g, using 5-(4-chloro-phenyl)-6-(2, 2,2-trifluoroethoxy)-pyridin-3-ylamine (example E) and 2-hydroxy-benzoic acid (CAN 69-72-7) as starting materials; LC-MS (UV peak area/ESI) 97.7%, 421.5080 (M−H)⁻.

Example 61

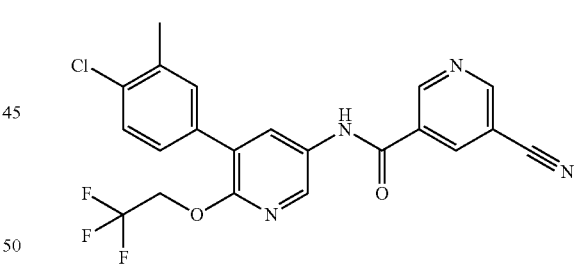

Preparation of N-(5-(4-chloro-3-methylphenyl)-6-(2, 2,2-trifluoroethoxy)pyridin-3-yl)-5-cyanonicotinamide The title compound was synthesized in analogy to Example 42 g, using 5-(4-chloro-3-methyl-phenyl)-6-(2,2,2-trifluoro-ethoxy)-pyridin-3-ylamine (example 57 a) and 5-cyano-3-pyridinecarboxylic acid, (CAN 887579-62-6) as starting materials; LC-MS (UV peak area/ESI) 98.7%, 445.0693 (M−H)⁻.

Example 62

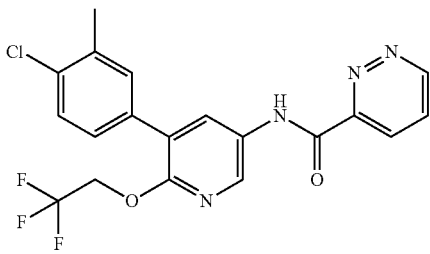 [SMILES: Cc1cc(-c2cc(NC(=O)c3cccnn3)cnc2OCC(F)(F)F)ccc1Cl]

Preparation of N-(5-(4-chloro-3-methylphenyl)-6-(2,2,2-trifluoroethoxy)pyridin-3-yl)pyridazine-3-carboxamide a) Pyridazine-3-carboxylic acid[5-bromo-6-(2,2,2-trifluoro-ethoxy)-pyridin-3-yl]-amide

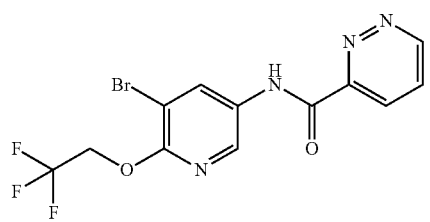 [SMILES: O=C(Nc1cnc(OCC(F)(F)F)c(Br)c1)c1cccnn1]

The title compound was synthesized in analogy to Example 42 g, using 5-bromo-6-(2,2,2-trifluoro-ethoxy)-pyridin-3-ylamine (example D) and 3-pyridazinecarboxylic acid (CAN 2164-61-6) as starting materials; MS (ESI) 375.2 (M−H)⁻.

b) N-(5-(4-Chloro-3-methylphenyl)-6-(2,2,2-trifluoroethoxy)pyridin-3-yl)pyridazine-3-carboxamide

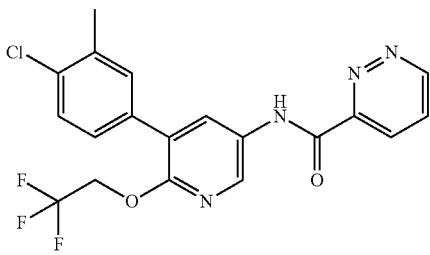 [SMILES: Cc1cc(-c2cc(NC(=O)c3cccnn3)cnc2OCC(F)(F)F)ccc1Cl]

The title compound was synthesized in analogy to Example 39, using pyridazine-3-carboxylic acid[5-bromo-6-(2,2,2-trifluoro-ethoxy)-pyridin-3-yl]-amide (example 62 a) and B-(4-chloro-3-methylphenyl)-boronic acid (CAN 161950-10-3) as starting materials; LC-MS (UV peak area/ESI) 94.2%, 423.0828 (M+H)⁺.

Example 63

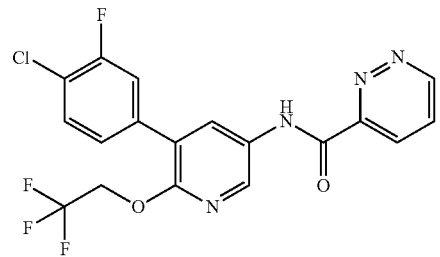 [SMILES: O=C(Nc1cnc(OCC(F)(F)F)c(-c2ccc(Cl)c(F)c2)c1)c1cccnn1]

Preparation of N-(5-(4-chloro-3-fluorophenyl)-6-(2,2,2-trifluoroethoxy)pyridin-3-yl)pyridazine-3-carboxamide The title compound was synthesized in analogy to Example 39, using pyridazine-3-carboxylic acid[5-bromo-6-(2,2,2-trifluoro-ethoxy)-pyridin-3-yl]-amide (example 62 a) and B-(4-chloro-3-fluorophenyl)-boronic acid (CAN 137504-86-0) as starting materials; LC-MS (UV peak area/ESI) 100%, 425.0438 (M−H)⁻.

Example 64

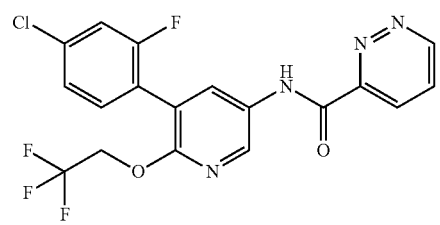 [SMILES: O=C(Nc1cnc(OCC(F)(F)F)c(-c2ccc(Cl)cc2F)c1)c1cccnn1]

Preparation of N-(5-(4-chloro-2-fluorophenyl)-6-(2,2,2-trifluoroethoxy)pyridin-3-yl)pyridazine-3-carboxamide The title compound was synthesized in analogy to Example 39, using pyridazine-3-carboxylic acid[5-bromo-6-(2,2,2-trifluoro-ethoxy)-pyridin-3-yl]-amide (example 62 a) and B-(4-chloro-2-fluorophenyl)-boronic acid (CAN 160591-91-3) as starting materials; LC-MS (UV peak area/ ESI) 98.7%, 427.0587 (M+H)+.

Example 65

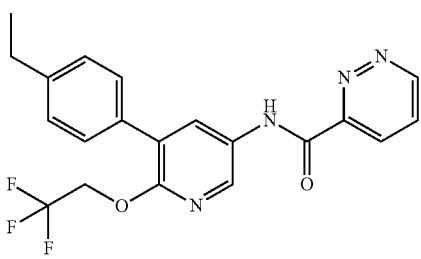 [SMILES: CCc1ccc(-c2cc(NC(=O)c3cccnn3)cnc2OCC(F)(F)F)cc1]

Preparation of N-(5-(4-ethylphenyl)-6-(2,2,2-trifluoroethoxy)pyridin-3-yl)pyridazine-3-carboxamide The title compound was synthesized in analogy to Example 39, using pyridazine-3-carboxylic acid[5-bromo-6-(2,2,2-trifluoro-ethoxy)-pyridin-3-yl]-amide (example 62 a) and B-(4-ethylphenyl)-boronic acid (CAN 63139-21-9) as starting materials; LC-MS (UV peak area/ESI) 98.9%, 403.1386 (M+H)+.

Example 66

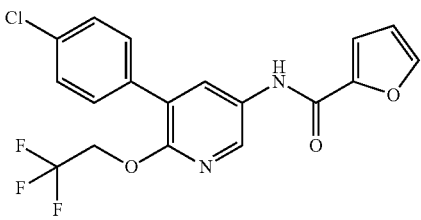 [SMILES: O=C(Nc1cnc(OCC(F)(F)F)c(-c2ccc(Cl)cc2)c1)c1ccco1]

Preparation of N-(5-(4-chlorophenyl)-6-(2,2,2-trifluoroethoxy)pyridin-3-yl)furan-2-carboxamide The title compound was synthesized in analogy to Example 42 g, using 5-(4-chloro-phenyl)-6-(2,2,2-trifluoroethoxy)-pyridin-3-ylamine (example E) and 2-furancarboxylic acid (CAN 88-14-2) as starting materials; LC-MS (UV peak area/ESI) 98.0%, 397.0566 (M+H)+.

Example 67

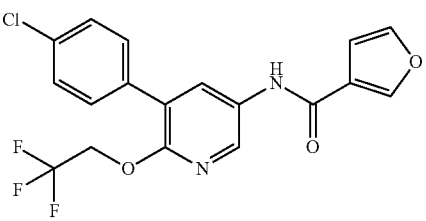 [SMILES: O=C(Nc1cnc(OCC(F)(F)F)c(-c2ccc(Cl)cc2)c1)c1ccoc1]

Preparation of N-(5-(4-chlorophenyl)-6-(2,2,2-trifluoroethoxy)pyridin-3-yl)furan-3-carboxamide The title compound was synthesized in analogy to Example 42 g, using 5-(4-chloro-phenyl)-6-(2, 2,2-trifluoroethoxy)-pyridin-3-ylamine (example E) and 3-furancarboxylic acid (CAN 488-93-7) as starting materials; LC-MS (UV peak area/ESI) 98.2%, 395.0414 (M−H)−.

Example 68

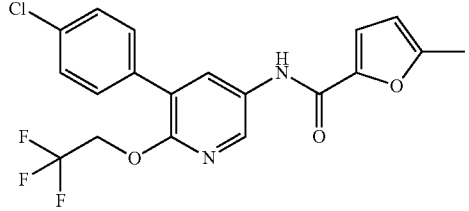 [SMILES: Cc1ccc(C(=O)Nc2cnc(OCC(F)(F)F)c(-c3ccc(Cl)cc3)c2)o1]

Preparation of N-(5-(4-chlorophenyl)-6-(2,2,2-trifluoroethoxy)pyridin-3-yl)-5-methylfuran-2-carboxamide The title compound was synthesized in analogy to Example 42 g, using 5-(4-chloro-phenyl)-6-(2,2,2-trifluoroethoxy)-pyridin-3-ylamine (example E) and 5-methyl-2-furancarboxylic acid (CAN 1917-15-3) as starting materials; LC-MS (UV peak area/ESI) 98.0%, 409.574 (M−H)−.

Example 69

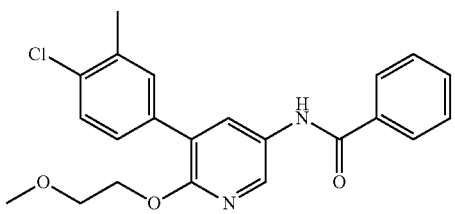 [SMILES: COCCOc1ncc(NC(=O)c2ccccc2)cc1-c1ccc(Cl)c(C)c1]

Preparation of N-(5-(4-chloro-3-methylphenyl)-6-(2-methoxyethoxy)pyridin-3-yl)benzamide a) 3-Bromo-2-(2-methoxy-ethoxy)-5-nitro-pyridine

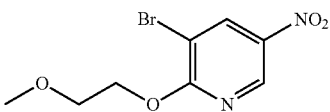

To a solution of 2-methoxyethanol (8.81 g, 9.13 ml, 116 mmol) in anhydrous THF (150ml) was added sodium hydride (4.63 g, 116 mmol) under nitrogen at 5° C. or below and the reaction mixture was stirred at 25° C. for 1 h. Then 3-bromo-2-chloro-5-nitropyridine (CAN 5470-17-7) (25 g, 105 mmol) was added drop wise at 25° C. and stirred at 25° C. for 1 h. Ice-water (150 ml) was added to the reaction mixture and extracted with ethyl acetate (500 mL). The combined organic layers was washed with water and brine, dried over Na₂SO₄ and evaporated under reduced pressure to get the crude residue (25.7 g). The crude was purified by column chromatography (15% ethyl acetate/hexane) to get the desired product (21.6 g, 74%) as light yellow solid; GC/MS (FID/EI): 100%, 276.0 (M)⁺.

b) 5-Bromo-6-(2-methoxy-ethoxy)-pyridin-3-ylamine

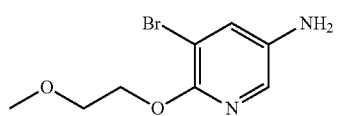

The title compound was synthesized in analogy to Example C, using 3-bromo-2-(2-methoxy-ethoxy)-5-nitro-pyridine (example 69 a) as starting material; LC-MS (UV peak area/ESI) 100%, 247.0084 (M+H)⁺.

c) 5-(4-Chloro-3-methyl-phenyl)-6-(2-methoxy-ethoxy)-pyridin-3-ylamine

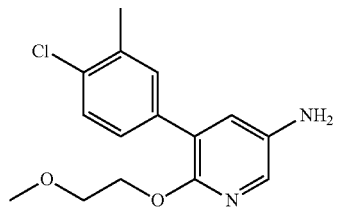 [SMILES: COCCOc1ncc(N)cc1-c1ccc(Cl)c(C)c1]

The title compound was synthesized in analogy to Example E, using 5-bromo-6-(2-methoxy-ethoxy)-pyridin-3-ylamine (example 69 b) and B-(4-chloro-3-methylphenyl)-boronic acid (CAN 161950-10-3) as starting materials; GC/MS (FID/EI): 100%, 292 (M)⁺.

d) N-(5-(4-chloro-3-methylphenyl)-6-(2-methoxy-ethoxy)pyridin-3-yl)benzamide

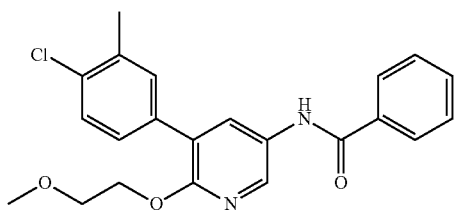 [SMILES: COCCOc1ncc(NC(=O)c2ccccc2)cc1-c1ccc(Cl)c(C)c1]

The title compound was synthesized in analogy to Example 42 g, using 5-(4-chloro-3-methyl-phenyl)-6-(2-methoxy-ethoxy)-pyridin-3-ylamine (example 69 c) and benzoic acid as starting materials; LC-MS (UV peak area/ESI) 100%, 397.1307 (M+H)⁺.

Example 70

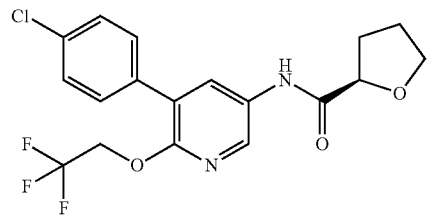 [SMILES: O=C(Nc1cnc(OCC(F)(F)F)c(-c2ccc(Cl)cc2)c1)[C@H]1CCCO1]

Preparation of (RS)-N-(5-(4-chlorophenyl)-6-(2,2,2-trifluoroethoxy)pyridin-3-yl)tetrahydrofuran-2-carboxamide The title compound was synthesized in analogy to Example 42 g, using 5-(4-chloro-phenyl)-6-(2,2,2-trifluoro-ethoxy)-pyridin-3-ylamine (example E) and tetrahydro-2-furancarboxylic acid, (CAN 16874-33-2) as starting materials; enantiomers were separated by chiral HPLC (ChiralPak AD, 30% ethanol/n-heptane (−) enantiomer isolated; LC-MS (UV peak area/ESI) 100%, 401.0868 (M+H)⁺; $\alpha_D^{20}$ (MeOH)=−16.8°

Example 71

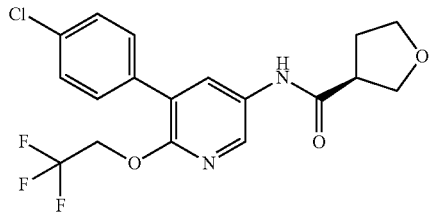 [SMILES: O=C(Nc1cnc(OCC(F)(F)F)c(-c2ccc(Cl)cc2)c1)[C@H]1CCOC1]

Preparation of (SR)-N-(5-(4-chlorophenyl)-6-(2,2,2-trifluoroethoxy)pyridin-3-yl)-tetrahydrofuran-3-carboxamide The title compound was synthesized in analogy to Example 42 g, using 5-(4-chloro-phenyl)-6-(2,2,2-trifluoro-ethoxy)-pyridin-3-ylamine (example E) and tetrahydro-3-furancarboxylic acid, (CAN 89364-31-8) as starting materials; enantiomers were separated by chiral HPLC (ChiralPak AD, 30% ethanol/n-heptane (+) enantiomer isolated; LC-MS (UV peak area/ESI) 98.1%, 401.0869 (M+H)+; α$_D^{20}$ (MeOH)=+10.1°

Example 72

Preparation of N-(5-(4-chlorophenyl)-6-(2,2,2-trifluoroethoxy)pyridin-3-yl)-4-methyl-3,4-dihydro-2H-pyrido[3,2-b][1,4]oxazine-7-carboxamide

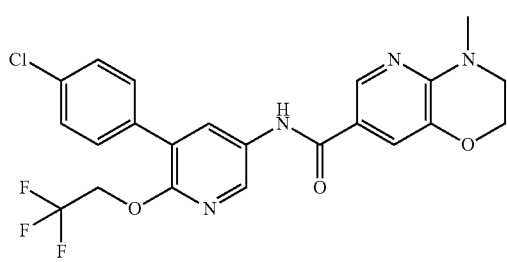 [SMILES: CN1CCOc2cc(C(=O)Nc3cnc(OCC(F)(F)F)c(-c4ccc(Cl)cc4)c3)cnc21]

The title compound was synthesized in analogy to Example 42 g, using 5-(4-chloro-phenyl)-6-(2,2,2-trifluoro-ethoxy)-pyridin-3-ylamine (example E) and 3,4-dihydro-4-methyl-2H-pyrido[3,2-b]-1,4-oxazine-7-carboxylic acid (CAN 915707-58-3) as starting materials; MS (EI) 479.2 (M+H)+.

Example 73

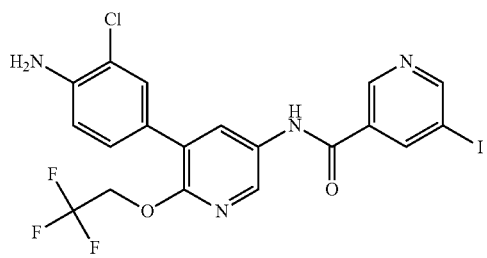 [SMILES: Nc1ccc(-c2cc(NC(=O)c3cncc(I)c3)cnc2OCC(F)(F)F)cc1Cl]

Preparation of N-(5-(4-amino-3-chlorophenyl)-6-(2,2,2-trifluoroethoxy)pyridin-3-yl)-5-iodonicotinamide a) {4-[5-Amino-2-(2,2,2-trifluoro-ethoxy)-pyridin-3-yl]-2-chloro-phenyl}-carbamic acid benzyl ester

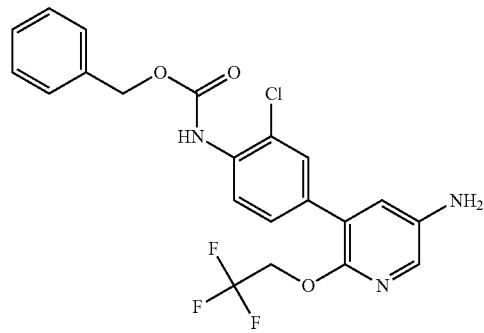 [SMILES: Nc1cnc(OCC(F)(F)F)c(-c2ccc(NC(=O)OCc3ccccc3)c(Cl)c2)c1]

The title compound was synthesized in analogy to Example E, using 5-bromo-6-(2,2,2-trifluoro-ethoxy)-pyridin-3-ylamine (example C) and N-[2-chloro-4-(4,4,5,5-tetramethyl-1,3,2-dioxaborolan-2-yl)phenyl]-carbamic acid phenylmethyl ester (CAN 1218791-42-4) as starting materials; MS (EI) 452.1 (M+H)+.

b) {2-Chloro-4-[5-[(5-iodo-pyridine-3-carbonyl)-amino]-2-(2,2,2-trifluoro-ethoxy)-pyridin-3-yl]-phenyl}-carbamic acid benzyl ester

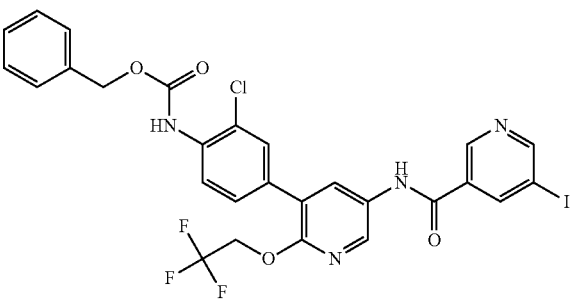 [SMILES: O=C(Nc1ccc(-c2cc(NC(=O)c3cncc(I)c3)cnc2OCC(F)(F)F)cc1Cl)OCc1ccccc1]

The title compound was synthesized in analogy to Example 42 g, using {4-[5-amino-2-(2,2,2-trifluoro-ethoxy)-pyridin-3-yl]-2-chloro-phenyl}-carbamic acid benzyl ester (example 73 a) and 5-iodo-3-pyridinecarboxylic acid (CAN 15366-65-1) as starting materials; LC-MS (UV peak area/ESI) 68.6%, 683.4 (M+H)⁺.

c) N-(5-(4-amino-3-chlorophenyl)-6-(2,2,2-trifluoroethoxy)pyridin-3-yl)-5-iodonicotinamide

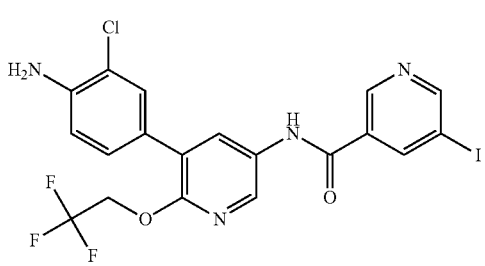 [SMILES: Nc1ccc(-c2cc(NC(=O)c3cncc(I)c3)cnc2OCC(F)(F)F)cc1Cl]

{2-Chloro-4-[5-[(5-iodo-pyridine-3-carbonyl)-amino]-2-(2,2,2-trifluoro-ethoxy)-pyridin-3-yl]-phenyl}-carbamic acid benzyl ester (87 mg, 127 µmol) was, with cooling, combined with trifluoroacetic acid (3 mL) to give a brown solution. The reaction mixture was warmed to room temperature and stirred for 72 h. The crude reaction mixture was concentrated in vacuo, poured into 50 mL ethyl acetate and extracted with 1 M NaOH (1×25 mL). The aqueous layer was washed with ethyl acetate (1×50 mL). The organic layers were combined, dried with $Na_2SO_4$ and concentrated in vacuo. The crude material was purified by flash chromatography (silica gel, 20 g, 0% to 40% EtOAc in heptane) to give the title compound (59 mg, 84%); LC-MS (UV peak area/ESI) 98.1%, 548.9795 (M+H)⁺.

Example 74

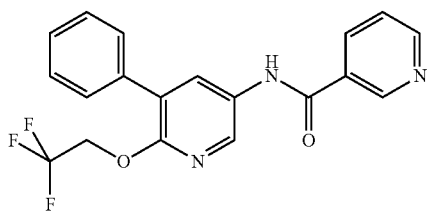 [SMILES: O=C(Nc1cnc(OCC(F)(F)F)c(-c2ccccc2)c1)c1cccnc1]

Preparation of N-(5-phenyl-6-(2,2,2-trifluoroethoxy)pyridin-3-yl)nicotinamide

The title compound was synthesized in analogy to Example 39, using N-[5-bromo-6-(2,2,2-trifluoro-ethoxy)-pyridin-3-yl]-nicotinamide (example G) and B-phenyl-boronic acid (CAN 98-80-6) as starting materials; LC-MS (UV peak area/ESI) 100%, 374.1107 (M+H)⁺.

Example 75

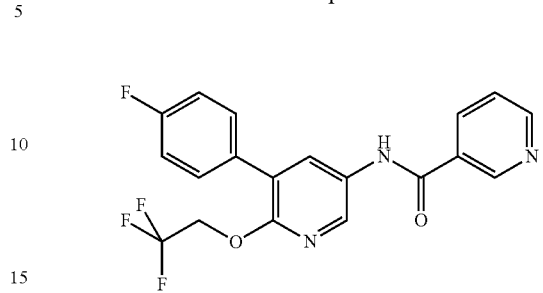

Preparation of N-(5-(4-fluorophenyl)-6-(2,2,2-trifluoroethoxy)pyridin-3-yl)nicotinamide The title compound was synthesized in analogy to Example 39, using N-[5-bromo-6-(2,2,2-trifluoro-ethoxy)-pyridin-3-yl]-nicotinamide (example G) and B-(4-fluorophenyl)-boronic acid (CAN 1765-93-1) as starting materials; LC-MS (UV peak area/ESI) 100%, 392.1005 (M+H)⁺.

Example 76

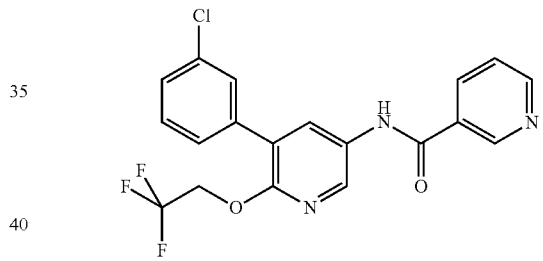

Preparation of N-(5-(3-chlorophenyl)-6-(2,2,2-trifluoroethoxy)pyridin-3-yl)nicotinamide The title compound was synthesized in analogy to Example 39, using N-[5-bromo-6-(2,2,2-trifluoro-ethoxy)-pyridin-3-yl]-nicotinamide (example G) and B-(3-chlorophenyl)-boronic acid (CAN 63503-60-6) as starting materials; LC-MS (UV peak area/ESI) 100%, 408.0719 (M+H)⁺.

Example 77

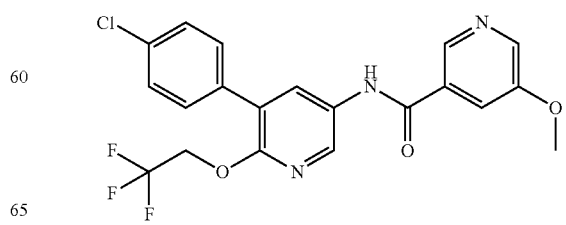

Preparation of N-(5-(4-chlorophenyl)-6-(2,2,2-trifluoroethoxy)pyridin-3-yl)-5-methoxynicotinamide The title compound was synthesized in analogy to Example 42 g, using 5-(4-chloro-phenyl)-6-(2,2,2-trifluoro-ethoxy)-pyridin-3-ylamine (example E) and 5-methoxy-3-pyridinecarboxylic acid (CAN 20826-03-3) as starting materials; LC-MS (UV peak area/ESI) 97.8%, 438.0812 (M+H)$^+$.

Example 78

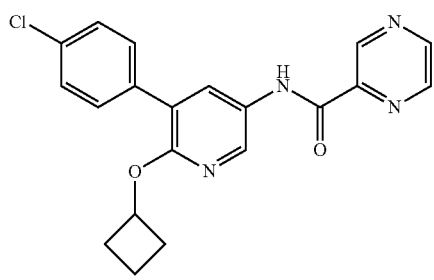 [SMILES: O=C(Nc1cnc(OC2CCC2)c(-c2ccc(Cl)cc2)c1)c1cnccn1]

Preparation of N-(5-(4-chlorophenyl)-6-cyclobutoxy-pyridin-3-yl)pyrazine-2-carboxamide a) 5-Bromo-6-cyclobutoxy-nicotinic acid

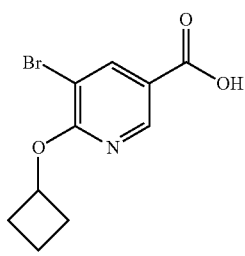 [SMILES: O=C(O)c1cnc(OC2CCC2)c(Br)c1]

5-Bromo-6-chloronicotinic acid (CAN 29241-62-1; 3 g, 12.7 mmol) was dissolved in DMSO (30 mL); cyclobutanol (1.19 g, 1.29 ml, 16.5 mmol) and potassium hydroxide (powder) (2.14 g, 38.1 mmol) were added and the reaction mixture was stirred at room temperature for 5 h. More cyclobutanol (0.5 mL) and KOH (1 g) was added and the reaction mixture was stirred at room temperature for another 2 days. Water (30 mL) was added and the mixture was acidified (cooling) with 5 mL 37% HCl in water (pH=2). The suspension was filtered and washed with water. The cake was dried in vacuo to obtain the title compound (3.1 g, 88.7%) as white solid; MS (ESI) 270.2 (M−H)$^-$.

b) 5-(4-Chloro-phenyl)-6-cyclobutoxy-nicotinic acid

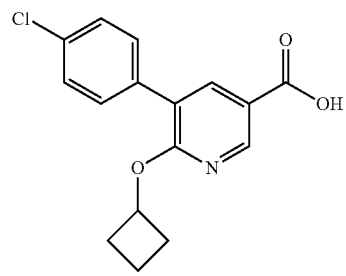 [SMILES: O=C(O)c1cnc(OC2CCC2)c(-c2ccc(Cl)cc2)c1]

5-Bromo-6-cyclobutoxy-nicotinic acid (example 78 a; 1.531 g, 5.63 mmol), 4-chloro-phenylboronic acid (968 mg, 6.19 mmol), potassium carbonate (1.56 g, 11.3 mmol) and tetrakis(triphenylphosphine)palladium (325 mg, 281 μmol) were suspended in THF (38 mL) and water (38 mL). The reaction mixture was stirred at reflux temperature (100° C.) over the weekend. THF was removed and the residue was partitioned between water (pH=2) and ethyl acetate; the organic phases were combined, dried with MgSO$_4$ and concentrated in vacuo to obtain the title compound (quant.) as off-white solid; MS (ESI) 302.2 (M−H)$^-$.

c) [5-(4-Chloro-phenyl)-6-cyclobutoxy-pyridin-3-yl]-carbamic acid tert-butyl ester

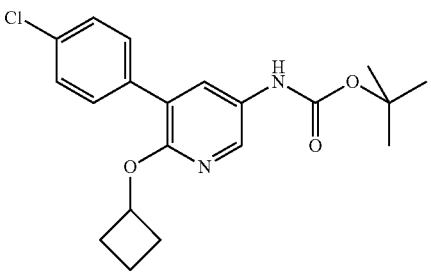 [SMILES: CC(C)(C)OC(=O)Nc1cnc(OC2CCC2)c(-c2ccc(Cl)cc2)c1]

The title compound was synthesized in analogy to Example 42e, using 5-(4-chloro-phenyl)-6-cyclobutoxynicotinic acid (example 78 b) as starting material; LC-MS (UV peak area/ESI) 92.9%, 375.1456 (M+H)+.

d) 5-(4-Chloro-phenyl)-6-cyclobutoxy-pyridin-3-ylamine

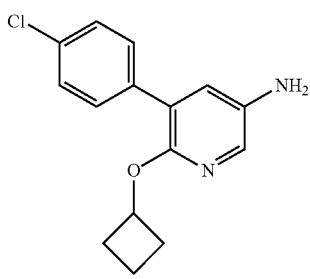 [SMILES: Nc1cnc(OC2CCC2)c(-c2ccc(Cl)cc2)c1]

[5-(4-Chloro-phenyl)-6-cyclobutoxy-pyridin-3-yl]-carbamic acid tert-butyl ester (1.042 g, 2.78 mmol) was dissolved in 4M HCl in dioxane (10.4 ml, 41.7 mmol). The reaction mixture was a light yellow solution and was stirred at room temperature for 1 h. The mixture was partitioned between ethyl acetate and 1M Na₂CO₃ solution. The organic phases were combined, dried with MgSO₄ and concentrated in vacuo. The crude material was purified by flash chromatography (silica gel, 100 g, 5% to 75% ethyl acetate in heptane) to give 0.358 g (46.9%) of the title compound as light red oil; LC-MS (UV peak area/ESI) 94.3%, 275.0950 (M+H)+.

e) N-(5-(4-chlorophenyl)-6-cyclobutoxypyridin-3-yl) pyrazine-2-carboxamide

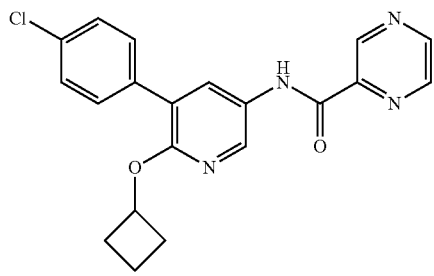 [SMILES: O=C(Nc1cnc(OC2CCC2)c(-c2ccc(Cl)cc2)c1)c1cnccn1]

The title compound was synthesized in analogy to Example 42 g, using 5-(4-chloro-phenyl)-6-cyclobutoxy-pyridin-3-ylamine (example 78 d) and 2-pyrazinecarboxylic acid (CAN 98-97-5) as starting materials; MS (EI) 381.2(M+H)+.

Example 79

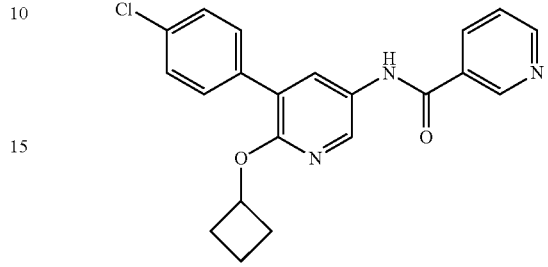

Preparation of N-(5-(4-chlorophenyl)-6-cyclobutoxy-pyridin-3-yl)nicotinamide The title compound was synthesized in analogy to Example 48e, using 5-(4-chloro-phenyl)-6-cyclobutoxy-pyridin-3-ylamine (example 78 d) and nicotinoyl chloride hydrochloride as starting materials; MS (EI) 380.2(M+H)+.

Example 80

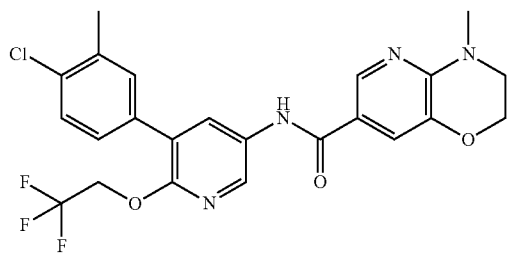 [SMILES: Cc1cc(-c2cc(NC(=O)c3cnc4c(c3)OCCN4C)cnc2OCC(F)(F)F)ccc1Cl]

Preparation of N-(5-(4-chloro-3-methylphenyl)-6-(2,2,2-trifluoroethoxy)pyridin-3-yl)-4-methyl-3,4-dihydro-2H-pyrido[3,2-b][1,4]oxazine-7-carboxamide The title compound was synthesized in analogy to Example 42 g, using 5-(4-chloro-3-methyl-phenyl)-6-(2,2,2-trifluoro-ethoxy)-pyridin-3-ylamine (example 57 a) and 3,4- dihydro-4-methyl-2H-pyrido[3,2-b]-1,4-oxazine-7-carboxylic acid (CAN 915707-58-3) as starting materials; MS (EI) 493.1(M+H)⁺.

Example 81

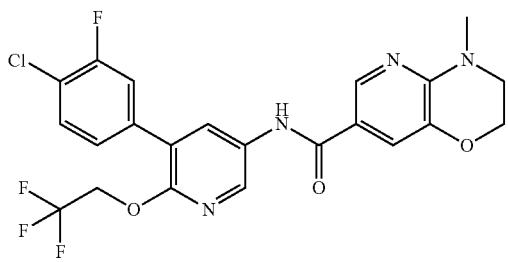 [SMILES: CN1CCOc2cc(C(=O)Nc3cnc(OCC(F)(F)F)c(-c4ccc(Cl)c(F)c4)c3)cnc21]

Preparation of N-(5-(4-chloro-3-fluorophenyl)-6-(2,2,2-trifluoroethoxy)pyridin-3-yl)-4-methyl-3,4-dihydro-2H-pyrido[3,2-b][1,4]oxazine-7-carboxamide a) 5-(4-Chloro-3-fluoro-phenyl)-6-(2,2,2-trifluoro-ethoxy)-pyridin-3-ylamine

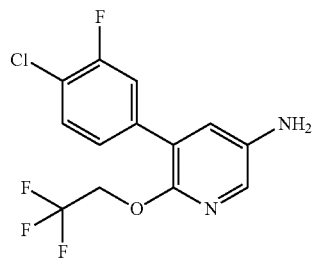 [SMILES: Nc1cnc(OCC(F)(F)F)c(-c2ccc(Cl)c(F)c2)c1]

The title compound was synthesized in analogy to Example E, using 5-bromo-6-(2,2,2-trifluoro-ethoxy)-pyridin-3-ylamine (example C) and B-(4-chloro-3-fluorophenyl)-boronic acid (CAN 137504-86-0) as starting materials; MS (EI) 379.3 (M+OAc)⁺.

b) N-(5-(4-Chloro-3-fluorophenyl)-6-(2,2,2-trifluoroethoxy)pyridin-3-yl)-4-methyl-3,4-dihydro-2H-pyrido[3,2-b][1,4]oxazine-7-carboxamide

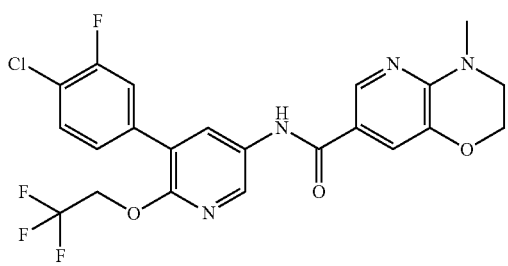 [SMILES: CN1CCOc2cc(C(=O)Nc3cnc(OCC(F)(F)F)c(-c4ccc(Cl)c(F)c4)c3)cnc21]

The title compound was synthesized in analogy to Example 42 g, using 5-(4-chloro-3-fluoro-phenyl)-6-(2,2,2-trifluoro-ethoxy)-pyridin-3-ylamine (example 81 a) and 3,4-dihydro-4-methyl-2H-pyrido[3,2-b]-1,4-oxazine-7-carboxylic acid (CAN 915707-58-3) as starting materials; MS (EI) 497.2(M+H)⁺.

Example 82

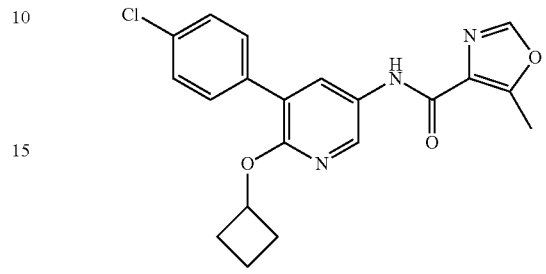

Preparation of 5-Methyl-oxazole-4-carboxylic acid [5-(4-chloro-phenyl)-6-cyclobutoxy-pyridin-3-yl]-amide The title compound was synthesized in analogy to Example 42 g, using 5-(4-chloro-phenyl)-6-cyclobutoxy-pyridin-3-ylamine (example 78 d) and 5-methyl-4-oxazolecarboxylic acid (CAN 103879-58-9) as starting materials; LC-MS (UV peak area/ESI) 100%, 384.1102 (M+H)⁺.

Example 83

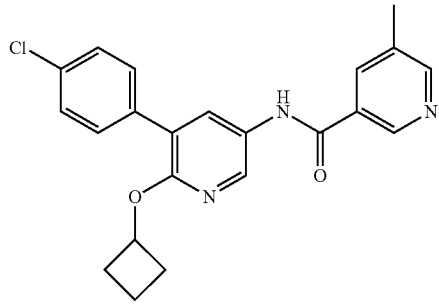 [SMILES: Cc1cncc(C(=O)Nc2cnc(OC3CCC3)c(-c3ccc(Cl)cc3)c2)c1]

Preparation of N-[5-(4-Chloro-phenyl)-6-cyclobutoxy-pyridin-3-yl]-5-methyl-nicotinamide The title compound was synthesized in analogy to Example 42 g, using 5-(4-chloro-phenyl)-6-cyclobutoxy-pyridin-3-ylamine (example 78 d) and 5-methyl-3-pyridinecarboxylic acid (CAN 40473-04-9) as starting materials; MS (EI) 394.1 (M+H)⁺.

Example 84

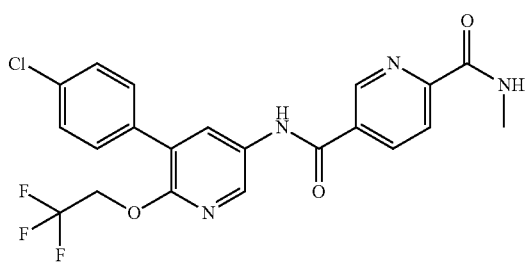 [SMILES: CNC(=O)c1ccc(C(=O)Nc2cnc(OCC(F)(F)F)c(-c3ccc(Cl)cc3)c2)cn1]

Preparation of N5-(5-(4-chlorophenyl)-6-(2,2,2-trifluoroethoxy)pyridin-3-yl)-N2-methylpyridine-2,5-dicarboxamide The title compound was synthesized in analogy to Example 42 g, using 5-(4-chloro-phenyl)-6-(2,2,2-trifluoro-ethoxy)-pyridin-3-ylamine (example E) and 6-[(methylamino)-carbonyl]-3-pyridinecarboxylic acid (CAN 170464-32-1) as starting materials; MS (EI) 465.2(M+H)⁺.

Example 85

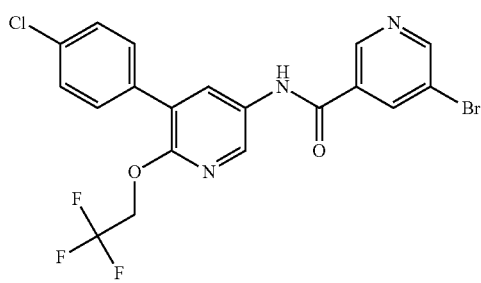 [SMILES: O=C(Nc1cnc(OCC(F)(F)F)c(-c2ccc(Cl)cc2)c1)c1cncc(Br)c1]

Preparation of 5-bromo-N-(5-(4-chlorophenyl)-6-(2,2,2-trifluoroethoxy)pyridin-3-yl)nicotinamide The title compound was synthesized in analogy to Example 42 g, using 5-(4-chloro-phenyl)-6-(2,2,2-trifluoro-ethoxy)-pyridin-3-ylamine (example E) and 5-bromo-3-pyridinecarboxylic acid (CAN 20826-04-4) as starting materials; LC-MS (UV peak area/ESI) 92.7%, 485.9662 (M–H)⁻.

Example 86

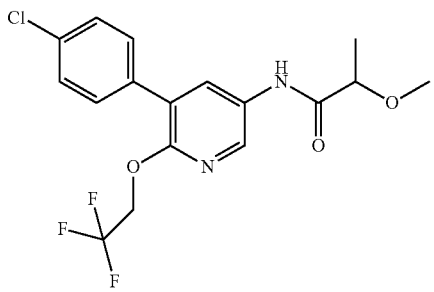 [SMILES: COC(C)C(=O)Nc1cnc(OCC(F)(F)F)c(-c2ccc(Cl)cc2)c1]

Preparation of N-(5-(4-chlorophenyl)-6-(2,2,2-trifluoroethoxy)pyridin-3-yl)-2-methoxy-propanamide The title compound was synthesized in analogy to Example 42 g, using 5-(4-chloro-phenyl)-6-(2,2,2-trifluoro-ethoxy)-pyridin-3-ylamine (example E) and 2-methoxy-propanoic acid (CAN 4324-37-2) as starting materials; MS (EI) 389.2 (M+H)⁺.

Example 87

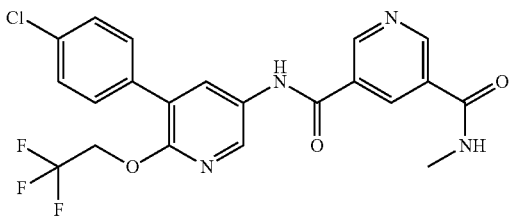 [SMILES: CNC(=O)c1cncc(C(=O)Nc2cnc(OCC(F)(F)F)c(-c3ccc(Cl)cc3)c2)c1]

Preparation of N3-(5-(4-chlorophenyl)-6-(2,2,2-trifluoroethoxy)pyridin-3-yl)-N5-methylpyridine-3,5-dicarboxamide a) 5-[5-(4-Chloro-phenyl)-6-(2,2,2-trifluoro-ethoxy)-pyridin-3-ylcarbamoyl]-nicotinic acid ethyl ester

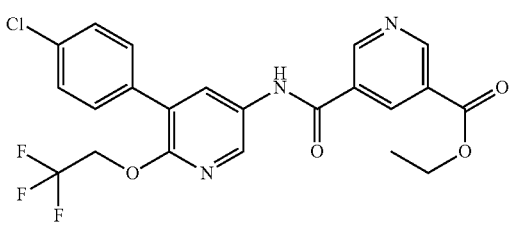 [SMILES: CCOC(=O)c1cncc(C(=O)Nc2cnc(OCC(F)(F)F)c(-c3ccc(Cl)cc3)c2)c1]

The title compound was synthesized in analogy to Example 42 g, using 5-(4-chloro-phenyl)-6-(2,2,2-trifluoro-ethoxy)-pyridin-3-ylamine (example E) and 3,5-pyridinedicarboxylic acid 3-ethyl ester (CAN 84254-37-5) as starting materials; MS (EI) 480.1(M+H)⁺.

b) 5-[5-(4-Chloro-phenyl)-6-(2,2,2-trifluoro-ethoxy)-pyridin-3-ylcarbamoyl]-nicotinic acid

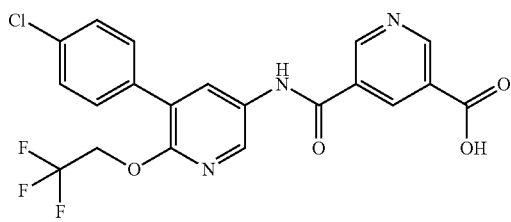 [SMILES: O=C(O)c1cncc(C(=O)Nc2cnc(OCC(F)(F)F)c(-c3ccc(Cl)cc3)c2)c1]

5-[5-(4-Chloro-phenyl)-6-(2,2,2-trifluoro-ethoxy)-pyridin-3-ylcarbamoyl]-nicotinic acid ethyl ester (510 mg, 1.06 mmol) was combined with THF (25 mL), methanol (5 mL) and water (5 mL) to give a light yellow suspension. The reaction mixture was stirred for 4 h, and concentrated in vacuo. The reaction mixture was poured into 100 mL ethyl acetate and extracted with 1 M HCl (1×25 mL) and brine (1×25 mL). The aqueous layer phases were extracted with ethyl acetate (1×50 mL). The organic layers were combined, dried with Na₂SO₄ and concentrated in vacuo. The crude material was purified by flash chromatography (silica gel, 40 g, 0% to 100% ethyl acetate in heptane) to deliver 0.17 g (48.7%) of the title compound as white solid; MS (ESI) 450.0(M−H)⁻.

c) N3-(5-(4-chlorophenyl)-6-(2,2,2-trifluoroethoxy)pyridin-3-yl)-N5-methylpyridine-3,5-dicarboxamide

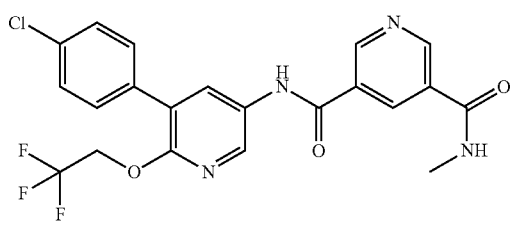 [SMILES: CNC(=O)c1cncc(C(=O)Nc2cnc(OCC(F)(F)F)c(-c3ccc(Cl)cc3)c2)c1]

5-[5-(4-Chloro-phenyl)-6-(2,2,2-trifluoro-ethoxy)-pyridin-3-ylcarbamoyl]-nicotinic acid (120 mg, 260 μmol) and methylamine hydrochloride (140 mg, 2.6 mmol) were dissolved in DMF (3 mL). TBTU (125 mg, 390 μmol) and DIPEA (672 mg, 908 μl, 5.2 mmol) were added. The reaction mixture was stirred at room temperature for 20 h. The crude reaction mixture was concentrated in vacuo and purified by flash chromatography (silica gel, 10 g, 0% to 100% ethyl acetate in heptane) to deliver 34 mg (28%) of the title compound as white solid; LC-MS (UV peak area/ESI) 99.5%, 465.0928 (M+H)⁺.

Example 88

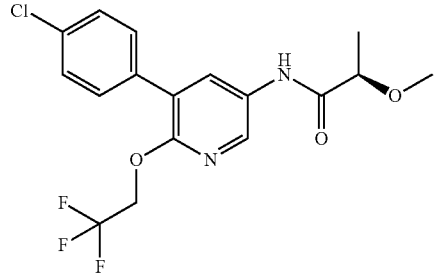 [SMILES: CO[C@H](C)C(=O)Nc1cnc(OCC(F)(F)F)c(-c2ccc(Cl)cc2)c1]

Preparation of (+)-N-(5-(4-chlorophenyl)-6-(2,2,2-trifluoroethoxy)pyridin-3-yl)-2-methoxypropanamide The title compound was synthesized in analogy to Example 42 g, using 5-(4-chloro-phenyl)-6-(2,2,2-trifluoro-ethoxy)-pyridin-3-ylamine (example E) and 2-methoxy-propanoic acid (CAN 4324-37-2) as starting materials; enantiomers were separated by chiral HPLC (ChiralPak AD, 10% ethanol/n-heptane); (+) enantiomer isolated; LC-MS (UV peak area/ESI) 100%, 389.0874 (M+H)⁺; $\alpha_D^{20}$ (MeOH)=+37.5°.

Example 89

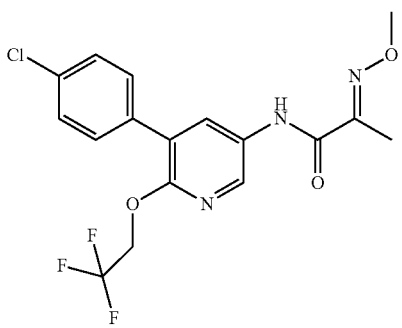 [SMILES: CO/N=C(\C)C(=O)Nc1cnc(OCC(F)(F)F)c(-c2ccc(Cl)cc2)c1]

93

Preparation of (E)-N-(5-(4-chlorophenyl)-6-(2,2,2-trifluoroethoxy)pyridin-3-yl)-2-(methoxyimino)propanamide a) N-[5-(4-Chloro-phenyl)-6-(2,2,2-trifluoro-ethoxy)-pyridin-3-yl]-2-oxo-propionamide

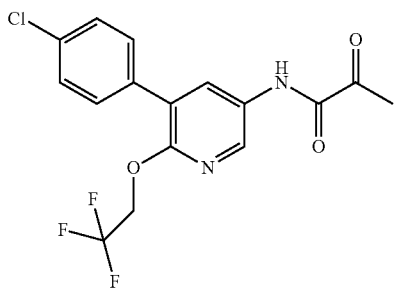 [SMILES: CC(=O)C(=O)Nc1cnc(OCC(F)(F)F)c(-c2ccc(Cl)cc2)c1]

The title compound was synthesized in analogy to Example 42 g, using 5-(4-chloro-phenyl)-6-(2,2,2-trifluoro-ethoxy)-pyridin-3-ylamine (example E) and 2-oxo-propanoic acid (127-17-3) as starting materials; MS (EI) 373.0 (M+H) +.

b) (E)-N-(5-(4-chlorophenyl)-6-(2,2,2-trifluoroethoxy)pyridin-3-yl)-2-(methoxyimino)-propanamide

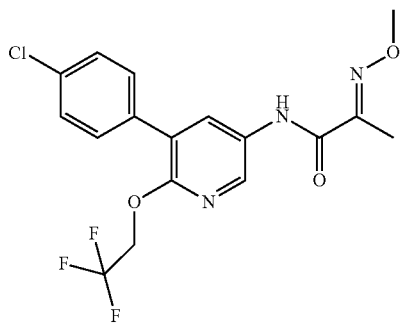 [SMILES: CO/N=C(\C)C(=O)Nc1cnc(OCC(F)(F)F)c(-c2ccc(Cl)cc2)c1]

N-[5-(4-Chloro-phenyl)-6-(2,2,2-trifluoro-ethoxy)-pyridin-3-yl]-2-oxo-propionamide (0.063 g, 169 µmol) was dissolved in methanol (1.00 mL). O-Methyl hydroxylamine hydrochloride (70.6 mg, 845 µmol) was added and the reaction mixture was stirred at room temperature overnight. The solvent was evaporated and the residue was partitioned between water and ethyl acetate; the organic phase was dried with MgSO$_4$ and concentrated in vacuo to deliver 67 mg (89%) of the title compound as white solid; LC-MS (UV peak area/ESI) 99.0%, 402.0825 (M+H)$^+$.

94

The invention claimed is:
1. A compound according to formula I,

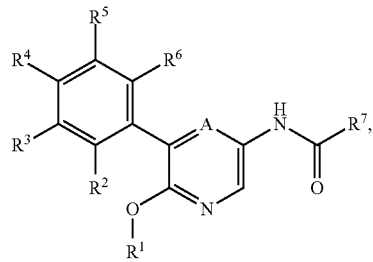

wherein
A is CH or N;
$R^1$ is selected from the group consisting of
  lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen;
$R^2$ and $R^6$ independently from each other are hydrogen or halogen;
$R^3$ and $R^5$ independently from each other are selected from the group consisting of hydrogen, lower alkyl, lower alkoxy, halogen, lower halogenalkyl, lower halogenalkoxy and cyano;
$R^4$ is selected from the group consisting of hydrogen, lower alkyl, lower alkoxy, halogen, lower halogenalkyl, lower halogenalkoxy, amino, azido and cyano; and
$R^7$ is selected from the group consisting of
  lower alkyl,
  lower hydroxyalkyl, lower alkoxyalkyl,
  lower hydroxyimino-alkyl, lower alkoxyimino-alkyl,
  lower cycloalkyl, said cycloalkyl being unsubstituted or substituted by hydroxy, lower heterocyclyl,
  phenyl, said phenyl being unsubstituted or substituted by one or two groups selected from the group consisting of lower alkyl, hydroxy, lower alkoxy, cyano, lower alkylaminocarbonyl and halogen, and
  heteroaryl, said heteroaryl being unsubstituted or substituted by one or two groups selected from the group consisting of lower alkyl, hydroxy, lower alkoxy, cyano, lower alkylaminocarbonyl and halogen;
or a pharmaceutically acceptable salt thereof.
2. A compound according to claim 1, wherein $R^1$ is lower cycloalkylalkyl or lower halogenalkyl.
3. A compound according to claim 1, wherein $R^1$ is lower halogenalkyl.
4. A compound according to claim 1, wherein $R^2$ and $R^6$ are hydrogen.
5. A compound according to claim 1, wherein $R^3$ and $R^5$ are each independently hydrogen or lower alkyl.

6. A compound according to claim 1, wherein $R^4$ is lower alkyl or halogen.

7. A compound according to claim 1 wherein $R^4$ is halogen.

8. A compound according to claim 1, wherein $R^7$ is phenyl, said phenyl being unsubstituted or substituted by one or two groups selected from the group consisting of lower alkyl, hydroxy, cyano, lower alkylaminocarbonyl and halogen, or heteroaryl, said heteroaryl being unsubstituted or substituted by one or two groups selected from the group consisting of lower alkyl, hydroxy, cyano, lower alkylaminocarbonyl and halogen.

9. A compound according to claim 1, wherein $R^7$ is heteroaryl, said heteroaryl being unsubstituted or substituted by one or two groups selected from the group consisting of lower alkyl, hydroxy, cyano, lower alkylaminocarbonyl and halogen.

10. A compound according to claim 1, wherein heteroaryl is selected from the group consisting of furanyl, oxazolyl, isoxazolyl, pyrazolyl, thiazolyl, isothiazolyl, [1,2,3]thiadiazolyl, pyridyl, pyrazinyl, pyridazinyl, pyrimidinyl and 3,4-dihydro-2H-pyrido[3,2-b][1,4]oxazinyl, said heteroaryl being unsubstituted or substituted by one or two groups selected from the group consisting of lower alkyl, hydroxy, cyano, lower alkylaminocarbonyl and halogen.

11. A compound according to claim 1, wherein A is CH.

12. A compound according to claim 1 having the formula

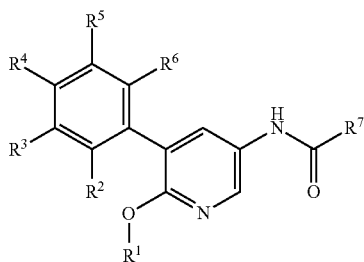

I-AA wherein
$R^1$ is selected from the group consisting of
  lower alkyl,
  cycloalkyl,
  lower cycloalkylalkyl,
  lower hydroxyalkyl,
  lower alkoxyalkyl,
  lower halogenalkyl,
  lower carbamoylalkyl,
  lower alkylcarbonylaminoalkyl,
  lower phenylalkyl,
  lower heterocyclylalkyl wherein the heterocyclyl group is unsubstituted or substituted by oxo,
  lower heteroarylalkyl wherein the heteroaryl group is unsubstituted or mono- or di-substituted by lower alkyl, and
  phenyl which is unsubstituted or mono- or di-substituted by halogen
$R^2$ and $R^6$ independently from each other are hydrogen or halogen;
$R^3$ and $R^5$ independently from each other are selected from the group consisting of hydrogen, lower alkyl, lower alkoxy, halogen, lower halogenalkyl, lower halogenalkoxy and cyano;
$R^4$ is selected from the group consisting of hydrogen, lower alkoxy, halogen, lower halogenalkyl, lower halogenalkoxy, amino, azido and cyano; and
$R^7$ is selected from the group consisting of
  lower alkyl,
  lower hydroxyalkyl,
  lower cycloalkyl, said cycloalkyl being unsubstituted or substituted by hydroxy, lower heterocyclyl,
  phenyl, said phenyl being unsubstituted or substituted by one or two groups selected from the group consisting of lower alkyl, hydroxy and halogen, and
  heteroaryl, said heteroaryl being unsubstituted or substituted by one or two groups selected from the group consisting of lower alkyl, hydroxy, cyano and halogen;
or a pharmaceutically acceptable salt thereof.

13. A compound according to claim 1, selected from the group consisting of
  N-[5-(4-chloro-phenyl)-6-(2,2,2-trifluoro-ethoxy)-pyridin-3-yl]-nicotinamide,
  N-[5-(4-chloro-phenyl)-6-cyclopropylmethoxy-pyridin-3-yl]-nicotinamide,
  3-methyl-isoxazole-4-carboxylic acid[5-(4-chloro-phenyl)-6-(2,2,2-trifluoro-ethoxy)-pyridin-3-yl]-amide,
  pyridazine-3-carboxylic acid[5-(4-chloro-phenyl)-6-(2,2,2-trifluoro-ethoxy)-pyridin-3-yl]-amide,
  1,3-dimethyl-1H-pyrazole-4-carboxylic acid[5-(4-chloro-phenyl)-6-(2,2,2-trifluoro-ethoxy)-pyridin-3-yl]-amide,
  5-methyl-oxazole-4-carboxylic acid[5-(4-chloro-phenyl)-6-(2,2,2-trifluoro-ethoxy)-pyridin-3-yl]-amide,
  N-(5-(4-chloro-3-methylphenyl)-6-(2,2,2-trifluoroethoxy)pyridin-3-yl)-nicotinamide,
  N-(5-(4-chloro-3-fluorophenyl)-6-(2,2,2-trifluoroethoxy)pyridin-3-yl)nicotinamide,
  (S)-N-(6-(4-chlorophenyl)-5-(1,1,1-trifluoropropan-2-yloxy)pyrazin-2-yl)nicotinamide,
  N-(6-(4-chlorophenyl)-5-cyclobutoxypyrazin-2-yl)pyrimidine-5-carboxamide,
  N-(5-(4-chloro-2-fluorophenyl)-6-(2,2,2-trifluoroethoxy)pyridin-3-yl)pyrimidine-5-carboxamide,
  N-(5-(4-chlorophenyl)-6-(2,2,2-trifluoroethoxy)pyridin-3-yl)-2-hydroxybenzamide,
  N-(5-(4-chloro-3-methylphenyl)-6-(2,2,2-trifluoroethoxy)pyridin-3-yl)-5-cyanonicotinamide,
  N-(5-(4-chloro-2-fluorophenyl)-6-(2,2,2-trifluoroethoxy)pyridin-3-yl)pyridazine-3-carboxamide,
  N-(5-(4-chlorophenyl)-6-(2,2,2-trifluoroethoxy)pyridin-3-yl)-5-methylfuran-2-carboxamide,
  N-(5-(4-chlorophenyl)-6-(2,2,2-trifluoroethoxy)pyridin-3-yl)-4-methyl-3,4-dihydro-2H-pyrido[3,2-b][1,4]oxazine-7-carboxamide,
  N-(5-(4-chlorophenyl)-6-(2,2,2-trifluoroethoxy)pyridin-3-yl)-5-methoxynicotinamide, and
  N-(5-(4-chlorophenyl)-6-(2,2,2-trifluoroethoxy)pyridin-3-yl)-2-methoxypropanamide,
and pharmaceutically acceptable salts thereof.

14. A pharmaceutical composition comprising a compound according to claim 1 and a pharmaceutically acceptable carrier and/or adjuvant.

* * * * *